US009676677B2

(12) United States Patent
Freitas, Jr. et al.

(10) Patent No.: US 9,676,677 B2
(45) Date of Patent: Jun. 13, 2017

(54) BUILD SEQUENCES FOR MECHANOSYNTHESIS

(71) Applicants: Robert A. Freitas, Jr., Pilot Hill, CA (US); Ralph C. Merkle, Cupertino, CA (US)

(72) Inventors: Robert A. Freitas, Jr., Pilot Hill, CA (US); Ralph C. Merkle, Cupertino, CA (US)

(*) Notice: Subject to any disclaimer, the term of this patent is extended or adjusted under 35 U.S.C. 154(b) by 208 days.

(21) Appl. No.: 14/712,506

(22) Filed: May 14, 2015

(65) Prior Publication Data
US 2015/0355228 A1   Dec. 10, 2015

Related U.S. Application Data

(63) Continuation-in-part of application No. PCT/US2013/028419, filed on Feb. 28, 2013.

(51) Int. Cl.
  *C07B 37/10* (2006.01)
  *C07B 37/00* (2006.01)
  *B82B 3/00* (2006.01)

(52) U.S. Cl.
  CPC .......... *C07B 37/10* (2013.01); *B82B 3/0038* (2013.01); *C07B 37/00* (2013.01)

(58) Field of Classification Search
  CPC ......... C07B 37/00; C07B 37/02; C07B 37/04; C07B 37/10; C07B 61/00; B82B 3/00; B82B 3/0004; B82B 3/0009; B82B 3/0014; B82B 3/0023; B82Y 40/00; B82Y 90/00; B01J 19/00; G01Q 80/00
  See application file for complete search history.

(56) References Cited

U.S. PATENT DOCUMENTS

| | | |
|---|---|---|
| 3,859,352 A | 1/1975 | Szinai et al. |
| 4,952,749 A | 8/1990 | Alexander et al. |
| 4,987,312 A | 1/1991 | Eigler |
| 5,144,148 A | 9/1992 | Eigler |
| 5,372,659 A | 12/1994 | Lamaze et al. |
| 5,411,797 A | 5/1995 | Davanloo et al. |
| 5,824,470 A | 10/1998 | Baldeschwieler et al. |
| 6,017,504 A | 1/2000 | Kaliaguine et al. |
| 6,242,470 B1 | 6/2001 | Baxter et al. |

(Continued)

OTHER PUBLICATIONS

Tarasov et al, "Optimal Tooltip Trajectories in a Hydrogen Abstraction Tool Recharge Reaction Sequence for Positionally Controlled Diamond Mechanosynthesis", Journal of Computational and Theoretical Nanoscience, vol. 7 1-29, 2010.*

(Continued)

*Primary Examiner* — David E Smith
(74) *Attorney, Agent, or Firm* — P. J. Benedict O'Mahoney

(57) ABSTRACT

Processes for creating build sequences are described which use computational chemistry algorithms to simulate mechanosynthetic reactions, and which may use the mechanosynthesis process conditions or equipment limitations in these simulations, and which facilitate determining a set of mechanosynthetic reactions that will build an atomically-precise workpiece with a desired degree of reliability. Included are methods for error correction of pathological reactions or avoidance of pathological reactions. Libraries of reactions may be used to reduce simulation requirements.

10 Claims, 21 Drawing Sheets

(56) References Cited

U.S. PATENT DOCUMENTS

| | | |
|---|---|---|
| 6,339,227 B1 | 1/2002 | Ellenbogen |
| 6,348,700 B1 | 2/2002 | Ellenbogen et al. |
| 6,422,077 B1 | 7/2002 | Krauss et al. |
| 6,531,107 B1 | 3/2003 | Spencer et al. |
| 6,716,409 B2 | 4/2004 | Hafner et al. |
| 6,783,589 B2 | 8/2004 | Dahl |
| 6,827,979 B2 | 12/2004 | Mirkin et al. |
| 6,835,534 B2 | 12/2004 | Weiss et al. |
| 6,864,481 B2 | 3/2005 | Kaito et al. |
| 6,886,395 B2 | 5/2005 | Minne |
| 6,987,277 B2 | 1/2006 | Baur et al. |
| 7,049,374 B2 | 5/2006 | Liu et al. |
| 7,189,455 B2 | 3/2007 | Wong et al. |
| 7,211,795 B2 | 5/2007 | Collier et al. |
| 7,282,710 B1 | 10/2007 | Black et al. |
| 7,291,284 B2 | 11/2007 | Mirkin et al. |
| 7,309,476 B2 | 12/2007 | Carlson et al. |
| 7,312,562 B2 | 12/2007 | Dahl et al. |
| 7,326,293 B2 | 2/2008 | Randall et al. |
| 7,326,923 B2 | 2/2008 | Berstis |
| 7,381,625 B2 | 6/2008 | Xi et al. |
| 7,431,856 B2 | 10/2008 | Rezeq et al. |
| 7,687,146 B1 | 3/2010 | Freitas |
| 8,171,568 B2 | 5/2012 | Freitas et al. |
| 2003/0215877 A1 | 11/2003 | Love et al. |
| 2004/0014168 A1 | 1/2004 | Schreiber et al. |
| 2009/0056802 A1* | 3/2009 | Rabani .................. B82B 3/00 136/256 |
| 2009/0093659 A1* | 4/2009 | Freitas, Jr. ............ C07C 2/00 585/21 |
| 2014/0231379 A1 | 8/2014 | Pitters et al. |

OTHER PUBLICATIONS

Freitas, Robert, and Merkle, Ralph. "A Minimal Toolset for Positional Diamond Mechanosynthesis", Journal of Computational and Theoretical Nanoscience, vol. 5, 760-861, 2008.*

Y. Fukuda, M. Shimomura, G. Kaneda, N. Sanada, V.G. Zavodinsky, I.A. Kuyanov, E.N. Chukurov, "Scanning tunneling microscopy, high-resolution electron energy loss spectroscopy, and theoretical studies of trimethylphosphine (TMP) on a Si(111)-(7×7) surface," Surf. Sci. 442(1999):507-516.

Balasubramanian, K. and Burghard, M. (2005), "Chemically functionalized carbon nanotubes", Small 2005, 1, No. 2, 180-192.

Herman, A. (2012), "Toward Mechanosynthesis of Diamondoid Structures: IX Commercial Capped CNT Scanning Probe Microscopy Tip as Nowadays Available Tool for Silylene Molecule and Silicon Atom Transfer", Journal of Computational and Theoretical Nanoscience.

Herman, A. (2013), "Toward Mechanosynthesis of Diamondoid Structures: X. Commercial Capped CNT SPM Tip as Nowadays Available C2 Dimer Replacement Tool for Tip-Based Nanofabrication", Journal of Computation and Theoretical Nanoscience.

Lagoute, J., Liu, X., et al. (2006), "Electronic properties of straight, kinked, and branchedCu/Cu(111)quantum wires: A low-temperature scanning tunneling microscopy and spectroscopy study", Physical Review B.

Murota. J., Sakuraba, M., et al. (2006), "Atomically Controlled Processing for Group IV Semiconductors by Chemical Vapor Deposition", Japanese Journal of Applied Physics.

Zhang, B., Wepf, R., et al. (2011), "The Largest Synthetic Structure with Molecular Precision: Towards a Molecular Object", Angewandte Chemie International Edition.

Freitas, R. and Merkle, R. (2008), "A Minimal Toolset for Positional Diamond Mechanosynthesis", Journal of Computational and Theoretical Nanoscience.

Mann, D., Peng, J., et al. (2004), "Theoretical Analysis of Diamond Mechanosynthesis. Part II. C2 Mediated Growth of Diamond C(110) Surface via Si/Ge-Triadamantane Dimer Placement Tools", Journal of Computational and Theoretical Nanoscience.

Peng, J., Freitas, R., et al. (2004), "Theoretical Analysis of Diamond Mechanosynthesis. Part I. Stability of C2 Mediated Growth of Nanocrystalline Diamond C(110) Surface", Journal of Computational and Theoretical Nanoscience.

Jingping Peng, Robert A. Freitas Jr., Ralph C. Merkle, James R. Von Ehr, John N. Randall, George D. Skidmore, "Theoretical Analysis of Diamond Mechanosynthesis. Part III. Positional C2 Deposition of Diamond C(110) Surface using Si/Ge/Sn-based Dimer Placement Tools," J. Comput. Theor. Nanosci. 3 (Feb. 2006):28-41.

Berhane Temelso, C. David Sherrill, Ralph C. Merkle, Robert A. Freitas Jr., "High-level Ab Initio Studies of Hydrogen Abstraction from Prototype Hydrocarbon Systems," J. Phys. Chem. A 110 (Sep. 28, 2006):11160-11173.

Berhane Temelso, C. David Sherrill, Ralph C. Merkle, Robert A. Freitas Jr., "Ab Initio Thermochemistry of the Hydrogenation of Hydrocarbon Radicals Using Silicon, Germanium, Tin and Lead Substituted Methane and Isobutane," J. Phys. Chem. A 111(Aug. 15, 2007):8677-8688.

K. Eric Drexler, Nanosystems: Molecular Machinery, Manufacturing, and Computation, John Wiley & Sons, New York, 1992, Chapter 8.

D.M. Eigler, E.K. Schweizer, "Positioning Single Atoms with a Scanning Tunnelling Microscope," Nature 344(Apr. 5, 1990):524-526.

Noriaki Oyabu, Oscar Custance, Insook Yi, Yasuhiro Sugawara, Seizo Morita, "Mechanical vertical manipulation of selected single atoms by soft nanoindentation using near contact atomic force microscopy," Phys. Rev. Lett. 90(May 2, 2003):176102.

Ralph C. Merkle, "A proposed 'metabolism' for a hydrocarbon assembler," Nanotechnology 8(1997):149-162.

M.C. Hersam, G.C. Abeln, J.W. Lyding, "An approach for efficiently locating and electrically contacting nanostructures fabricated via UHV-STM lithography on Si(100)," Microelectronic Engineering 47(Jun. 1999):235-237.

D.H. Huang, Y. Yamamoto, "Physical mechanism of hydrogen deposition from a scanning tunneling microscopy tip," Appl. Phys. A 64(Apr. 1997):R419-R422.

J. Murota, M. Sakuraba, "Atomically controlled processing for high-performance Si-based devices," Tohoku-Cambridge Forum (Hall in Peterhouse, University of Cambridge, Organizers: M. Koyanagi, W. I. Milne), International Workshop on Nano-Technology, Nano-Materials, Nano-Devices, and Nano-Systems, Jun. 11, 2004.

J. Franks, "Preparation and properties of diamondlike carbon films," J. Vac. Sci. & Technol. A 7(May 1989):2307-2310.

C.A. Rego, P.W. May, E.C. Williamson, M.N.R. Ashfold, Q.S. Chia, K.N. Rosser, N.M. Everitt, "CVD diamond growth on germanium for infra-red window applications," Diam. Rel. Mater. 3(1994):939.

D.S. Patil, K. Ramachandran, N. Venkatramani, M. Pandey, R. D'Cunha, "Microwave plasma deposition of diamond-like carbon coatings," Pramana J. Phys. 55(Nov./Dec. 2000):933-939.

M.J. Bronikowski, R.J. Hamers, "The chemistry of gallium deposition on Si(001) from trimethylgallium: an atomically resolved STM study," Surf. Sci. 348(Mar. 10, 1996):311-324.

D.M. Gruen, S. Liu, A. R. Krauss, X.Pan, "Buckyball microwave plasmas: Fragmentation and diamond-film growth," J. Appl. Phys. 75(1994):1758-1763.

Ansoon Kim, Jae Yeol Maeng, Jun Young Lee, Sehun Kim, "Adsorption configuration and thermal chemistry of acetylene on the Ge(100) surface," J. Chem. Phys. 117(Dec. 8, 2002):10215-10222.

Guangquan Lu, John E. Crowell, "The adsorption and thermal decomposition of digermane on Ge(111)," J. Chem. Phys. 98(Feb. 15, 1993):3415-3421.

N. Oyabu, O. Custance, M. Abe, S. Moritabe, "Mechanical Vertical Manipulation of Single Atoms on the Ge(111)-c(2×8) Surface by Noncontact Atomic Force Microscopy," Abstracts of Seventh International Conference on Non-Contact Atomic Force Microscopy, Seattle, Washington, USA, Sep. 12-15, 2004.

P.D. Nellist, M.F. Chisholm, N. Dellby, O.L. Krivanek, M.F. Murfitt, Z.S. Szilagyi, A.R. Lupini, A. Borisevich, W.H. Sides, Jr., S.J. Pennycock, "Direct Sub-Angstrom Imaging of a Crystal Lattice," Science 305(Sep. 17, 2004):1741.

(56) References Cited

OTHER PUBLICATIONS

G. Basile, P. Becker, A. Bergamin, G. Cavagnero, A. Franks, K. Jackson, U. Kuetgens, G. Mana, E.W. Palmer, C.J. Robbie, M. Stedman, J. Stumpel, A. Yacoot, G. Zosi, "Combined optical and X-ray interferometry for high-precision dimensional metrology", Proc. R. Soc. Lond. A (2000) 456, 701-729.

Y. Sugimoto, P. Pou, O. Custance, P. Jelinek, M. Abe, R. Perez, S. Morita, "Complex Patterning by Vertical Interchange Atom Manipulation Using Atomic Force Microscopy", Science 322, 413 (2008).

Artyukhov, V. I., "A six degree of freedom nanomanipulator design based on carbon nanotube bundles." Nanotechnology 21(38): 9 (2010).

Duwez, A., Cuenot, S., et al., "Mechanochemistry: targeted delivery of single molecules." Nature Nanotechnology 1(2): 122-125 (2010).

Ho, W. and Lee, H., "Single bond formation and characterization with a scanning tunneling microscope." Science (286): 1719-1722 (2010).

Tarasov, D., Akberova, N., et al. (2010). "Optimal Tooltip Trajectories in a Hydrogen Abstraction Tool Recharge Reaction Sequence for Positionally Controlled Diamond Mechanosynthesis." J. Comput. Theor. Nanosci. 7(2): 325-353.

Yang, S. H., Kim, Y.S., et al. (2012). "Microelectromechanical systems based Stewart platform with sub-nano resolution." Appl. Phys. Lett. 101(6): 5.

Johannes, M. S. (2006). "Automated CAD/CAM-based nanolithography using a custom atomic force microscope." IEEE Transactions on Automation Science and Engineering 3(3): 236-239.

Ramachandran, T., Baur, C., et al. (1998). "Direct and Controlled Manipulation of Nanometer-Sized Particles Using the Non-Contact Atomic Force Microscope." Nanotechnology(9): 237-245.

Tay, A. B. H. and Thong, J. T. L. (2004). "Fabrication of super-sharp nanowire atomic force microscope using a field emission induced growth technique." Review of Scientific Instruments 75(10).

Wong, S., Woolley, A., et al. (1999). "Functionalization of carbon nanotube AFM probes using tip-activated gases." Chemical Physics Letters(306): 219-225.

Hafner, J., Cheung, C., et al. (2001). "Structural and Functional Imaging with Carbon Nanotube AFM Probes." Progress in Biophysics & Molecular Biology 1(77): 73-110.

Chen, H. (2006). "CAD-guided automated nanoassembly using atomic force microscopy-based nonrobotics." IEEE Transactions on Automation Science and Engineering 3(3): 208-217.

Grandbois, M., Dettmann, W., et al. (2000). "Affinity Imaging of Red Blood Cells Using an Atomic Force Microscope." Journal of Histochemistry & Cytochemistry(48): 719-724.

Morita, S., Sugimoto, Y., et al. (2004). "Atom-selective imaging and mechanical atom manipulation using the non-contact atomic force microscope." J. Electron Microsc. 53(2): 163-168.

Meyer, G., Neu, B., et al (1995), Building Nanostructures by Controlled Manipulation of Single Atoms and Molecules with the Scanning Tunneling Microscope, Phys Stat Sol.

Bartels, L., Meyer, G., et al. (1997) "Controlled vertical manipulation of single CO molecules with the scanning tunneling microscope: A route to chemical contrast", Applied Physics Letters.

Bartels, L., Meyer, G., et al. (1997) "Basic Steps of Lateral Manipulation of Single Atoms and Diatomic Clusters with a Scanning Tunneling Microscope Tip", Physical Review Letters.

Hla, S., Bartels, L., et al. (2000), "Inducing All Steps of a Chemical Reastion with the Scanning Tunneling Microscope Tip: Towards Single Molecule Engineering", Physical Review Letters.

* cited by examiner

US 9,676,677 B2

BUILD SEQUENCES FOR MECHANOSYNTHESIS

CROSS-REFERENCE TO RELATED APPLICATIONS

This application is a continuation-in-part of International Application Ser. No. PCT/US2013/028419, filed 28 Feb. 2013. This application is incorporated herein by reference.

FEDERALLY SPONSORED RESEARCH

Not applicable.

SEQUENCE LISTING OR PROGRAM

A CD (and duplicate copy) containing lengthy tables with data representing molecular models which illustrate each reaction in Table 2 and exemplary intermediate products from Table 3 has been included with this application and is incorporated herein by reference. The CD contains 77 files totaling 1.1 MB in size. The table files are in .hin format, which may be opened in any text editor for a tabular text view with columns identifying the atom, charge, coordinates and bonds; and which can also be read with HyperChem, Jmol, or a variety of other computational chemistry programs for a graphical view of the molecular model. The names of the files contained on the CD, their date of creation and size in bytes are noted in Transmittal of Tables.

FIELD OF INVENTION

The present application relates to mechanosynthesis, the fabrication of atomically precise tools and materials using individual atoms or small groups of atoms as the fundamental building blocks, and more particularly, to devices, methods and systems for performing ordered sequences of site-specific positionally controlled chemical reactions that are induced by use of mechanical force.

BACKGROUND OF THE INVENTION

Mechanosynthesis and Mechanosynthesis Terminology

Atomic Force Microscopes (AFM) and similar devices (e.g., SFM, SPM, STM) have long been used to move individual atoms or molecules to precise locations. Early experiments included the use of atoms or molecules to create patterns on surfaces, or to cause chemical reactions. Examples of such work include (Meyer, Neu et al., "Building Nanostructures by Controlled Manipulation of Single Atoms and Molecules with the Scanning Tunneling Microscope," Phys Stat Sol, 1995; Bartels, Meyer et al., "Basic Steps of Lateral Manipulation of Single Atoms and Diatomic Clusters with an Scanning Tunneling Microscope Tip," Physical Review Letters, 4, 1997; Bartels, Meyer et al., "Controlled vertical manipulation of single CO molecules with the scanning tunneling microscope: A route to chemical contrast," Applied Physics Letters, 2, 1997; Hla, Bartels et al., "Inducing All Steps of a Chemical Reaction with the Scanning Tunneling Microscope Tip: Towards Single Molecule Engineering," PHYSICAL REVIEW LETTERS, 13, 2000).

These early experiments generally did not involve creating covalent bonds, or if they did, the reactions were electron-induced rather than caused by physical force. Subsequently, it became possible to use precise physical positioning and, if necessary, force, to make or break bonds; this is called mechanosynthesis. Mechanosynthesis was experimentally demonstrated in 2003 (Oyabu, Custance et al., "Mechanical vertical manipulation of selected single atoms by soft nanoindentation using near contact atomic force microscopy," Phys. Rev. Lett., 17, 2003).

Several authors have explored the idea of atomically-precise manufacturing (Drexler, "Engines of Creation: The Coming Era of Nanotechnology," Anchor, 1987; Drexler, "Nanosystems: Molecular Machinery, Manufacturing, and Computation," New York, John Wiley & Sons, 1992; Freitas, "Nanomedicine, Volume I: Basic Capabilities," Landes Bioscience, 1999; "Nanomedicine, Vol. IIA: Biocompatibility," Landes Bioscience, 2003). But, despite long-standing conjecture and theoretical work in the field, mechanosynthesis has largely been treated as a laboratory curiosity due to the challenges that need to be addressed in order to develop it into a useful manufacturing technology.

The present invention describes methods, systems and products relating to the use of mechanosynthesis to manufacture atomically-precise structures. The structures are referred to as workpieces, and the workpieces are built using atoms (including groups of atoms or molecules) as raw material. These atoms are referred to as feedstock. Workpieces are built using tips to move feedstock atoms into desired locations on a workpiece, to remove undesired atoms from the workpiece, or to alter the bond structure of the workpiece. The positional control and force required for the tips can be supplied by an AFM, DAFM, KPFM, NC-AFM, SFM, SPM, STM, or any other appropriate device, including devices built specifically for the purposes of mechanosynthesis, rather than microscopes adapted to that purpose.

The order in which atoms are added, removed, or altered during the course of building a workpiece is referred to as a build sequence. A build sequence also encompasses the concept of a trajectory, which is the path along which an atom moves during a mechanosynthetic reaction. By using tips to move feedstock along a trajectory, to a specific location with respect to a workpiece, and then applying mechanical force as needed to bond the atom into position (or facilitate other reactions, such as the removal of atoms or rearrangement of bonds), atomically-precise workpieces can be manufactured.

Tips Used in Mechanosynthesis

The mechanosynthesis processes described herein use ultra-sharp tips designed to move atoms with sub-angstrom precision and to facilitate different reactions with those atoms. The tips may be, but do not have to be, atomically-precise. While some embodiments of the invention use atomically-precise tips, others do not. For example, a bootstrap sequence is presented herein which allows the creation of atomically-precise tips using non-atomically-precise tips.

Atomically imprecise, but ultra-sharp tips, also called probes, are available commercially (e.g., from Nanotools Gmbh, Munich, Germany; NANOSENSORS, Neuchatel, Switzerland; or NanoAndMore GMBH, Lady's Island, S.C. USA), or can be made using electron-beam induced deposition (EBID), among others techniques. (Tay and Thong, "Fabrication of super-sharp nanowire atomic force microscope using a field emission induced growth technique," Review of Scientific Instruments, 10, 2004) Such tips can serve as a starting point for the bootstrap process described herein. Other tips available include carbon nanotube-based tips which can be functionalized to perform various reactions (Balasubramanian and Burghard, "Chemically functionalized carbon nanotubes," Small, 2, 2005; Herman, "Toward Mechanosynthesis of Diamondoid Structures: IX Commercial Capped CNT Scanning Probe Microscopy Tip as Nowadays Available Tool for Silylene Molecule and Silicon Atom Transfer," Journal of Computational and Theoretical Nanoscience, 12, 2012; "Toward Mechanosynthesis of Diamondoid Structures: X. Commercial Capped CNT SPM Tip as Nowadays Available C2 Dimer Placement Tool for Tip-Based Nanofabrication," Journal of Computational and Theoretical Nanoscience, 9, 2013) and atomically-sharp tips created using field assisted etching (Rezeq, Pitters et al., "Nano-tip fabrication by spatially controlled etching," U.S. Pat. No. 7,431,856, 2008; Pitters, Urban et al., "Method of fabricating nanotips with controlled profile," US Patent App 20140231379, 2014).

In general, the important characteristic of a tip is that it reliably performs the desired mechanosynthetic reaction. Atomic precision is a helpful characteristic of tips for mechanosynthesis because knowing the precise placement of atoms on the tip allows the design of reliable. This is not to say that atomically imprecise tips could not be used in mechanosynthesis processes (as the bootstrap process discussed herein demonstrates), for example, by characterizing each tip before use, by designing reactions where variation at the tip does not substantially affect the intended reactions, or by designing procedures which result in minimal tip-to-tip variation when preparing tips. However, the focus herein is on the use of atomically-precise tips (after bootstrapping) for a variety of reasons, including consistency and amenability to simulation.

Note that "tips" and "workpieces" are discussed extensively herein. However, defining one structure as a tip and another as a workpiece can be arbitrary in some circumstances. For example, when a tip removes a hydrogen atom from a workpiece, one might also say that the workpiece donated a hydrogen atom to the tip, logically reversing their roles. This distinction may seem pedantic, but can be meaningful in some situations such as recharging a tip (by adding feedstock, removing waste atoms, or both), or using one set of tips to build another set of tips. In such instances, because you are adding or removing atoms from a tip, or because you are building new tips, a tip could be the workpiece.

Enabling Technologies

Mechanosynthesis equipment, process, and workpiece design is largely based upon the confluence of atomic microscopy and computational chemistry. Microscopy techniques such as Scanning Probe Microscopy (SPM), Scanning Tunneling Microscopy (STM) and Atomic Force Microscopy (AFM) have led to the ability to image and manipulate individual atoms, while computational chemistry has led to the ability to model structures which can be built by manipulating atoms, as well as the reactions used to build the structures, and the tools required to carry out the reactions.

The ability to perform robust mechanosynthesis requires that one be able to position atoms (generally with sub-angstrom precision), that one be able to apply mechanical force to an atom in a specific direction to cause the making or breaking of bonds, that one be able to design a desired workpiece with atomic precision, that one be able to calculate trajectories which will result in successful mechanosynthetic reactions, and that one possess, or be able to design, tips to carry out the intended reactions.

In addition to this list of necessities, it would be beneficial to be able to calculate the likelihood of pathological side reactions during mechanosynthetic reactions (the likelihood that, for example, a feedstock atom bonds to a workpiece atom adjacent to the intended target atom), the likelihood of pathological rearrangements before, during, or after a mechanosynthetic reaction, and to have control of the reaction environment (e.g., to make sure that it is inert with respect to the reactions being used and kept at an appropriate temperature).

Herein are describe methods, products and systems for addressing each one of these issues, taking mechanosynthesis from a laboratory curiosity to an actual manufacturing technology.

Computational Chemistry in Mechanosynthesis

Computational chemistry techniques can be very accurate. However, even on powerful computers simulating large numbers of atoms at high levels of theory, and potentially using multi-scale techniques (e.g., ONIOM), multiple algorithms to "sanity check" results, and large basis sets, can be extremely computationally-demanding. However, an entire mechanosynthetic system need not be simulated at a high level of detail. Mechanosynthesis can be carried out in a more controlled environment than, for example, traditional liquid or gas phase chemistry, or biology experiments, resulting in the ability to simplify simulations by reducing the number of atoms which are simulated at high levels of detail.

In mechanosynthesis only a few, positionally-controlled atoms are participating in a reaction at any given time. Most reactions away from the intended reaction site can be prevented by using an inert environment (e.g., a vacuum), and the ability to carry out reactions at low temperatures can help with reactions that cannot be prevented in this manner. Therefore, the number of atoms that are directly relevant to a given reaction and thus must be simulated with high fidelity is quite small compared to the overall mechanosynthetic system or to other common settings in which chemical reactions take place. As a result, is that it is feasible to use computational chemistry techniques to simulate mechanosynthetic systems and reactions accurately enough to make reliable predictions about the behavior of those systems and reactions.

Element Grouping and Simulation. When referring to groups of elements herein, groups used include metals, non-metals, noble gases, transuranic elements, stable elements (defined as non-radioactive isotopes and isotopes with half-lives long enough to support the manufacturing and use of a product), or other logical groupings. The rationale behind these groupings would be obvious to one skilled in the art: generally the distinction is one of chemical properties (e.g., those in the same family on the periodic table or with the same valence), simulation feasibility, or practicality (e.g., safety aside, creating a device using isotopes with very short half-lives could pose problems in manufacturing and use of a device before the isotopes decay). In instances where a seemingly-arbitrary group of elements is specified, this is generally because reactions have been simulated using the elements in the group. This will be clear from the data presented herein.

Discussion of the Literature

The literature contains several examples of the computational analysis of mechanosynthesis, as well as experimental mechanosynthesis. However, this work tends to treat mechanosynthesis as a laboratory curiosity rather than attempting to address the issues inherent in creating a viable manufacturing technology. For example, the experimental literature is generally limited to decorating or modifying surfaces, and limited to small numbers of reactions.

No three-dimensional structures have been built. Further, in many previous examples of mechanosynthesis, there is a lack of separation of feedstock, presentation surface and workpiece (the presentation surface often serves as all three). And, the literature teaches only a small, non-generalizable set of tools and reactions, and uses atomically-imprecise tips, with no bootstrap process to facilitate the transition to atomically-precise tips. The computational literature contains other limitations. The literature is reviewed below with comments that will be helpful to not only understand the state of the art, but to distinguish it from the current invention.

Please note that none of the literature cited herein is admitted as prior art. In fact, while some of the literature is cited to put the current invention in context because it demonstrates other ways of creating simple workpieces, mechanosynthesis may not even employed, or the literature may not be analogous to the invention for other reasons.

Feedstock, Presentation Surface and Workpiece Terminology. Note that the literature frequently uses the same entity as the "feedstock," "presentation surface" and "workpiece." As a result, these items are frequently not distinguished in the literature as separate entities, nor are they necessarily referred to by the same names as used herein. This occurs when, for example, an atom is removed from a surface, and then placed back onto that same surface. In such an example, a portion of the top layer of the presentation surface is also the feedstock and the workpiece. This illustrates our point about mechanosynthesis being previously treated as a laboratory curiosity since it severely limits the versatility of the workpieces that can be manufactured, constraining the elements used in reactions and the workpieces to which they are applied, and solves none of the problems inherent in building more complex structures.

Previous Computational Simulations of Mechanosynthesis. Atomically-precise structures have been designed, and computationally examined. For example, see (Drexler, "Engines of Creation: The Coming Era of Nanotechnology," Anchor, 1987; Drexler, "Nanosystems: Molecular Machinery, Manufacturing, and Computation," New York, John Wiley & Sons, 1992). Computational techniques have also been used to design and validate mechanosynthetic reactions and tools (Mann, Peng et al., "Theoretical Analysis of Diamond Mechanosynthesis. Part II. C2 Mediated Growth of Diamond C(110) Surface via Si/Ge-Triadamantane Dimer Placement Tools," JOURNAL OF COMPUTATIONAL AND THEORETICAL NANOSCIENCE, 2004; Peng, Freitas et al., "Theoretical Analysis of Diamond Mechanosynthesis. Part I. Stability of C2 Mediated Growth of Nanocrystalline Diamond C(110) Surface," JOURNAL OF COMPUTATIONAL AND THEORETICAL NANOSCIENCE, 2004; Peng, Freitas et al., "Theoretical Analysis of Diamond Mechanosynthesis. Part III. Positional C2 Deposition on Diamond C(110) Surface using Si/Ge/Sn-based Dimer Placement Tools," J. Comput. Theor. Nanosci, 2006; Temelso, Sherrill et al., "High-level Ab Initio Studies of Hydrogen Abstraction from Prototype Hydrocarbon Systems," J. Phys. Chem. A, 2006; Temelso, Sherrill et al., "Ab Initio Thermochemistry of the Hydrogenation of Hydrocarbon Radicals Using Silicon, Germanium, Tin and Lead Substituted Methane and Isobutane," J. Phys. Chem. A 2007; Freitas and Merkle, "A Minimal Toolset for Positional Diamond Mechanosynthesis," Journal of Computational and Theoretical Nanoscience, 5, 2008; "Positional Diamondoid Mechanosynthesis" U.S. Pat. No. 8,171,568, 2009; Tarasov, Akberova et al., "Optimal Tooltip Trajectories in a Hydrogen Abstraction Tool Recharge Reaction Sequence for Positionally Controlled Diamond Mechanosynthesis," J. Comput. Theor. Nanosci., 2, 2010).

However, each of these references suffers from important limitations in terms of being able to actually manufacture a workpiece via mechanosynthesis (which is not a criticism per se, this was not the intent behind these investigations). Such limitations include insufficient simulation detail or accuracy (e.g., not describing the computations in a manner that makes them reproducible, or using unrealistically-low levels of theory which cannot be relied upon to provide reliable results), lack of a bootstrap sequence, lack of a comprehensive set of reactions and tips, lack of workpiece build sequences (or the means to create them), and others.

Literature is Surface-Based. In the literature mechanosynthesis is generally performed on, or to, a surface. For example, making and breaking of covalent bonds using mechanosynthesis via atomic force microscopy (AFM) was demonstrated for silicon atoms on a silicon surface. The AFM tip was used to remove, and re-deposit, Si atoms from the surface. (Oyabu, Custance et al., "Mechanical vertical manipulation of selected single atoms by soft nanoindentation using near contact atomic force microscopy," Phys. Rev. Lett., 17, 2003)

Subsequently, other demonstrations of mechanosynthesis have included manipulation of silicon atoms on a silicon/oxygen surface (Morita, Sugimoto et al., "Atom-selective imaging and mechanical atom manipulation using the non-contact atomic force microscope," J. Electron Microsc., 2, 2004), manipulation of germanium atoms on germanium surfaces (Oyabu, Custance et al., "Mechanical Vertical Manipulation of Single Atoms on the Ge(111)-c(2×8) Surface by Noncontact Atomic Force Microscopy," Seventh International Conference on non-contact Atomic Force Microscopy, Seattle, Wash., 2004), manipulation of polymers on silicon surfaces (Duwez, Cuenot et al., "Mechanochemistry: targeted delivery of single molecules," Nature Nanotechnology, 2, 2006), manipulation of silicon and tin atoms on a silicon surface (Sugimoto, Pou et al., "Complex Patterning by Vertical Interchange Atom Manipulation Using Atomic Force Microscopy," Science, 2008), and the creation of 1-dimensional copper wires on a copper surface (Lagoute, Liu et al., "Electronic properties of straight, kinked, and branchedCu/Cu(111)quantum wires: A low-temperature scanning tunneling microscopy and spectroscopy study," Physical Review B, 12, 2006).

Each of these references describe simple, surface-based 1 or 2-dimensional structures, made with a very limited number of reactions and feedstock, and only using very specific surfaces. They do not teach a generalizable way of creating atomically-precise workpieces.

Mechanosynthesis Tools in the Literature. Prior to (Freitas and Merkle, "Positional Diamondoid Mechanosynthesis" U.S. Pat. No. 8,171,568, 2009), few tools for mechanosynthesis had been described in the literature. Those that had been described include various high-level descriptions of possible mechanosynthesis reactions (Drexler, "Nanosystems: Molecular Machinery, Manufacturing, and Computation," New York, John Wiley & Sons, 1992), a hydrogen abstraction tool (Temelso, Sherrill et al., "High-level Ab Initio Studies of Hydrogen Abstraction from Prototype Hydrocarbon Systems," J. Phys. Chem. A, 2006), a hydrogen donation tool (Temelso, Sherrill et al., "Ab Initio Thermochemistry of the Hydrogenation of Hydrocarbon Radicals Using Silicon, Germanium, Tin and Lead Substituted Methane and Isobutane," J. Phys. Chem. A 2007), and dimer placement tools (Mann, Peng et al., "Theoretical Analysis of Diamond Mechanosynthesis. Part II. C2 Mediated Growth of Diamond C(110) Surface via Si/Ge-Triadamantane Dimer Placement Tools," JOURNAL OF COM- PUTATIONAL AND THEORETICAL NANOSCIENCE, 2004; Peng, Freitas et al., "Theoretical Analysis of Diamond Mechanosynthesis. Part I. Stability of C2 Mediated Growth of Nanocrystalline Diamond C(110) Surface," JOURNAL OF COMPUTATIONAL AND THEORETICAL NANOSCIENCE, 2004; Peng, Freitas et al., "Theoretical Analysis of Diamond Mechanosynthesis. Part III. Positional C2 Deposition on Diamond C(110) Surface using Si/Ge/Sn-based Dimer Placement Tools," J. Comput. Theor. Nanosci, 2006). Site-specific hydrogen abstraction was also demonstrated by (Hersam, Abeln et al., "An approach for efficiently locating and electrically contacting nanostructures fabricated via UHV-STM lithography on Si(100)," Microelectronic Engineering, 1999). Site-specific hydrogen donation was achieved experimentally by depositing hydrogen atoms onto a silicon surface by applying a voltage bias to a tungsten tip. (Huang and Yamamoto, "Physical mechanism of hydrogen deposition from a scanning tunneling microscopy tip," Appl. Phys. A, 1997)

(Freitas, "Simple tool for positional diamond mechanosynthesis, and its method of manufacture," U.S. Pat. No. 7,687,146, United States, 2010) purports to teach a tip for mechanosynthetic fabrication. However, the disclosed tip is limited to a very specific structure (a triadamantane base molecule with a dimer holder atom), performs only a single reaction (dimer deposition), and is constrained to working on a very specific surface ("having a melting point of at least 300° C., a thermal expansion coefficient maximally different than that of diamond, a mismatch in crystal lattice constant as compared to that of diamond, resistance to carbide formation, less bonding strength to the carbon dimer as compared to bonding strength between the diamond holder atom X and the carbon dimer, and little or no solubility or reaction with carbon.") This work does not teach a versatile or generalizable system of mechanosynthesis. Additionally, it is stated that "These analyses should be repeated using ab initio techniques, and should be extended to include a calculation of activation energy barriers (which could be substantial) . . . and solvent effects . . . " It would seem that the authors used a low level of theory in their simulations, ignored relevant chemical phenomenon, and actually do not know whether their invention works.

Subsequently, (Artyukhov, "A six degree of freedom nanomanipulator design based on carbon nanotube bundles," Nanotechnology, 38, 2010) described a carbon nanotube-based scheme for atomically-precise tips that can also provide positioning capability. Although various possibilities are discussed as to implementing such tips, there is little detail and no clear pathway to construction.

Among other drawbacks, none of the tools described in the literature, alone or in combination, could provide a bootstrap process, a set of tools exhibiting closure (that is, a set of tools that could build themselves), a versatile set of reactions, a set of reactions of known reliability at particular temperatures, nor were they directed to a system for three-dimensional fabrication.

Literature Conflates Feedstock, Feedstock Depot, and Workpiece. As exemplified by (Oyabu, Custance et al., "Mechanical vertical manipulation of selected single atoms by soft nanoindentation using near contact atomic force microscopy," Phys. Rev. Lett., 17, 2003; Oyabu, Custance et al., "Mechanical Vertical Manipulation of Single Atoms on the Ge(111)-c(2×8) Surface by Noncontact Atomic Force Microscopy," Seventh International Conference on non-contact Atomic Force Microscopy, Seattle, Wash., 2004), the literature frequently uses the local presentation surface itself as what if referred to herein as the feedstock depot, the feedstock, and the workpiece. For example, atoms are removed from the crystal structure of the presentation surface and then added back to a void in that same presentation surface. The atoms are not being removed from the surface to transport to a workpiece distinct from the presentation surface. In these types of experiments, the local presentation surface is the source of the feedstock and it is also the workpiece which is being altered by the mechanosynthetic reactions. In addition to the limitations which may be created by conflating the feedstock, feedstock depot, and workpiece, particularly when the presentation surface is, for example, pure Si or pure Ge (thus limiting the workpiece to a single element), filling a void with a single adatom is obviously not the same process as constructing a complex workpiece.

Literature Limited to One or Two Dimensions. The literature does not teach how to extend mechanosynthetically-created workpieces into three dimensions. Creating a three-dimensional structure using mechanosynthesis is not simply the extension or repetition of a one or two-dimensional motif. The bonding structure and build sequence must support extension into the third dimension through a sequence of reactions that is chemically and geometrically feasible without pathological rearrangement of intermediate products. This requires, among other things, designing build sequences which account for intermediate structures, and such strategies are not taught in the literature.

Literature Teaches a Very Small Number of Reactions per Workpiece. The literature is frequently limited to the removal of a single adatom (a surface atom), or the insertion of a single atom into a vacancy left by the removal of such an adatom. One of the most complex demonstrations of mechanosynthesis is that of (Sugimoto, Pou et al., "Complex Patterning by Vertical Interchange Atom Manipulation Using Atomic Force Microscopy," Science, 2008), who use vertical and lateral interchange to write the letters "Si" on an Sn surface. This appears to have taken about twelve total reactions, and four different types of reactions (vertical substitution of Si for Sn, vertical substitution of Sn for Si, lateral substitution of Si for Sn, and lateral substitution of Sn for Si). Other work may use more total reactions, but even less variety, for example, 18-atom copper lines are made in (Lagoute, Liu et al., "Electronic properties of straight, kinked, and branchedCu/Cu(111)quantum wires: A low-temperature scanning tunneling microscopy and spectroscopy study," Physical Review B, 12, 2006)

Literature Teaches Few Elements and Reaction Types. Very few elements and distinct reactions are used in the literature. For example, (Oyabu, Custance et al., "Mechanical vertical manipulation of selected single atoms by soft nanoindentation using near contact atomic force microscopy," Phys. Rev. Lett., 17, 2003; Oyabu, Custance et al., "Mechanical Vertical Manipulation of Single Atoms on the Ge(111)-c(2×8) Surface by Noncontact Atomic Force Microscopy," Seventh International Conference on non-contact Atomic Force Microscopy, Seattle, Wash., 2004) use either all Si atoms, or all Ge atoms, and then only in the context of a specific crystal structure (e.g., the 7×7 reconstruction on Si). There is no evidence that different intentional modifications to the presentation surface could have been made or that different crystallographic faces could have been used. (Sugimoto, Pou et al., "Complex Patterning by Vertical Interchange Atom Manipulation Using Atomic Force Microscopy," Science, 2008) uses four types of reactions (half of which are simply the reverse reactions of the other two), employing two elements.

As a point of reference for the number of elements and reactions, and the level of complexity of workpieces which have been built with similar techniques, (Ho and Lee, "Single bond formation and characterization with a scanning tunneling microscope," Science 286, 1999) use voltages rather than mechanosynthesis form Fe(CO), and then Fe(CO)2. Three elements and four reactions, only two of which are distinct, are used.

Literature Does Not Use Atomically-Precise Tips. The literature generally does not use atomically-precise tips (U.S. Pat. No. 7,687,146 is one exception that is discussed in detail herein). For example, the tip in (Oyabu, Custance et al., "Mechanical vertical manipulation of selected single atoms by soft nanoindentation using near contact atomic force microscopy," Phys. Rev. Lett., 17, 2003) is described as a "Si tip apex [that] was carefully cleaned up by argon-ion bombardment for 30 min." Such a process would result in a tip where the placement of individual atoms was unknown.

Literature Does Not Teach Varied Tips. When contemplating numerous reactions between various elements, to create varied structures, different tips can be used to facilitate the specific reactions desired. To the best of our knowledge the literature does not address this issue.

Literature Does Not Provide For Specific Levels of Reaction Accuracy. The accuracy of the mechanosynthetic reactions must be considered if one is to build workpieces with a known level of confidence. The mechanosynthesis literature generally does not address the issue of designing for reaction reliability. Some literature reports the reliability of a given reaction after the fact based on experimental results, but this is very different than engineering the system ahead of time so that the reactions achieve a desired level of accuracy. For example, (Sugimoto, Pou et al., "Complex Patterning by Vertical Interchange Atom Manipulation Using Atomic Force Microscopy," Science, 2008) provides computer modeling of a reaction barrier in rationalizing the observed behavior of their experimental system. But, this analysis is post-facto. They did not attempt to design a system ahead of time with a known level of reliability.

Further, as previously noted, the literature generally uses atomically-imprecise tips. Even where modeling is performed in the literature, modeling of an atomically-imprecise tip is unlikely to accurately represent the actual experimental system due to lack of knowledge of the exact structure of the tip. For example, the reaction modeling done in (Sugimoto, Pou et al., "Complex Patterning by Vertical Interchange Atom Manipulation Using Atomic Force Microscopy," Science, 2008) used a simplified tip structure which is almost certainly not the same structure that was actually used in the experiment.

Obviously, since the literature is not directed to a system with a planned level of reliability, neither does the literature investigate reaction reliability across a range of tips, elements, or conditions to teach a generalizable system for not only building workpieces, but building them with a known level of confidence.

Literature Not Using Individual Atoms or Molecules. The wording of the literature is not always clear as to when atoms are being referred to, versus some larger (and often indistinctly-defined) building block. Terminology used in the literature includes "cluster," "nanoparticle," "nanoscale object," "particle" and "nodule," among other terms. Regardless of the terminology used, work using imprecisely-defined building blocks is not an appropriate parallel to positioning, and making or breaking bonds, with atomic precision.

Perhaps even more confusing, literature exists which attempts to conflate atoms, molecules, and large, indistinct clusters of atoms. For example, (Ramachandran, Baur et al., "Direct and Controlled Manipulation of Nanometer-Sized Particles Using the Non-Contact Atomic Force Microscope," Nanotechnology, 9, 1998) defines "nanoscale objects" as essentially anything under one micron in diameter, including atoms, molecules, dendrimers, macro-molecules, viruses, phages, colloids, clusters, nanoparticles, nano-devices and other fabricated structures. [Col 6, Lines 61-67] Such a definition would include objects containing billions of atoms, where the placement of individual atoms is not known.

Clearly, mechanosynthesis cannot, at least in a planned manner that results in an atomically-precise workpiece, be performed using multi-atom structures in which the location of the constituent atoms is unknown.

Literature on Automated Mechanosynthesis. (Celotta, Balakirsky et al., "Invited Article: Autonomous assembly of atomically perfect nanostructures using a scanning tunneling microscope," Rev Sci Instrum, 12, 2014) describes the automated creation of two-dimensional structures. Chemistry is limited to an atomically-imprecise Iridium tip, and either Co atoms or CO molecules as feedstock, on a Cu(111) surface. "Path planning" is used, which is limited to two dimensions, and feedstock is dragged across the surface to its desired location, rather than being picked up and deposited, eliminating the possibility of building three dimensional structures. The nature of the bonds being formed is unclear; it seems likely that the feedstock atoms and resulting structures are physically adsorbed to the surface, not chemically bonded.

Summary of Mechanosynthesis-Based Literature

The literature teaches the ability to make and break bonds using a small set of elements, with a limited set of reactions, only to specific structures (such as the 7×7 reconstruction of Silicon, or other similarly-specific and limited environments), using only the top atomic layer of a presentation surface. Additionally, the experimental mechanosynthetic reactions found in the have not been engineered in advance for versatility or reliability. Reliability, while a minor issue when, for example, the goal is to simply interchange one atom for another on a surface, becomes important when the goal is to reliably build atomically-precise structures containing many atoms or requiring many reactions.

Another drawback of the literature is that the presentation surface also frequently serves as the feedstock depot, feedstock and workpiece, such as with the "vertical manipulation" literature, of which (Oyabu, Custance et al., "Mechanical vertical manipulation of selected single atoms by soft nanoindentation using near contact atomic force microscopy," Phys. Rev. Lett., 17, 2003; Oyabu, Custance et al., "Mechanical Vertical Manipulation of Single Atoms on the Ge(111)-c(2×8) Surface by Noncontact Atomic Force Microscopy," Seventh International Conference on non-contact Atomic Force Microscopy, Seattle, Wash., 2004) are representative. Without separating the presentation surface, feedstock and workpiece, the ability to create diverse structures can be limited.

Drawbacks are also created by the use of non-atomically-precise tips in the literature, and in some cases, unrealistically-low levels of theory in computational simulations. Further, the literature contains no teachings as to how one might generalize the mechanosynthetic techniques presented to other elements and reactions, or to construct complex, three-dimensional workpieces.

Overall, the literature is directed towards viewing mechanosynthesis as a very limited set of surface modifications, not as a generalizable set of concepts, tools, reactions and procedures designed for reliably building varied workpieces. The present invention addresses all of these issues, as will be seen from the detailed explanations and exemplary embodiments.

BRIEF SUMMARY OF THE INVENTION

The present invention is directed to processes for creating build sequences which are described using computational chemistry algorithms to simulate mechanosynthetic reactions, and which may use the mechanosynthesis process conditions or equipment limitations in these simulations, and which facilitate determining a set of mechanosynthetic reactions that will build an atomically-precise workpiece with a desired degree of reliability. Included are methods for error correction of pathological reactions or avoidance of pathological reactions. Libraries of reactions may be used to reduce simulation requirements.

BRIEF DESCRIPTION OF DRAWINGS

For a more complete understanding of the present invention, reference is now made to the following descriptions taken in conjunction with the accompanying drawings, in which.

DETAILED DESCRIPTION OF THE INVENTION

Definitions

Figure 1A:
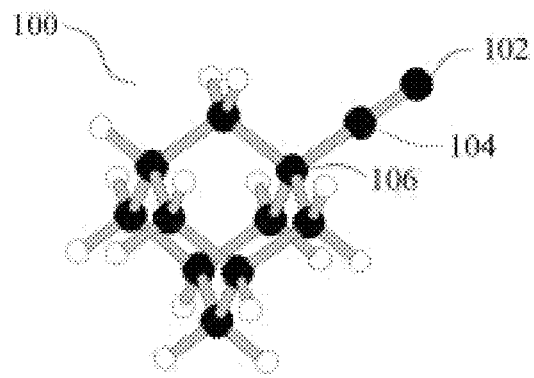
FIG. 1A is an active Hydrogen Abstraction Tool.

The following definitions are used herein:

An "adamantane" molecule comprises a 3D cage structure of ten carbon atoms, each terminated with one or two hydrogen atoms, having the chemical formula C10H16 and representing the smallest possible unit cage of crystalline diamond.

An "adamantane-like molecular structure" includes one or more adamantanes, one or more adamantanes where one or more atoms have been substituted with atoms of like or similar valence, including Nitrogen or Oxygen-substituted variations, and similar molecules comprising polycyclic or cage-like structures. By way of example, and not of limitation, an adamantane-like molecular structure would include adamantane, heteroadamantanes, polymantanes, cubane, iceane, pagodane, fullerenes, graphene, lonsdaleite, crystalline silicon or germanium, and versions of each of the foregoing where, for example, Fluorine is used for termination instead of Hydrogen, or where termination is incomplete.

An "atom" includes the standard use of the term, as well as a radical, which, for example, may be just a proton in the case of $H^+$.

"Atomically-precise" means where the position and identity of each atom is known to a precision adequate to enable a site-specific mechanosynthetic reaction.

The "bridgehead position" of an adamantane-like molecular structure refers to a structural atom that is bonded to three other structural atoms and may be terminated by one or more nonstructural atoms.

A "build sequence" is one or more mechanosynthetic reactions arranged in an ordered sequence that permits the assembly, disassembly, or modification of a workpiece.

A "chemical bond" is an interatomic covalent bond or an interatomic ionic bond, as these terms are commonly understood by practitioners skilled in the art.

A "chemical reaction" is said to occur when chemical bonds are formed or broken, or when the directionality, strength, or other material characteristics of an existing chemical bond is altered, as for example during positionally controlled bond bending, stretching, or compression.

A "coaxial" reaction or trajectory is one in which the bond broken and the bond formed lie on the same line.

"Diamond" is a crystal of repeating adamantane cage units arranged in various well-known crystallographic lattice geometries.

"Diamondoid" materials include any stiff covalent solid that is similar to diamond in strength, chemical inertness, or other important material properties, and possesses a three-dimensional network of bonds. Examples of such materials include but are not limited to (1) diamond, including cubic and hexagonal lattices and all primary and vicinal crystallographic surfaces thereof, (2) carbon nanotubes, fullerenes, and other graphene structures, (3) several strong covalent ceramics of which silicon carbide, silicon nitride, and boron nitride are representative, (4) a few very stiff ionic ceramics of which sapphire (monocrystalline aluminum oxide) is representative, and (5) partially substituted variants of the above that are well-known to those skilled in the art.

"Feedstock" is the supply of atoms used to perform mechanosynthetic reactions on a workpiece. Feedstock may take the form of an atom or atoms (a group or molecule), including radicals (e.g., .GeH2, .CH2).

A "handle structure" comprises a plurality of atoms whose bonding pattern or electronic state is not altered during a site-specific mechanosynthetic chemical reaction and whose primary function is to hold a mechanosynthetically active tip or tool in a fixed geometric relationship that will permit a mechanosynthetic chemical reaction to proceed when the handle is manipulated by a positional device. Handle structure may include the null case.

An "inert environment" includes, but is not limited to, UHV, helium, neon, or other noble gases either individually or in combination, or other gases or liquids that do not react with the tip, feedstock, or workpiece during mechanosynthetic operations.

"Mechanical force" may include applied mechanical forces having positive, negative, or zero magnitude. Chemical reactions driven by the application of mechanical force include reactions that are (1) driven through its reaction barrier by mechanically forcing reactants or products through the transition state, or (2) driven away from an undesired reaction by mechanically restraining potentially reactive sites from attaining closer physical proximity, or (3) allowed to occur by bringing potentially reactive sites into closer physical proximity when zero mechanical force is required to do so, as for example when no reaction barrier exists.

"Mechanosynthesis" is the use of positional control and mechanical force to facilitate one or more site-specific chemical reactions involved in the creation of a workpiece. The use of voltage biases combined with mechanical force-based mechanosynthesis is not required, but is included in the definition of mechanosynthesis.

A "mechanosynthetically active tip" is a tip controlled by a positional device that can perform mechanosynthetic reactions.

A "mechanosynthetic reaction" (sometimes referred to as a "reaction" when context makes it clear that the reaction is mechanosynthetic) is a chemical reaction carried out using mechanosynthesis.

A "positional device" is a device capable of exerting atomically-precise positional control on a mechanosynthetic tip, tool, or workpiece, and may include, but is not limited to, a conventional scanning probe microscope (SPM) such as an atomic force microscope (AFM), a miniaturized or MEMS-scale SPM or AFM, a robotic arm mechanism of any size scale, or other appropriate manipulation system capable of atomically-precise positional control.

A "pathological side reaction" is an undesired reaction which may happen in the course of mechanosynthesis, such as bonding feedstock to the wrong atom on a workpiece, or a rearrangement of atoms on a workpiece due to instability of an intermediate structure during a build sequence. A "pathological side reaction" is not an inherent property of the reaction, but is rather relative to the specific objectives of the reaction. Two identical build sequences with different objectives might result in the same chemical reaction which, in one case, is labeled a "pathological side reaction", but in the other case is a desired outcome.

The "sidewall position" of an adamantane-like molecular structure refers to a structural atom that is bonded to two other structural atoms and is terminated by one or more nonstructural atoms.

"Site-specific" refers to knowing, and being able to constrain, with a desired degree of reliability, the position on a chemical structure at which a mechanosynthetic reaction takes place.

A "structural atom" in an adamantane-like molecular structure refers to an atom comprising the cage framework, for example a carbon atom in an adamantane molecule. More generally, a structural atom is an atom that comprises part of the backbone or overall structure in a highly-bonded molecule.

A "terminating atom" refers to an atom that does not serve as a structural atom but absorbs unused valences of a structural atom. For example, a hydrogen atom in an adamantane molecule.

A "three-dimensional" workpiece means a workpiece including a lattice of atoms whose covalent structure necessarily occupies three dimensions, considering atoms as points, and discounting torsion angles. Under this definition, for example, proteins would be two dimensional, as would a plane of graphene. A covalent network solid or a carbon nanotube would be three-dimensional.

A "tool" is a mechanosynthetically active tip bonded to a handle structure.

A "tip" is a device for facilitating mechanosynthetic reactions which includes one or more "active" atoms whose bonding pattern or electronic state is altered during a mechanosynthetic operation, and one or more "support" atoms whose bonding pattern or electronic state is not altered during a mechanosynthetic operation. The support atoms function to hold the active atoms in position. A tip may be atomically-precise or imprecise. Note that multi-tip microscopy devices are well-known and may also be applied to the present invention.

For example, force may be applied, bonds formed, or potential energy landscapes adjusted, using more than one tip simultaneously to, e.g., stabilize an intermediate workpiece structure during or between reactions, or to facilitate a reaction that is otherwise problematic using only one tip.

A "tool" is a mechanosynthetically active tip bonded to a handle structure.

A "toolset" is a selected set of tools.

A "trajectory" is the path a tip follows through space to facilitate a desired mechanosynthetic reaction.

A "workpiece" is an apparatus, article of manufacture, or composition of matter, built via mechanosynthesis. A system may have more than one workpiece. A workpiece may be connected to, but does not include, other structures that were not created via mechanosynthesis, such as a support substrates, feedstock depots, or tethered pre-existing structures.

Chemical Structure and Scientific Notation. A dot (".") is frequently used in chemical structures herein to represent an electron, as in the radical group ".CH2". For ease of typesetting, the notation herein generally omits subscript or non-standard characters as its meaning is still clear and unambiguous. Superscript may be written using the "^" character when required for clarity.

Applications of the Invention

The invention may be used to fabricate atomically-precise, multi-atom structures. The present invention has many advantages, including the ability to fabricate complex structures to atomically-precise specifications, the ability to position individual atoms or groups of atoms in specific locations on a workpiece, the ability to remove specific groups of atoms from specific sites on a workpiece, the ability to make atomically-precise modifications to a workpiece, the ability to make specific sites on a workpiece become reactive while the rest of the workpiece remains relatively unreactive, and the ability to make specific sites on a workpiece become unreactive.

The particular tools, tips, reactions, build sequence and other teachings herein are embodiments of the invention and should not be construed to limit the invention to only the disclosed embodiments. The teachings herein readily extend the invention to a wider range of tools, tips, reactions, elements, structures and conditions.

Feedstock and Presentation Surfaces

Mechanosynthesis requires a source of atoms on which to perform reactions. These atoms are referred to as feedstock, and to the location at which these atoms are stored as the feedstock depot. Feedstock may reside on a presentation surface, or be provided in other ways, such as in liquid or gas form, as a bulk solid rather than just a surface layer, or feedstock could be already attached to a tip.

Assuming the use of a feedstock depot (e.g., a surface comprised of, or coated, with the desired atoms or molecules), a tip under positional control can be brought to the feedstock depot and bonded to feedstock, allowing the tip to remove the feedstock from the feedstock depot and carry it away to participate in mechanosynthetic operations, (e.g., to add one or more atoms to a specific site on a workpiece).

If the feedstock is being supplied from a presentation surface, that feedstock must somehow be attached to the presentation surface. Methods for coating surfaces with atoms or molecules are well-known in the literature. Substantial theoretical work exists, including a generalized method for depositing hydride gasses (e.g., $SiH_4$, $GeH_4$, $NH_3$, $PH_3$, $CH_4$, and $SiH_3CH_3$) onto Si or Ge surfaces. See (Murota, Sakuraba et al., "Atomically Controlled Processing for Group IV Semiconductors by Chemical Vapor Deposition," Japanese Journal of Applied Physics, Part 1, Number 9A, 2006), the content of which we incorporate by reference. Also, the integrated circuit industry, and other industries such as solar cell manufacture, rely upon the deposition of many substances, frequently in monolayer form, onto crystalline wafers. These wafers are made of materials such as CdSe, CdTe, CdHgTe, GaAs, GaN, Ge, Si, SiC, $SiO_2$, $Si_3N_4$ and ZnS.

In addition to using feedstock taken from a surface coating, feedstock could also be taken from a bulk material. For example, an uncoated wafer surface could supply any of the atoms present in the wafer itself. Consequently, between coatings and bulk materials, every important element is available, often commercially, but if not, other elements can be incorporated onto a surface, or into a bulk material, using well known techniques such as physical vapor deposition (PVD), Atomic Layer CVD (ALCVD), laser CVD, direct ion beam deposition, dual ion beam sputtering, electroplating, RF/DC glow discharge, microwave discharge, and spin coating. It should also be noted that a presentation surface may provide more than one type of feedstock. Different feedstock could be placed in different sectors of the presentation surface, layered on top of each other (e.g., via ALCVD), multiple bulk materials could be present, or a bulk material could be heterogeneous, supplying multiple elements.

There is a distinction to be made between physical adsorption and chemisorption (involving the formation of a new chemical bond). In general, feedstock could be bonded to a presentation surface in either manner. Depending on the reactivity of the feedstock relative to a given surface, a surface that chemisorbs one type of feedstock may physically adsorb another, although there are surfaces that tend to allow primarily physical adsorption, such as a frozen noble gas. Frozen noble gases are used both as a surface and a matrix (that is, throughout its bulk) for trapping small molecules, and are not the only set of fairly unreactive gases or compounds which could be used in this manner. For example, $SiF_4$ may serve in a similar capacity, as might fluorinated polymers.

In the case of reactions where little or no force need be applied to the tip to facilitate bonding the feedstock, physical adsorption may offer the advantage of ease of removal of the feedstock from the surface, while in cases where there is a barrier to bonding the feedstock to the tip, a covalent bond may be useful to prevent the feedstock from migrating on the presentation surface when force is applied. Covalent bonding may also be useful at higher temperatures that would permit migration or desorption of physically adsorbed feedstock. One will frequently want the presentation surface to feedstock bond to be weaker than the tip to feedstock bond to facilitate transferring the feedstock to a workpiece, and in addition to choosing presentation surfaces for their elemental content, it will be obvious to those skilled in the art that presentation surfaces can be chosen with bond energy in mind (although techniques such as voltage biases and other methods for adjusting tip-feedstock bond strength, such as inducing strain in one or more bonds, mean that a lower-energy bond with the presentation surface is not always required).

Reliability

Reliability is an important consideration in the design of build sequences for multi-atom workpieces. While some imperfections in a workpiece may be tolerable, all other things being equal, the higher the number of atoms in the workpiece, the greater the need for reliability. Reaction reliability can be achieved in a variety of ways, including use of reactions with energy barriers sufficient to prevent spontaneous reactions at a given temperature, reactions designed to avoid pathological side reactions (for example, by approaching a workpiece using a trajectory that favors only the desired reaction, or by ordering a build sequence to avoid leaving unsatisfied valences in dangerous positions), or the introduction of a testing step during mechanosynthesis. These topics are discussed in more detail below.

In some cases, primarily with respect to hydrogen due to its low atomic mass, tunneling can contribute to reaction error. These errors can be reduced with slight modifications in build sequences to avoid problematic situations. Also, one could use deuterium in place of standard hydrogen. Deuterium's different mass and Van der Waal's radius also has effects on reaction rates (the kinetic isotope effect), vibrational frequencies, torsional coupling and other properties. All of these effects may be exploited by choosing to use hydrogen or deuterium on a case by case basis. Note that in general, any isotope of an element could be used where its properties are advantageous, and the ability to positionally control isotopes of an element may useful, just as the positional control of different elements is useful.

Reaction Barriers and Temperature. Note that equipment capabilities could have an effect on reaction reliability. For example, the error in a positional means is unlikely to be zero. However, it is well within the limits of conventional atomic microscopy technology to attain high enough positional accuracy that it essentially becomes irrelevant. With equipment that can position one or more tips to, e.g., <20 pm, temperature becomes the dominating variable in reaction reliability. As the positional means become less accurate, reaction reliability suffers regardless of temperature, and for example, positional errors of 50 pm or more will substantially degrade reaction reliability. Those skilled in the art will understand how to incorporate such equipment limitations into reaction reliability calculations, if necessary. For exemplary purposes, only temperature is considered in the following example of calculating reaction reliability.

One of the advantages of mechanosynthesis is that it facilitates specific, desired reactions by using directed mechanical force to overcome reaction barriers. In conventional chemistry, reaction barriers or energy deltas are often overcome by thermal energy. However, thermal energy is nonspecific and facilitates desired and undesired reactions alike. Reducing temperature decreases the thermal energy available to cause non-specific reactions. This reduces the likelihood of pathological side reactions while directed mechanical force, even at low temperatures, still facilitates desired reactions.

The Arrhenius equation and other principles of thermodynamics and computational chemistry may be used in conjunction with data on net energy differences and energy barriers to determine the reliability of a given reaction at a given temperature. For example, the following Mathematica version 8 code may be used to determine reaction reliability at a given temperature when considering the net energy difference between two structures (e.g., the before and after workpiece structures):

```
Code Listing 1:
(** calculate reliability of a reaction at a given temperature **)
(** Define Constants and Unit Conversions **)
    (** Boltzmann constant = 1.38*10^-23 J/K **)
    boltzmann = 1.381*10^-23;
    (** convert eV to Joules **)
    jouleBarrier = barrier*1.6*10^-19;
(** inputs for specific reaction **)
    (** reaction barrier in eV **)
    barrier = Abs[-0.6418];
    (** temp in Kelvin **)
    temperature = 300;
(** Calculate Probability of Failure **)
probability = NumberForm[Exp[-jouleBarrier/(boltzmann*temperature)], 4]
```

Reliability in Build Sequences. The reliability of reactions across a build sequence can provide one way of assessing the statistical error rate. And, depending on which, or how many, errors are considered significant enough to compromise workpiece function, these data can then be used to assess workpiece yield (or performance, in a scenario where workpieces do not simply pass/fail a quality check and the effect of certain errors on workpiece function are known) in a manufacturing setting. This is most easily explained by example.

Consider a workpiece which requires $10^6$ reactions to create. For the sake of simplicity, assume that each of these reactions are identical in their energy barrier to a pathological reaction (an error), and that the barrier is 0.2 eV. Another assumption is that simulations, practical experience, or other information provide guidelines as to how many errors, on average, may be present before a workpiece is deemed defective. Arbitrarily, since this would vary with the workpiece design, a limit of 10 errors is used for this example. Which is to say, a workpiece having between 0 and 10 errors is acceptable, while a workpiece having over 10 errors will be rejected as defective. Finally, (again, arbitrarily to demonstrate the logic, since this number will vary depending on the business and technical requirements) a yield of at least 90% is required.

Since an error is presumed to be a rare event, error occurrence is modeled as a Poisson distribution. The problem then becomes one of determining X, the number of expected events, where the Cumulative Distribution Function is equal to or greater than 0.90 (a 90% yield) when the number of events is 10 (the maximum number of tolerable errors). In this case, $\lambda$ is 7. Meaning, if one expects, on average, that 7 errors will occur during the build sequence, then 90% of the time, no more than 10 events will occur. So, the expected number of errors must be<=7. Since the hypothetical workpiece requires $10^6$ reactions to build, the threshold for mistakes is $7/10^6$.

So, the accuracy requirements are that error rate that does not exceed $7/10^6$ when the reaction barriers are 0.2 eV. Using the equations herein to solve for the maximum allowable temperature to attain this accuracy, the answer happens to be about 195 degrees Kelvin, although obviously this number can change depending on actual reaction barriers, manufacturing requirements, equipment capabilities, and other factors.

Note that these calculations assume that temperature is the sole factor limiting reliability. As previously noted, there may be other sources of error, caused by factors such as positional uncertainty in the equipment, or Hydrogen tunneling, and these could be factored in when assessing an actual manufacturing process. Also, note the assumption that errors are statistically independent. Error independence is unlikely in some scenarios, since a missing or mis-bonded atom may cause subsequent problems when placing neighboring atoms. However, this is not necessarily the case, nor is it a concern if one decides to strive for a 0% error rate. If the requirement was zero errors, this consideration disappears since, if an error occurred, it would either be fixed, or the workpiece would be scrapped and the manufacturing process would start over.

Temperature and reaction barriers aside, considering the simple statistics of the case where zero errors is the requirement provides a way to compare the literature processes to the reliability requirements needed for complex manufacturing tasks. The literature often describes experiments involving between one and about twelve reactions. The literature does not report error rates, but theoretically, how reliable must the reactions be to perform, for example, twelve reactions with no errors? A simple calculation (Reliability $^{\#Reactions}$=Yield) shows that 95% reliability would give a 54% yield. That may be an acceptable, or even excellent, yield for a laboratory process.

But, what if the workpiece, rather than requiring 12 reactions, requires 50 reactions? Then at 95% reliability, the yield is 7.7%. By 100 reactions the yield is under 1%, and substantially beyond 100 reactions, reliability must be increased or the yield becomes minuscule. For example, to achieve a yield of 50% with a workpiece that requires 1,000 reactions, reliability must be 99.93%, and to achieve the same yield with a workpiece requiring 1,000,000 reactions, reliability must be 99.99993%.

Clearly, error rates that are acceptable for workpieces requiring trivial numbers of reactions are untenable for building more complex workpieces. Of course, this statement comes with a number of assumptions, such as no error correction processes, and little tolerance for errors in the finished workpiece. But, in general, this illustrates the need for rationally-designed build sequences, based on reactions of known reliability, that permit reliability far in excess of that evidenced in the literature (but well within the capabilities of the reactions reported herein).

Testing for Reaction Success. The most basic mechanosynthesis process involves performing a reaction with the assumption that the desired reaction took place as expected. This may be a reasonable assumption since reactions can be engineered to have high degrees of reliability. However, it is possible to obtain information on what reaction actually occurred or what structure resulted. For example, AFM or STM techniques can be used to scan the workpiece after a reaction. If an undesired reaction occurred, various actions can be taken such as simply noting the error if it is not critical to the workpiece function, fixing the error, revising the subsequent reactions to account for the error, or discarding the workpiece and starting over.

Overview of the Bootstrap Tools and Reactions

The present invention provides a pathway for the creation of a set of mechanosynthetic molecular tools that are able to fabricate the self-same set, refresh all tools in the set, allow for numerous reactions using many elements, and create diverse workpieces, including many-atom, three dimensional structures. A set of mechanosynthetic tools is described that achieves all these objectives, as is a bootstrap process to build the first set of such tools.

While some of these mechanosynthetic tools have been analyzed in the literature, no complete set of tools has been described which are able to fabricate a wide variety of complex structures, including themselves, with a bootstrap sequence to allow the creation of the first set of tools.

The set of mechanosynthetic molecular tools comprises: (1) the Hydrogen Abstraction Tool, shown in FIG. 1; (2) the Hydrogen Donation Tool, shown in FIG. 2; (3) the Germanium Radical Tool, shown in FIG. 3; (4) the Methylene Tool, shown in FIG. 4; (5) the GermylMethylene Tool, shown in FIG. 5; (6) the Germylene Tool, shown in FIG. 6; (7) the Hydrogen Transfer Tool, shown in FIG. 7; (8) the Adamantane Radical Tool, shown in FIG. 8; and (9) the Dimer Placement Tool, shown in FIG. 9.

This specific set of tools has the ability to fabricate and refresh (charge or discharge a tool, as needed) all the tools in the toolset as well as the ability to make a range of other products (in this case, a wide range of structures composed of hydrogen, carbon and germanium). In the following description, the fabrication of more molecular tools, given a sufficient number of each initial type of molecular tool, is described. Also described is how to recharge the molecular tools, and how to use the molecular tools to fabricate other molecular structures.

Note that while the initial tool set created by the bootstrap sequence is targeted at hydrocarbon and germanium structures, subsequently, numerous other tip structures are described herein which expand substantially on the kinds of atoms which can be transferred, and it should be understood that other tip and tools would be apparent to one skilled in the art and having the benefit of the teachings presented herein.

Tool Details

The nine principal tools have been listed above. A detailed description of these tools follows. For clarity, all figures show the active atoms of each tip for a given tool, and some supporting atoms but do not show the handle structure that is attached to each tip to make the complete tool. This is because the handle structure can be much larger than the tip and the site of mechanosynthetic chemical activity is the tip, not the handle. Understand that while a handle may not be shown, it is assumed to exist when necessary for positioning the tools with the necessary precision.

All atomically-precise tools and mechanosynthetic reactions described have been analyzed at high levels of accuracy, using supercomputers and/or parallel processing. Generally, coarse structure determination was done using molecular mechanics methods, and these designs were subsequently refined using Density Functional Theory (DFT) methods. Thousands of tool structures, reactions, and build sequences have been examined, using millions of CPU hours (where a "CPU" is equivalent to a 3 GHz standard processor).

In more detail, the bootstrap tools are:

(1) The Hydrogen Abstraction Tool. FIG. 1A illustrates the active tip of the Hydrogen Abstraction Tool 100 which is used to selectively abstract a single hydrogen atom from a workpiece. Hydrogen Abstraction Tool 100 is shown prior to the abstraction of a hydrogen atom. The distal carbon atom 102 is a radical with a high affinity for hydrogen. Carbon atoms 102 and 104 are triply bonded to each other and in this and other structures are commonly referred to as "an ethynyl radical" or a "dimer." The ethynyl radical is bonded to carbon atom 106, called a "bridgehead" carbon atom. The remainder of the adamantane cage consists of 10 carbon atoms and the hydrogen atoms which terminate them.

In general use, the 6 carbon atoms at the base of the adamantane cage (i.e., the six carbon atoms in the adamantane cage most distant from carbon atom 106 in FIG. 1A) are bonded to a handle structure by which the tool is positioned. The Hydrogen Abstraction Tool is used by positioning the tool so that carbon atom 102 is in close proximity (e.g., one or two angstroms) to a hydrogen atom which is to be abstracted. When the Hydrogen Abstraction Tool is so positioned, the selected hydrogen atom will bond more strongly to carbon atom 102 than to almost any other molecular structure and hence will transfer from that other structure to carbon atom 102. The Hydrogen Abstraction Tool 100 following a hydrogen abstraction will appear as a spent Hydrogen Abstraction Tool 110 shown in FIG. 1B, where the abstracted hydrogen 112 is shown bonded to carbon atom 102.

Figure 2:
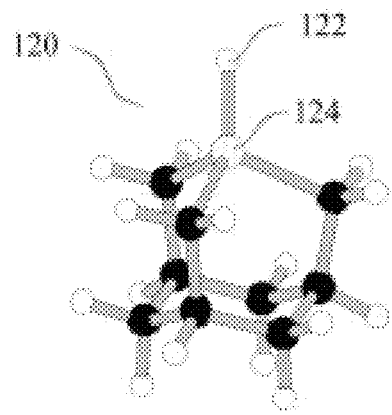
FIG. 2 is a Hydrogen Donation Tool.

(2) The Hydrogen Donation Tool. FIG. 2 illustrates the Hydrogen Donation Tool 120. The hydrogen atom 122 is bonded to germanium atom 124. Because the bond between germanium atom 124 and hydrogen atom 122 is not as strong as the bond that can be formed between hydrogen atom 122 and a carbon radical on a workpiece, the hydrogen atom 122 will, when positioned close to a carbon radical and with the application of mechanical force to overcome reaction barriers, transfer to that carbon radical and so donate a hydrogen to it.

Figure 3:
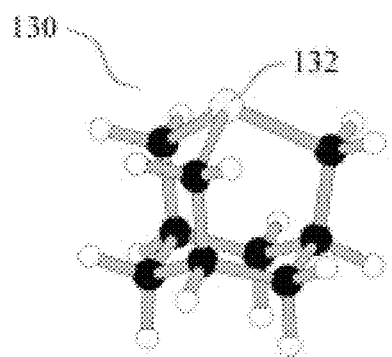
FIG. 3 is a Germanium Radical Tool.

(3) The Germanium Radical Tool. FIG. 3 illustrates the Germanium Radical Tool 130. The germanium atom 132 is a radical. The Germanium Radical Tool 130 results from the reaction that will occur when the Hydrogen Donation Tool 120 donates hydrogen atom 122 to a carbon radical.

Figure 4:
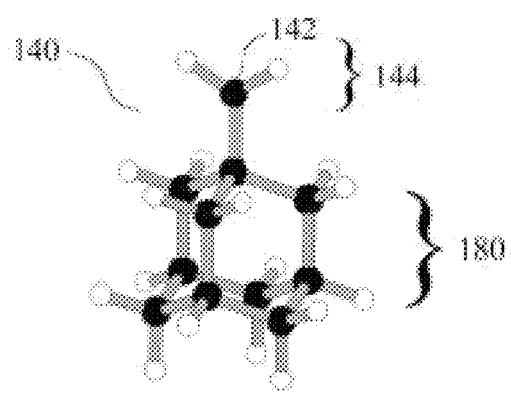
FIG. 4 is a Methylene Tool.

(4) The Methylene Tool. FIG. 4 illustrates the Methylene Tool 140. The Methylene Tool is formed by adding a .CH2 group 144 to the Adamantane Radical Tool 180. The carbon atom 142 in .CH2 group 144 is highly reactive because it is a radical.

Figure 5:
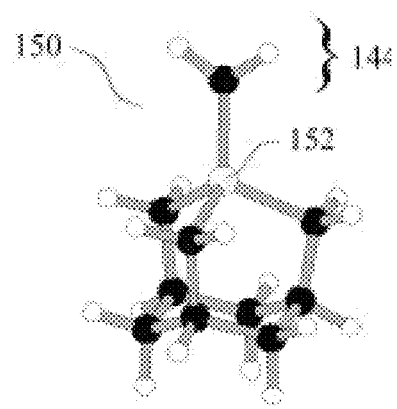
FIG. 5 is a GermylMethylene Tool.

(5) The GermylMethylene Tool. FIG. 5 illustrates the GermylMethylene Tool 150. Because the bond between .CH2 group 144 and germanium atom 152 is relatively weak, the GermylMethylene tool can be used to transfer the .CH2 group 144 to a carbon radical site on a growing workpiece.

Figure 6:
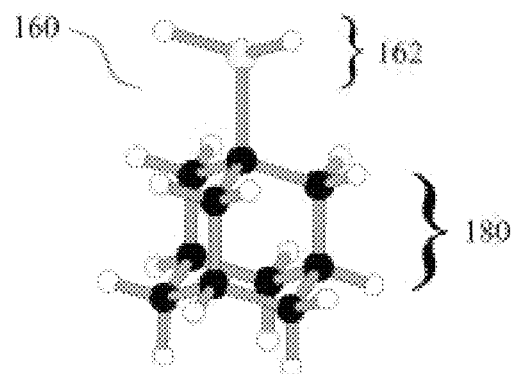
FIG. 6 is a Germylene Tool.

(6) The Germylene Tool. FIG. 6 illustrates the Germylene Tool 160 which can be formed by adding a .GeH2 group 162 to the Adamantane Radical Tool 180. Germylene Tool 160 can be used in build sequences that add a germanium atom to a workpiece (and in particular, can be used during the synthesis of the Germanium Radical Tool 130).

Figure 7:
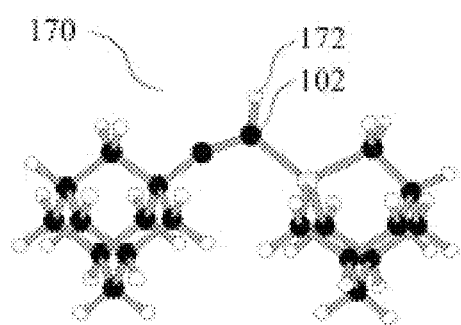
FIG. 7 is a Hydrogen Transfer Tool.

(7) The Hydrogen Transfer Tool. FIG. 7 illustrates the Hydrogen Transfer Tool 170 which can be formed by the reaction shown in FIG. 12A. The Hydrogen Transfer Tool is particularly useful because the bond between carbon atom 102 and hydrogen atom 172 is particularly weak, making it an excellent hydrogen donation tool.

Figure 8:
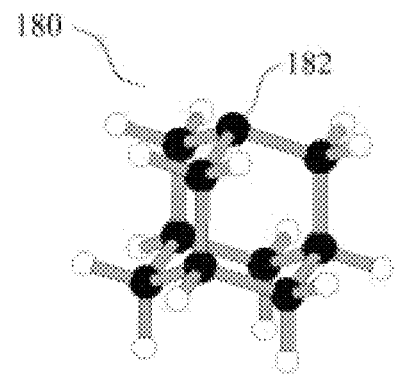
FIG. 8 is an Adamantane Radical Tool.

(8) The Adamantane Radical Tool. FIG. 8 illustrates the Adamantane Radical Tool 180 which can be formed by abstracting a hydrogen atom from an exposed adamantane cage on any diamond surface located, e.g., at the terminus of a tip, producing a single carbon radical 182.

Figure 9:
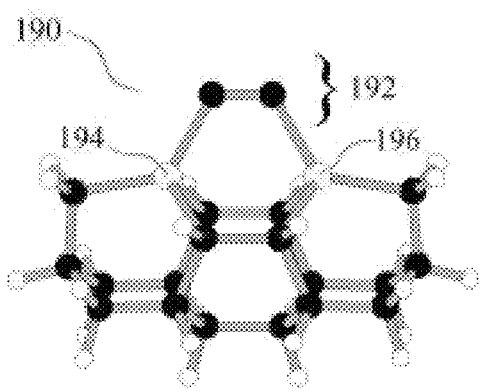
FIG. 9 is a Dimer Placement Tool.

(9) The Dimer Placement Tool. FIG. 9 illustrates the Dimer Placement Tool 190 in which a dimer 192 bonds to a tip which has two germanium atoms 194 and 196. The two bonds between the dimer 192 and the two germanium atoms 194 and 196 are highly strained, making the resulting Dimer Placement Tool 190 reactive and suitable for adding a dimer to a growing workpiece, particularly when two adjacent radical sites are present on the workpiece to which the dimer can bond.

Use of the Tools

These nine tools are used in an inert environment (e.g., ultra-high vacuum, a pressure of 10^-9 Torr (10^-12 atm) or less) and require that some suitable positional device be used to position the tools with high accuracy. In addition, there must be a source of feedstock to provide the needed hydrogen, carbon and germanium atoms and optionally a sink for discard atoms if there is excess hydrogen.

One way to provide hydrogen is from a presentation surface covered by hydrogen atoms (e.g., a bulk produced flat hydrogenated diamond surface). One way to provide carbon is in the form of .CH2 groups distributed on a suitable presentation surface (e.g., on a bulk produced flat germanium surface). This also provides hydrogen, which may eliminate the need for an independent source for hydrogen. One way to provide germanium is in the form of .GeH2 groups distributed on a suitable presentation surface (e.g., on a bulk produced flat germanium surface). Both carbon and germanium can also enter the system when provided as methyl or germyl groups (CH3 or GeH3) on a suitable presentation surface. In this case, they can be made chemically active by abstracting a hydrogen atom and converting them into .CH2 or .GeH2 groups respectively.

Excess hydrogen must be removed if, for example, the product structure being built has fewer hydrogen atoms than are present in the feedstock, in which case, e.g., the excess hydrogen atoms provided by the .CH2 groups must be disposed of One way of doing this is to provide a surface to which the Hydrogen Donation Tool can donate hydrogen atoms. One such surface would be a bulk-produced atomically flat non-hydrogenated diamond surface.

These nine tools are used to carry out the various reactions needed to recharge themselves, to fabricate more tools, and to make other atomically-precise structures (products).

Hydrogen Abstraction

Figure 10A:
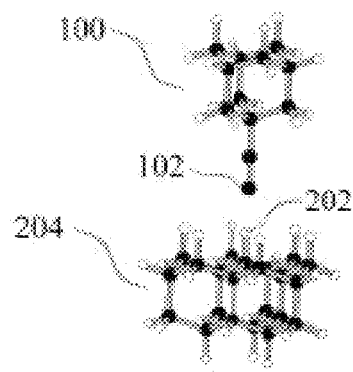
FIG. 10A shows a Hydrogen Abstraction Tool selectively abstracting a hydrogen atom.

FIG. 10A illustrates the use of the Hydrogen Abstraction Tool 100 to selectively abstract hydrogen atom 202. Hydrogen Abstraction Tool 100 is positioned so that radical carbon atom 102 is just above hydrogen atom 202 which is bonded to diamond surface 204. When Hydrogen Abstraction Tool 100 is brought into close proximity to diamond surface 204, the hydrogen atom 202 will bond to carbon atom 102, and thus transfer from diamond surface 204 to Hydrogen Abstraction Tool 100.

Figure 10B:
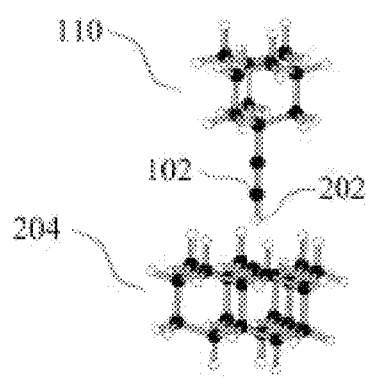
FIG. 10B shows abstraction in the transfer of a hydrogen atom and conversion to a spent Hydrogen Abstraction Tool.

FIG. 10B illustrates the result of the transfer of the hydrogen atom 202 to the Hydrogen Abstraction Tool 100 which serves to convert the Hydrogen Abstraction Tool 100 into a spent Hydrogen Abstraction Tool 110.

Hydrogen Donation

In one embodiment, a build sequence transfers a hydrogen atom from a Hydrogen Donation Tool to a diamond surface, both hydrogenating the radical site on the diamond surface and converting the Hydrogen Donation Tool to a Germanium Radical tool.

Figure 11A:
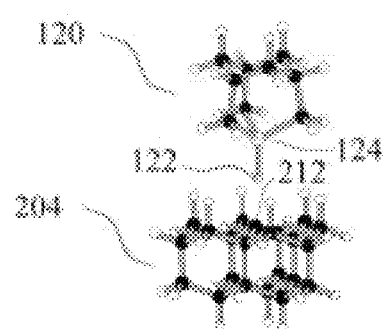
FIG. 11A shows a Hydrogen Donation Tool selectively donating a hydrogen atom.

FIG. 11A illustrates the use of the Hydrogen Donation Tool 120 to selectively donate one hydrogen 122 atom to carbon radical 212 on diamond surface 204. The Hydrogen Donation Tool 120 can be positioned directly above diamond surface 204 proximally close to carbon radical 212. When Hydrogen Donation Tool 120 is brought into close proximity to diamond surface 204 such that the attractive force between hydrogen atom 122 and carbon radical 212 exceeds the attractive force between the hydrogen atom 122 and the germanium atom 124, the hydrogen atom 122 will transfer from the germanium atom 124 and bond to the diamond surface 204 at the site of the carbon radical 212.

Figure 11B:
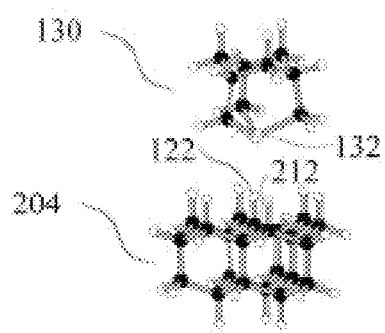
FIG. 11B shows the donation of a hydrogen atom and conversion to a Germanium Radical Tool.

FIG. 11B illustrates the result of the transfer of the hydrogen atom 122 to carbon atom 212 (now no longer a radical), which serves to convert the Hydrogen Donation Tool 120 into a Germanium Radical Tool 130 now having a germanium radical 132.

Recharge of Hydrogen Abstraction and Hydrogen Donation Tools

In one embodiment, a build sequence refreshes a Hydrogen Abstraction Tool by transferring a hydrogen atom from a spent Hydrogen Abstraction Tool to a Germanium Radical Tool.

Figure 12A:
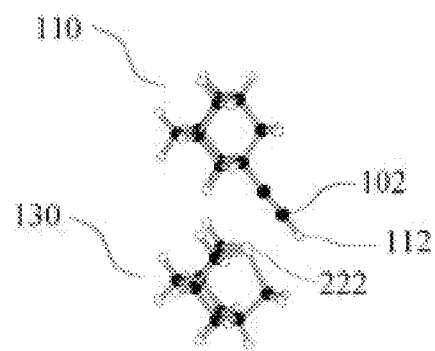
FIG. 12A shows a Germanium Radical Tool bonding to a spent Hydrogen Abstraction Tool.

FIG. 12A illustrates a Germanium Radical Tool 130 and a spent Hydrogen Abstraction Tool 110 with distal carbon atom 102 bonded to hydrogen atom 112. The spent Hydrogen Abstraction Tool is then brought into proximity to the Germanium Radical Tool 130 so that germanium radical 222 bonds to carbon atom 102 of spent Hydrogen Abstraction Tool 110. The result of the reaction is illustrated in FIG. 12B.

Figure 12B:
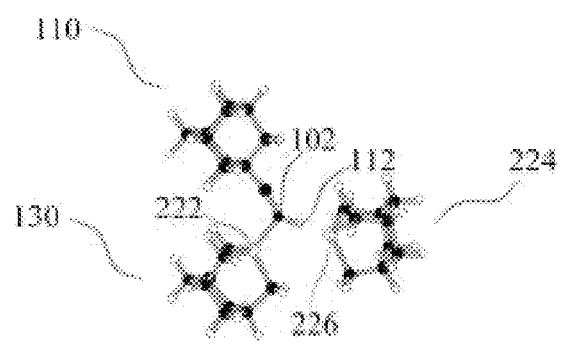
FIG. 12B shows a Germanium Radical Tool weakly bonded to a spent Hydrogen Abstraction Tool.

FIG. 12B illustrates the germanium radical 222 of the Germanium Radical Tool bonded to the distal carbon of the spent Hydrogen Abstraction Tool 110 in which hydrogen atom 112 is weakly bonded to carbon atom 102, along with a second (unbonded) Germanium Radical Tool 224. When the second Germanium Radical Tool 224 is positioned in close proximity to hydrogen atom 112 the hydrogen atom 112 debonds from carbon atom 102 and bonds to the germanium radical 226 of the second Germanium Radical Tool 224, thereby converting the second Germanium Radical Tool 224 into a Hydrogen Donation Tool. The result of the reaction is illustrated in FIG. 12C.

Figure 12C:
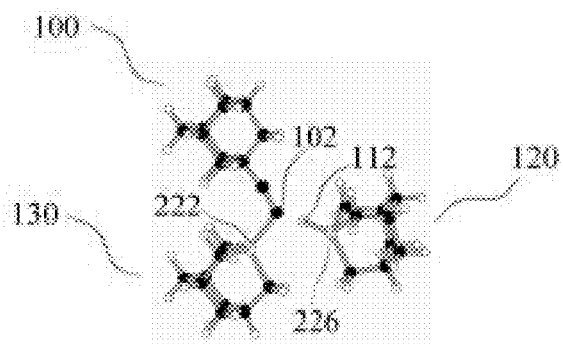
FIG. 12C shows a Germanium Radical Tool breaking bond to spent Hydrogen Abstraction Tool.
Figure 12D:
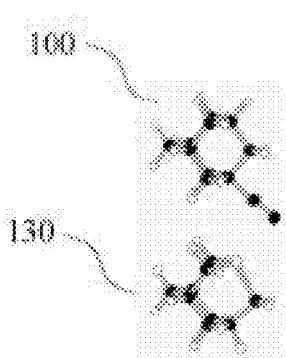
FIG. 12D shows a refreshed Hydrogen Abstraction Tool.

FIG. 12C illustrates the germanium radical 222 of the first Germanium Radical Tool 130 bonded to the distal carbon 102 of the Hydrogen Abstraction Tool 100, along with the resulting Hydrogen Donation Tool 120. When the first Germanium Radical Tool 130 is withdrawn by sufficient applied force from the Hydrogen Abstraction Tool 100, the bond between germanium atom 222 at the tip of the first Germanium Radical Tool 130 and carbon atom 102 at the tip of the Hydrogen Abstraction Tool 100 will break. The result of this mechanosynthetic reaction is illustrated in FIG. 12D, which shows the resulting refreshed Hydrogen Abstraction Tool 100 and recovery of the original Germanium Radical Tool 130 unchanged.

During mechanosynthesis, as many hydrogen atoms as desired can be added by abstracting hydrogen atoms from some convenient source (e.g., a hydrogenated diamond surface) using the Hydrogen Abstraction Tool, and then transferring the hydrogen atoms so obtained to Hydrogen Donation Tools from which they can be added to a workpiece. The reverse of this process can be used to get rid of excess hydrogen atoms by donating them to a convenient sink (e.g., a non-hydrogenated diamond surface) using a Hydrogen Donation Tool. Consequently, the sequence described above can accommodate the net addition or removal of hydrogen atoms.

Charging the GermylMethylene Tool

The discharge of a GermylMethylene Tool creates a spent GermylMethylene Tool, which is identical to a Germanium Radical Tool. A GermylMethylene Tool can be charged by starting with a Germanium Radical Tool and .CH2 groups distributed on a suitable presentation surface (e.g., germanium). The Germanium. Radical Tool is touched to a .CH2 group on the presentation surface, and then withdrawn. Although the .CH2 group is bonded to a germanium atom on the presentation surface and to a germanium atom on the tip of the Germanium Radical Tool, the bond to the germanium atom on the tip of the Germanium Radical Tool is stronger (the germanium on the tip of the Germanium Radical Tool is in a different atomic bonding environment than the germanium on the presentation surface—in particular, it is bonded to 3 carbon atoms rather than being bonded to other germanium atoms).

Upon withdrawal of the tool handle from the presentation surface, the .CH2 group is withdrawn with it, thus converting the Germanium Radical Tool back into a GermylMethylene Tool, completing the recharge process.

Methylation of a Selected Site on a Diamondoid Workpiece

FIGS. 13A-E illustrate mechanosynthetic methylation of a selected atomic site. During fabrication, workpieces will frequently be hydrogenated to eliminate dangling bonds and to avoid unexpected reconstructions. Some of these hydrogenations, particularly when immediately followed by hydrogen abstraction, can simply be omitted. Because of this general assumption, the first step in the methylation sequence is to abstract a hydrogen atom from the specific site to allow addition of a CH3 group. When this general assumption is not used (i.e., when exposed radical sites are not immediately hydrogenated) there might be multiple radical sites available on the workpiece that could be methylated without first abstracting a hydrogen. In such cases, the step illustrated in FIG. 13A in the following sequence could be eliminated, and steps illustrated in FIG. 13D and FIG. 13E might also be eliminated if there is no immediate need to hydrogenate this particular added .CH2 group, leaving only steps illustrated in FIG. 13B and FIG. 13C as required for this method. The need (or lack thereof) for hydrogenation or dehydrogenation in a given case will be readily apparent to a practitioner skilled in the art.

Figure 13A:
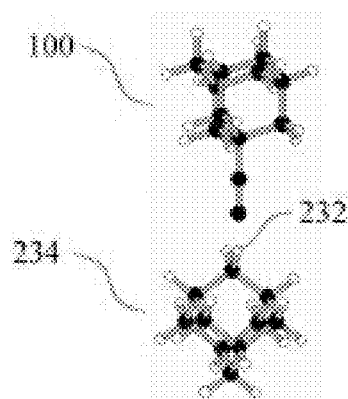
FIG. 13A shows abstracting hydrogen from a workpiece.

FIG. 13A illustrates abstracting the hydrogen atom 232 that occupies the site where the methyl group is to be placed. Hydrogen Abstraction Tool 100 abstracts hydrogen atom 232 from adamantane cage 234, which represents a few atoms from a larger diamond workpiece.

Figure 13B:
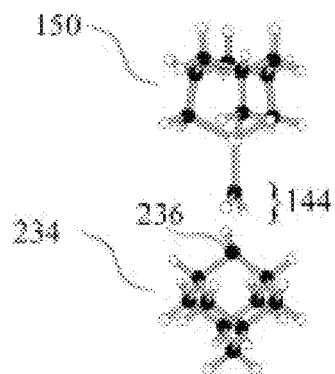
FIG. 13B shows a GermylMethylene Tool being position in close proximity to a radical carbon atom.

FIG. 13B illustrates GermylMethylene Tool 150 being positioned so that .CH2 group 144 is in close proximity to radical carbon atom 236. With the application of mechanical force to overcome reaction barriers, the .CH2 group 144 will then bond to radical carbon atom 236 as shown in FIG. 13C, the next step in the sequence.

Figure 13C:
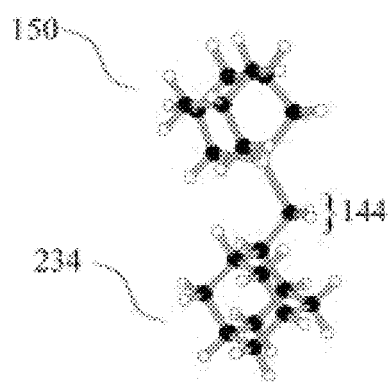
FIG. 13C shows a GermylMethylene Tool bonded to a CH2 group.

FIG. 13C illustrates the GermylMethylene Tool 150 bonded to the .CH2 group 144. The GermylMethylene Tool 150 is withdrawn by the application of mechanical force, converting GermylMethylene Tool 150 into a Germanium Radical Tool (not shown) and the .CH2 group is left behind on the workpiece 234.

Figure 13D:
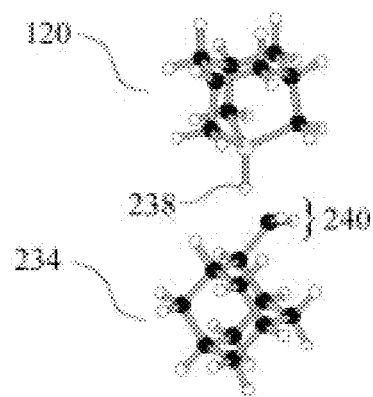
FIG. 13D shows a Hydrogen Donation Tool positioned to donate a hydrogen atom to the CH2 group.

FIG. 13D illustrates a Hydrogen Donation Tool 120 which is positioned to donate hydrogen atom 238 to the radical site on the .CH2 group 240. With the application of mechanical force to overcome reaction barriers, hydrogen atom 238 is bonded to the .CH2 group 240.

Figure 13E:
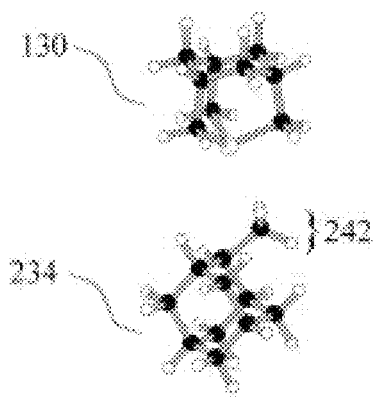
FIG. 13E shows hydrogen transferred to radical site on CH2 group and a Hydrogen Donation Tool converted into a Germanium Radical Tool.

FIG. 13E illustrates the result of the reaction in which the hydrogen on the Hydrogen Donation Tool has been transferred to the radical site on .CH2 group 240, converting it to CH3 group 242. The Hydrogen Donation Tool is converted by this process into Germanium Radical Tool 130.

This build sequence provides a specific example of a more general method. This method can be applied to add a methyl group to virtually any exposed carbon radical on any hydrocarbon structure. It can also be used to add a methyl group to a wide range of other possible target structures.

Ring Closure on a Diamondoid Workpiece

The addition of individual methyl groups is a versatile technique, and in conjunction with the ability to close a ring, provides a mechanism for fabricating a wide range of diamondoid structures.

Figure 14A:
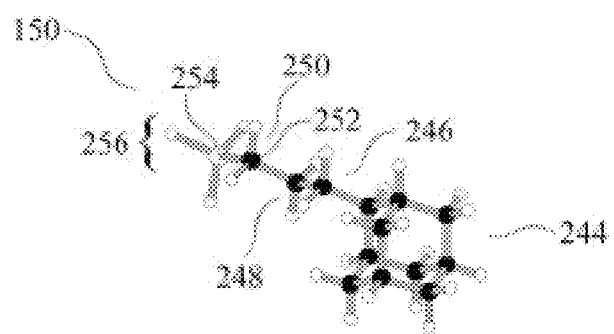
FIG. 14A shows a GermylMethylene Tool bonded to the third methylene group of a chain of three methylene groups that has been bonded to an adamantane workpiece.

FIG. 14A illustrates a structure to which three CH2 groups have already been added. The first CH2 group 246 is attached to a sidewall site on adamantane cage 244, a cage that represents a few atoms from a larger diamond workpiece. The second CH2 group 248 is added to the first CH2 group 246, and the third CH2 group 250 is added to the second CH2 group 248. The GermylMethylene Tool 150 that is used to add the third CH2 group 250 (thus incorporating the final carbon atom 252 in the chain) is not withdrawn, but instead is left attached so that this tool can be used to re-position carbon atom 252. For purposes of brevity of illustration only, the GermylMethylene Tool 150 is represented by a single germanium atom 254 and 3 attached hydrogen atoms 256, rather than the full adamantane cage structure of the GermylMethylene Tool 150 as shown in FIG. 5.

Figure 14B:
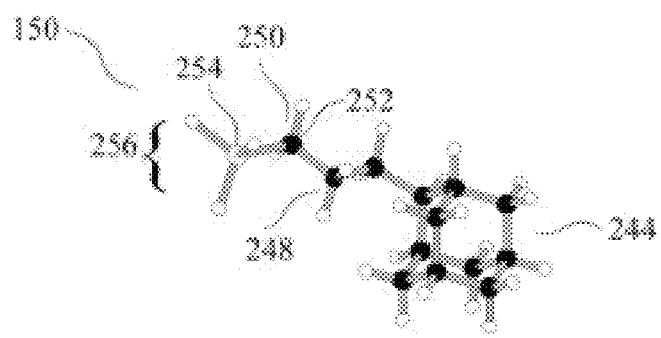
FIG. 14B shows the third methylene group rotated to a different position relative to the chain of three methylene groups attached to an adamantane workpiece, using a GermylMethylene Tool.

FIG. 14B illustrates the structure that results after CH2 group 250 has been rotated from the trans to the cis configuration relative to CH2 group 248, which is accomplished by the application of lateral forces transmitted through the handle of the attached GermylMethylene Tool 150.

Figure 14C:
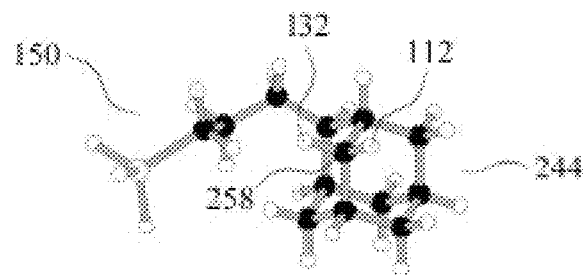
FIG. 14C shows the chain of three methylene groups rotated into a cagelike configuration relative to an adamantane workpiece, using a GermylMethylene Tool bonded to the third methylene group in the chain of three methylene groups.

FIG. 14C illustrates the structure that results after CH2 group 248 has been further rotated relative to CH2 group 246 such that the three CH2 groups 246, 248 and 250 are re-oriented into a cage-like configuration relative to the workpiece; this re-orientation is accomplished by the application of lateral forces transmitted through the handle of the attached GermylMethylene Tool 150. FIG. 14C also shows the location of hydrogen atom 132 that will be abstracted in the next reaction step, and the location of hydrogen atom 112 that will be abstracted in the next reaction step after that.

Figure 14D:
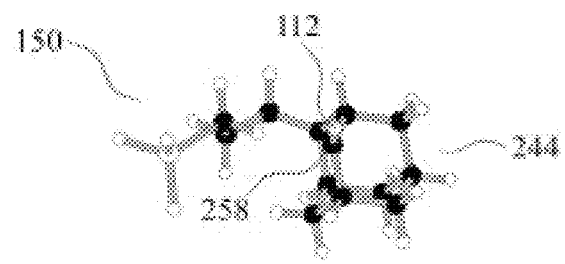
FIG. 14D shows the configuration of FIG. 14C after a first hydrogen atom has been abstracted from a sidewall carbon atom of the adamantane workpiece.

FIG. 14D illustrates the workpiece 244 after the abstraction of hydrogen atom 132 from carbon atom 258. FIG. 14D also shows the location of hydrogen atom 112 that will be abstracted in the next reaction step.

Figure 14E:
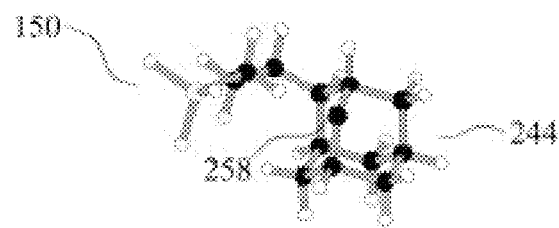
FIG. 14E shows the configuration of FIG. 14D after a second hydrogen atom has been abstracted from the same sidewall carbon atom of the adamantane workpiece.

FIG. 14E illustrates the workpiece 244 after the abstraction of a second hydrogen atom 112 from the same carbon atom 258, which becomes a carbene diradical. The two hydrogen abstractions that occur in FIG. 14D and FIG. 14E are not shown explicitly but require the use of two Hydrogen Abstraction Tools in the abstraction process.

Figure 14F:
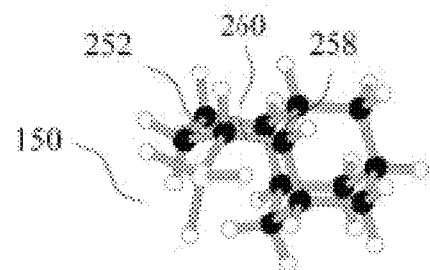
FIG. 14F shows the chain of three methylene groups bonded to a sidewall carbon atom of the adamantane workpiece, thus closing a ring of three methylene groups, with the GermylMethylene Tool still attached.

FIG. 14F illustrates GermylMethylene Tool 150 being positioned so that carbene 258 inserts into the CH bond between carbon atom 252 and one of its attached hydrogen atoms with the application of mechanical force. Following this insertion reaction, carbon atom 252 will bond to carbon atom 258 via bond 260.

Figure 14G:
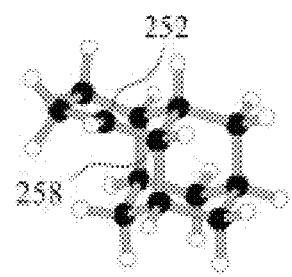
FIG. 14G shows the configuration of FIG. 14F after the GermylMethylene Tool is detached.

FIG. 14G illustrates the workpiece after the GermylMethylene Tool 150 is withdrawn, leaving carbon atom 252 attached to carbon atom 258. Carbon atom 252 is now, because of the withdrawal of GermylMethylene Tool 150, a radical.

Figure 14H:
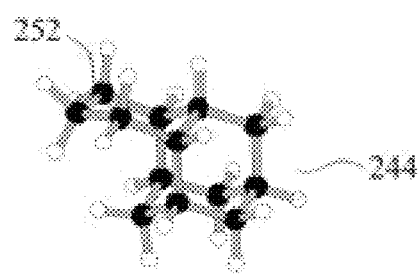
FIG. 14H shows the adamantane workpiece with a fully passivated three-methylene ring attached between two sidewall sites.

FIG. 14H illustrates the state after the final step in the build sequence which is to hydrogenate the radical site at carbon atom 252 using a Hydrogen Donation Tool 120 (not shown). The donation reaction, which requires the application of mechanical force to overcome a reaction barrier, is not shown explicitly but requires the use of a Hydrogen Donation Tool. Following this hydrogenation, carbon atom 252 has four bonds, two bonds to adjacent carbon atoms and two bonds to hydrogen atoms. This build sequence results in a closed chain of 3 carbon atoms (derived from CH2 groups 246, 248 and 250) being added to workpiece 244.

GermylMethylene Tool 150 must be positionally rotated during this sequence. An alternative method of changing the orientation of GermylMethylene Tool 150 is to perform a handle exchange, substituting a new tool in a new orientation for the existing GermylMethylene Tool 150. In this alternative method, a hydrogen atom is first abstracted from CH2 group 250 at the tip of the attached GermylMethylene Tool 150, creating a radical site at carbon atom 252 to which a new Germanium Radical Tool which is already in the desired new orientation (and precisely positioned in X, Y and Z) can next be bonded. Following this bonding, withdrawal of the GermylMethylene Tool 150 leaves the carbon atom 252 bonded to the new Germanium Radical Tool (not shown in this figure). The radical carbon atom 252 is then hydrogenated with an additional Hydrogen Donation Tool (not shown in this figure). This process effectively performs a handle exchange, with the new handle in a different orientation. This avoids the need to manipulate a single handle and change its orientation while it is attached to the workpiece, simplifying the positioning required during the ring-closing build sequence described above.

While the above described method of creating a ring is often useful due to its versatility, it is possible to fabricate diamond using simpler methods in some cases. In particular, in the case of mechanosynthetic manufacture of the C(110) diamond surface, methyl groups can be added on top of the troughs on the C(110) surface and then cross-bonded. This process described in more detail below (and illustrated in FIG. 19) in the context of fabricating a simple handle structure during a bootstrap process.

Building Tool Handles

Once the ability to fabricate diamond and similar hydrocarbons is achieved (using the ring closure reaction as described above, or using methylation of a C(110) diamond surface as described below, or using other reactions that would readily be apparent to someone skilled in the art and having the benefit of the teachings presented herein), atomically-precise handle structures can be fabricated that will be suitable for supporting the various tips illustrated in FIGS. 1-9.

Building Specific Tools

Figure 1B:
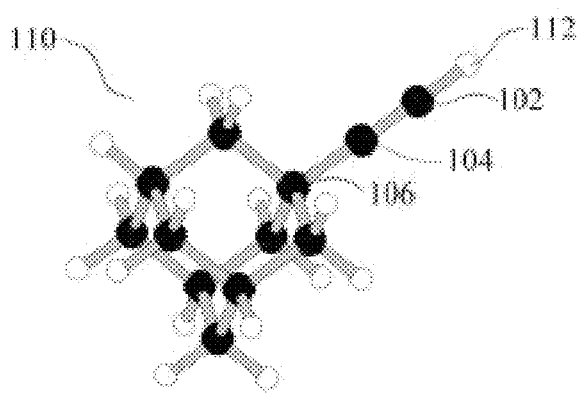
FIG. 1B is a spent Hydrogen Abstraction Tool.

Given a sufficient number of each type of the bootstrap tools, it is possible to build more of any of the nine tools. Once having built a suitable handle structure, the specific tip can be added. Reviewing the tools in order:

(1) Hydrogen Abstraction Tool. Having built the handle and the adamantane cage at the end of the handle, a methyl group is added at the apex, followed by adding a second methyl group to the first methyl group. All but one of the hydrogen atoms on these two methyl groups are then abstracted using other Hydrogen Abstraction Tools, creating the Hydrogen Abstraction Tool in its spent version (as shown in FIG. 1B). This structure is then refreshed using the Hydrogen Abstraction Tool recharge sequence shown in FIG. 12.

(2) Hydrogen Donation Tool. A Germanium Radical Tool is used in the Hydrogen Abstraction Tool recharge sequence shown in FIG. 12 to convert the Germanium Radical Tool to a Hydrogen Donation Tool.

(3) Germanium Radical Tool. Having built the handle, the Germylene Tool is used to add the single germanium atom needed at the tip of this tool.

(4) Methylene Tool. Starting with the Adamantane Radical Tool, the Adamantane Radical Tool is bonded to a .CH2 group on a suitable presentation surface (e.g., germanium) and retract the tool producing a Methylene Tool.

(5) GermylMethylene Tool. The Germanium Radical Tool is bonded to a .GeH2 group on a suitable presentation surface (e.g., germanium). The reaction energetics favor transfer of the .GeH2 group to the tool from a germanium presentation surface. The tool is then retracted, producing a GermylMethylene Tool.

(6) Germylene Tool. The Adamantane Radical Tool is bonded to a .GeH2 on a suitable presentation surface (e.g., germanium) and the tool is retracted, producing a Germylene Tool.

Figure 15A:
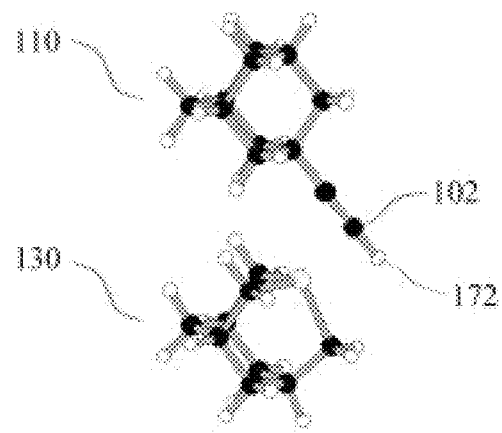
FIG. 15A shows a Germanium Radical Tool bonded to a spent Hydrogen Abstraction Tool.
Figure 15B:
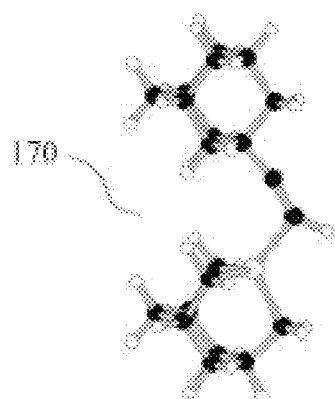
FIG. 15B shows a resulting Hydrogen Transfer Tool.

(7) Hydrogen Transfer Tool. Starting with a spent Hydrogen Abstraction Tool and a Germanium Radical Tool as shown in FIG. 15A, Germanium Radical Tool 130 is bonded to the distal carbon atom 102 of the spent Hydrogen Abstraction Tool 110 yielding Hydrogen Transfer Tool 170 as shown in FIG. 15B.

(8) Dimer Placement Tool. After fabricating a first Germanium Radical Tool, a second Germanium Radical Tool is constructed in a lonsdaleite polytype configuration on the side of the first Germanium Radical Tool, yielding a discharged Dimer Placement Tool which is then recharged with C2 dimer by the addition of two carbon atoms using two GermylMethylene Tools, followed by the abstraction of four hydrogen atoms using four applications of Hydrogen Abstraction Tools.

(9) Adamantane Radical Tool. Using the Hydrogen Abstraction, Hydrogen Donation and GermylMethylene Tools, the handle structure for the Adamantane Radical Tool and the Adamantane Radical Tool itself can be built.

Given enough Hydrogen Abstraction Tools and Hydrogen Donation Tools, one can build a limited number of Germanium Radical Tools (limited by the number of Hydrogen Donation Tools) by using the Hydrogen Donation Tools to donate hydrogen atoms to a hydrogen dump (e.g., a non-hydrogenated diamond surface). With these Germanium Radical Tools one can build and recharge GermylMethylene Tools (given the availability of a suitable presentation surface for .CH2 groups). Using these tools, and recharging the tools as needed, one can then build as many Hydrogen Abstraction Tools and as many Adamantane Radical Tools as desired (these tools are made from carbon and hydrogen only, and have no germanium).

With the availability of a suitable presentation surface for .CH2 groups, the Adamantane Radical Tools can be charged with .CH2 groups, producing as many Methylene Tools as desired. And, with the availability of a suitable presentation surface for .GeH2 groups, the Adamantane Radical Tools can be charged with .GeH2 groups, producing as many Germylene Tools as desired.

The Germylene Tool, along with the previously available tools, allows the fabrication of as many Germanium Radical Tools as desired, which in turn allows the fabrication of as many GermylMethylene Tools and as many Hydrogen Donation Tools as desired. Combining spent Hydrogen Abstraction Tools and Germanium Radical Tools allows the fabrication of as many Hydrogen Transfer Tools as desired. Finally, as many Dimer Placement Tools as desired can be fabricated using the previous tools.

Although various embodiments have been described in considerable detail above, many other embodiments are possible. For example, having fabricated a sufficient number of rechargeable atomically-precise tools, it will be apparent that other build sequences would allow the fabrication of a wide range of atomically-precise structures, and that other tools designs are readily created using the teachings herein, as are reactions to include many other elements and molecules.

Introduction to the Bootstrap Process

Once the first atomically-precise tools exist, they can be used to fabricate more of the self-same tools. But the first set of atomically-precise tools must be manufactured using only currently available atomically imprecise tools, or proto-tools, a process called bootstrapping. Numerous approaches exist for bootstrapping the first atomically-precise tools from proto-tools.

One approach is to synthesize appropriate molecules and then attach these (or similar molecules that have appropriate tip structure) to the tip structure of an SPM-like device to create the first proto-tools via tip functionalization; a wide range of molecular structures having the desired functionality similar to atomically-precise tools are feasible. AFM tip functionalization is well-known in the literature. See (Wong, Woolley et al., "Functionalization of carbon nanotube AFM probes using tip-activated gases," Chemical Physics Letters, 306, 1999; Grandbois, Dettmann et al., "Affinity Imaging of Red Blood Cells Using an Atomic Force Microscope," Journal of Histochemistry & Cytochemistry, 48, 2000; Halher, Cheung et al., "Structural and Functional Imaging with Carbon Nanotube AFM Probes," Progress in Biophysics & Molecular Biology, 77, 2001).

Another approach is to use commercially available SPM ultra-sharp tips. This approach is described in detail below.

The Bootstrap Process

The present invntion describes a set of nine molecular tools sufficient to make additional sets of the self-same tools (the "minimal toolset") as described above. These tools are illustrated in FIGS. 1-9. Given an adequate initial number of each of these nine tools, with the tools being positionally controlled by suitable positional devices and given suitable presentation surfaces for feedstock, it is possible to build additional sets of the self-same tools.

The first toolset, however, must be built without the benefit of a previously existing toolset. Thus, this first toolset must be fabricated from simpler proto-tools using methods that are experimentally accessible. Once such a bootstrap process has been executed, yielding a first set of tools in small but adequate numbers, the bootstrap process need not be repeated again.

Hence, each build sequence comprising the bootstrap process need only be carried out a small number of times. As a consequence, any methods (even those that would be too expensive or unreliable for continued use) of building the first set of tools are sufficient to enable the fabrication of more tools. These methods can be carried out at low temperature (e.g., 77K-80 K is readily available using liquid nitrogen, or 4 K using liquid helium) and by the use of proto-tools having only modest reliability. Reducing the temperature dramatically increases the number of reliable operations that are available for use during the bootstrap sequence using proto-tools, even if the resulting more sophisticated final toolset (which is fabricated by the proto-tools) is intended for use at higher temperatures.

It is possible to make the complete set of nine tools given only the Hydrogen Abstraction and Hydrogen Donation Tools. With a small but adequate initial supply of these two tools, when operated with appropriate positional control in an inert environment, and when provided with a source of feedstock (e.g., .CH2, .GeH2 and H distributed on appropriate presentation surfaces) and a hydrogen dump (a surface with a high affinity for hydrogen on which excess hydrogen would be placed, e.g., bulk-produced atomically flat clean diamond), it is possible to manufacture all nine tools. Therefore, in one embodiment of a representative bootstrap process, proto-tools are fabricated that are the functional equivalent of the Hydrogen Abstraction and Hydrogen Donation Tools.

There are many possible bootstrap sequences depending on the toolset, on the particular method of selecting an initial subset of the tools, and on the particular method of creating functional equivalents of those initial tools using existing technology. One approach is to synthesize appropriate molecules and then attach these (or similar molecules that have appropriate tip structure) to the tip structure of an SPM-like device to create the first proto-tools via tip functionalization. Another approach is using commercially available SPM ultra-sharp tips. The particular sequence described here employs existing ultrasharp silicon and diamond SPM tips.

Current ultrasharp scanning probe tips having nanometer or sub-nanometer radius of curvature, when operated at low temperature, are sufficient for the modest reliability requirements of a bootstrap sequence. Such ultrasharp scanning probe tips are commercially available, e.g., silicon tips with tip radii of 2 nm or less, and diamond-like carbon (DLC) spike-probe tips having a sub-nanometer asperity that is only a few carbon atoms wide at its distal terminus.

Bootstrap processes are simplified by following the general principle that feedstock is moved downhill in energy or bonding force as it is transferred, for example, from the feedstock presentation surface, to the tip, and finally to the workpiece. While other sequences are possible (e.g., when removing atoms from a workpiece) the principle is the same: design the combination of feedstock, tip, and workpiece so that the desired reactions are favored by the net energy change or binding force differences.

Implementing this general principle proceeds in the following stages:

(1) Distribute desired feedstock onto a presentation surface. While the feedstock bonds more weakly to the surface than to the tip (making it easy to acquire the feedstock with the tip), the feedstock bonds strongly enough to prevent problematic migration or departure from the presentation surface at the designated operating temperature.

(2) If necessary, activate the feedstock (e.g., by abstracting a hydrogen atom and making it reactive, once the first hydrogen abstraction tool is available).

(3) Bring a tip (positioned by an SPM-like apparatus or some other positional device) into contact with the activated feedstock, and bond to it with the tip, possibly requiring the application of mechanical force to overcome reaction barriers. The resulting newly formed bond is stronger than the bond that holds the feedstock to the presentation surface.

(4) Withdraw the tip, and with it withdraw the transferred feedstock from the presentation surface.

(5) Use the SPM tip to position the transferred molecule next to a workpiece, and form a bond with the feedstock and the workpiece, possibly requiring the application of mechanical force to overcome reaction barriers. For an appropriately selected workpiece and feedstock, the bond that forms between the workpiece and the cluster will be stronger than the bond between the cluster and tip.

(6) Withdraw the tip, leaving the transferred feedstock behind on the workpiece.

If the presentation surface is germanium (which forms relatively weak bonds) and the feedstock is .CH2, .GeH2 or even more simply just a single hydrogen atom H, then a silicon tip will bond to the feedstock more strongly than the germanium surface bonds to the feedstock. If the workpiece is a stiff hydrocarbon structure, the feedstock (e.g., H, .CH2, or .GeH2) will bond more strongly to a radical carbon site on the workpiece than to the silicon tip, and so can be transferred to the workpiece at a desired location. That is, the feedstock's net energy decreases, or bonding force increases, as it transfers from the presentation surface, to the tip, and finally to the workpiece.

Even when the bond strengths or energies between the feedstock, the presentation surface, the SPM tip and the workpiece are very similar, test-and-repeat steps, or other techniques can be used to obtain adequately reliable results. Such procedures are discussed in more detail herein.

Lowering the temperature can also be used to reduce the randomizing effect of thermal noise. At a sufficiently low temperature for a given reaction, thermal noise will no longer significantly disturb the outcome and the reliability of the operations is then limited by other factors.

Figure 16A:
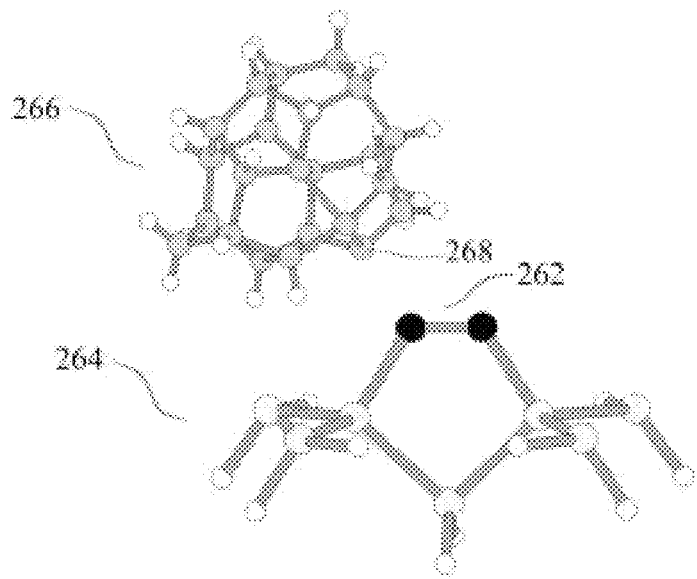
FIG. 16A shows a bootstrap sequence for a proto-Hydrogen Abstraction tip.

Starting a Bootstrap Sequence: the proto-Hydrogen Abstraction tip. FIG. 16A illustrates how a bootstrap sequence may start with the fabrication of a proto-Hydrogen Abstraction tip. The proto-Hydrogen Abstraction tip 270 (FIG. 16B) differs from the Hydrogen Abstraction Tool 100 (FIG. 1) in that the proto-Hydrogen Abstraction tip does not necessarily have an atomically-precise adamantane cage at the base of the ethynyl radical. It should be understood that the particular proto-Hydrogen Abstraction tip 270 is but one instance of an entire class of structures that incorporates some degree of randomness but which still has the requisite properties. For the proto-Hydrogen Abstraction tip it is sufficient that the ethynyl radical is in place and functions.

One method of preparing the first proto-Hydrogen Abstraction tip is by the following five-step sequence.

(1) C2 dimers are chemisorbed onto an appropriate presentation surface. As illustrated in FIG. 16A, the preparation may begin with the adsorption of C2 dimers 262 onto a surface 264 (or into a matrix) which may be, among other possibilities, copper, frozen noble gases (or similarly unreactive compounds), germanium, germanium carbide, graphene, silicon, silicon carbide, or platinum.

(2) Having once obtained a suitable presentation surface with C2 dimers distributed on it, a sub-nanometer radius diamond tip 266 is at least partially depassivated by any of several methods, which might include: (A) heating to an appropriate temperature (e.g., 700-800 K for diamond C(111) and C(100) surfaces), (B) contacting the tip to an already depassivated surface (e.g., a surface with an equal or higher affinity for hydrogen), or (C) by the standard practice of applying a suitable voltage pulse to cause removal of one or more hydrogen atoms from the tip. This produces at least one radical site 268 on the tip.

(3) The tip 266 is brought into contact with one end of a chemisorbed dimer 262, resulting in the dimer bonding to the tip, possibly requiring the application of mechanical force to overcome reaction barriers.

Figure 16B:
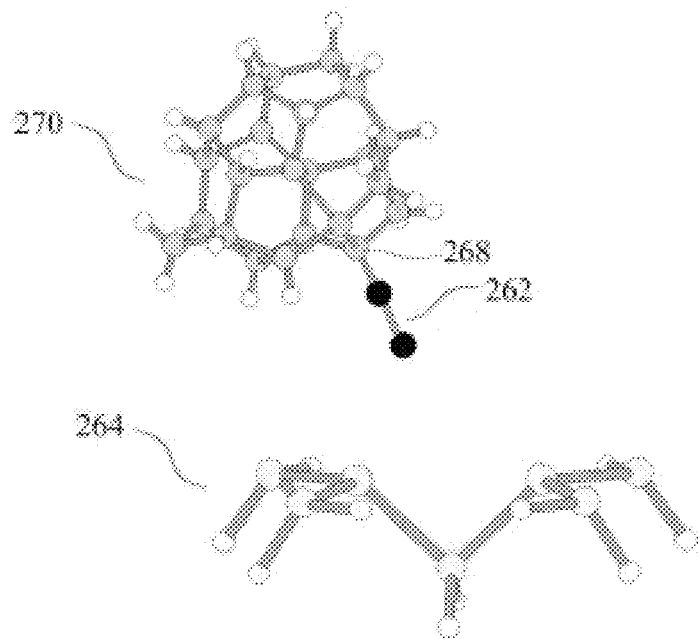
FIG. 16B shows the result when the proto-Hydrogen Abstraction tip is withdrawn from the presentation surface.

(4) The tip is then withdrawn from the presentation surface, producing the desired proto-Hydrogen Abstraction tip 270 as illustrated in FIG. 16B.

(5) A "test and repeat" step may be employed to ensure that the resulting proto-Hydrogen Abstraction tip has been made successfully, if increased reliability is desired.

The resulting proto-Hydrogen Abstraction tip can then be used to selectively abstract hydrogen in subsequent mechanosynthetic steps. In addition, the minimal toolset (as described in (Freitas and Merkle, "A Minimal Toolset for Positional Diamond Mechanosynthesis," Journal of Computational and Theoretical Nanoscience, 5, 2008)) reactions normally required in the recharge sequence for the proto-Hydrogen Abstraction tip may be avoided during the bootstrap sequence by discarding the proto-Hydrogen Abstraction tip after a single use and making additional proto-Hydrogen Abstraction tips as needed to abstract additional hydrogen atoms. While inefficient, such a process serves to produce a sufficient number of proto-Hydrogen Abstraction tips during the bootstrap process.

The proto-Silicon Hydrogen Donation tip. A proto-Hydrogen Donation tip is useful for donating a hydrogen atom to a carbon radical on a diamond workpiece, among other Hydrogen donation reactions.

The most direct method for obtaining a proto-Hydrogen Donation tip is to create an ultrasharp hydrogenated silicon or germanium tip. Ultrasharp silicon tips are readily available commercially, and so silicon is used as an exemplary embodiment. The primary reason for using germanium would be the higher reliability of operation with germanium due to the Ge—H bond being weaker than the Si—H bond. However, the bootstrap sequence will work with silicon substituted for germanium, albeit with lower reliability at a given operating temperature. Lowering the temperature of operation recovers much of the foregone reliability. Thus the use of commercially available silicon tips will suffice because lower temperature operation during the bootstrap sequence is readily available, and because lower-reliability processes are tolerable during bootstrapping.

Figure 17A:
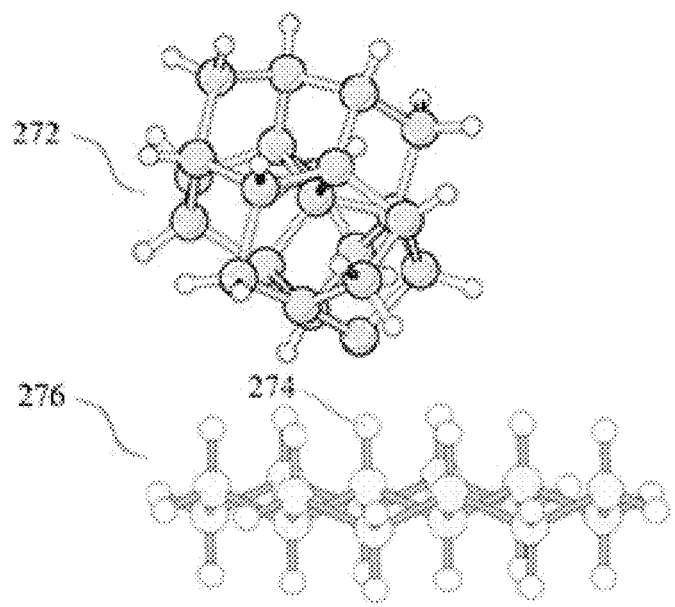
FIG. 17A shows a dehydrogenated proto-Silicon Hydrogen Donation tip prior to conversion into a hydrogenated proto-Silicon Hydrogen Donation tip.
Figure 17B:
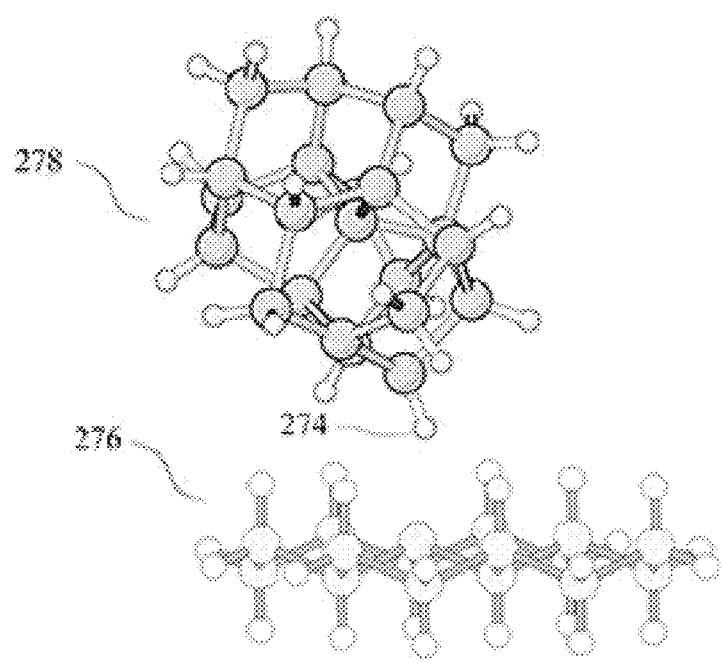
FIG. 17B shows the converted proto-Silicon Hydrogen Donation tip.

FIG. 17A shows a partially-dehydrogenated proto-Hydrogen Donation tip 272 (which, as is explained herein, in its radical form, may be structurally the same as the proto-Silicon Radical tip) above a hydrogenated germanium surface 276. FIG. 17B shows the hydrogenated proto-Hydrogen Donation tip 278 after it has acquired a Hydrogen 274 from a hydrogenated germanium surface. After use, the partially-dehydrogenated proto-Hydrogen Donation tip 272 can be recharged for repeated use by touching it to a hydrogenated germanium surface.

It should be understood that the particular proto-Hydrogen Donation tip 272 (in dehydrogenated form) and 278 (in hydrogenated form) is but one instance of an entire class of structures that incorporates some degree of randomness but which still has the requisite properties. Further, other ways of recharging such a tip would be obvious given the teachings herein.

The Proto-Hydrogen Abstraction tips and proto-Silicon Hydrogen Donation tips are then used to fabricate the rest of the tips in the bootstrap process, followed by all the tools in the minimal toolset as described below.

The proto-Silicon Radical tip. By touching the correct location on a proto-Silicon Hydrogen Donation tip to a hydrogen dump (which may be, among other methods, a dehydrogenated diamond surface, or via the removal of the appropriate Hydrogen with the proto-Hydrogen Abstraction tip), a hydrogen atom is removed from the proto-Silicon Hydrogen Donation tip, thus creating a radical site on the tip. The resulting tip is designated as a proto-Silicon Radical tip 266.

Note that while the proto-Silicon Radical tip may be structurally (or effectively, given that many different structures can serve this purpose) identical to a dehydrogenated proto-Hydrogen Donation tip, the naming convention is used to make clear that generally, in instances where a "proto-Silicon Radical tip" is discussed, rather than a "proto-Hydrogen Abstraction tip," something other than Hydrogen is being abstracted (e.g., the .CH2 group discussed below). The proto-Silicon Radical tip provides the functionality of the Germanium Radical Tool for some or all of the bootstrap sequence.

More generally, a wide range of possible proto-radical tips may be used, and there are many methods of manufacturing any particular tip, as for example: (1) heating a workpiece diamond, silicon or germanium tip to a temperature sufficient to drive off some of the hydrogen atoms on the tip (e.g., 700-800 K for diamond C(111) and C(100) surfaces), (2) employing the standard practice of applying a voltage pulse of appropriate magnitude and duration at the workpiece tip to remove one or more hydrogen atoms, or (3) applying a proto-Hydrogen Abstraction tip or Hydrogen Abstraction Tool to the workpiece tip.

The proto-Silicon Methylene tip. Once fabricated, the proto-Silicon Radical tip is touched to a .CH2 group on a suitable presentation surface to create the functional equivalent of a GermylMethylene Tool. This functional equivalent may be called a proto-Silicon Methylene tip.

Figure 18A:
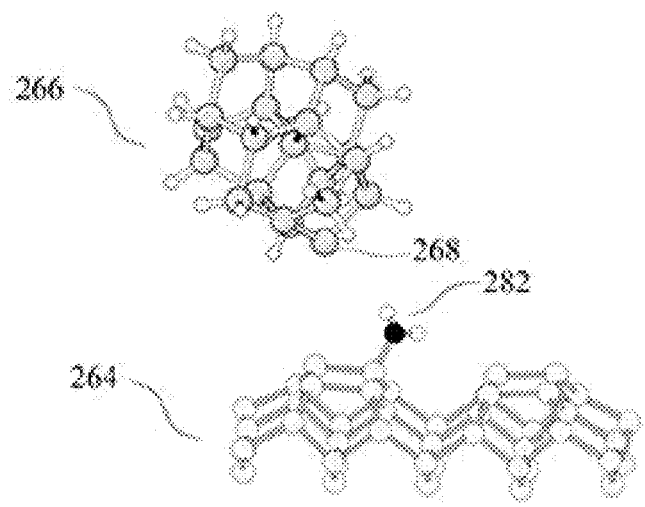
FIG. 18A shows charging a proto-Silicon Radical tip.

More generally, any radical tip, including the proto-Silicon Radical tip, can be charged by using many possible methods, as exemplified by the following series of steps and FIG. 18A:

(1) CH3 groups are distributed on a suitable presentation surface 264.

(2) A proto-Hydrogen Abstraction tip removes a selected hydrogen from a specific CH3 group chemisorbed to the presentation surface, leaving .CH2 group 282 chemisorbed to presentation surface 264.

(3) Proto-Silicon Radical tip 266 approaches .CH2 group 282 (chemisorbed to presentation surface 264).

(4) The radical site 268 on proto-Silicon Radical tip 266 bonds with .CH2 group 282 on presentation surface 264.

Figure 18B:
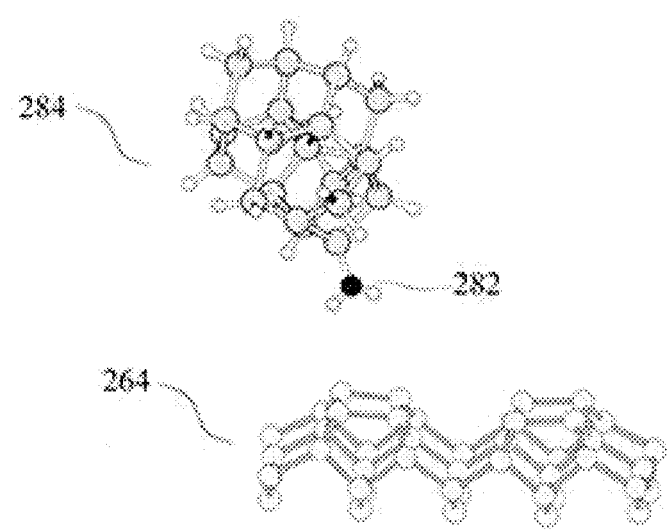
FIG. 18B shows fabrication of a proto-Silicon Methylene tip.

(5) In FIG. 18B, the proto-Silicon Methylene tip 284 is withdrawn from presentation surface 264 by the application of mechanical force, taking CH2 group 282 with it, resulting in the fabrication of proto-Silicon Methylene tip 284 from proto-Silicon Radical tip 266. Because of the relatively low reliability and the possibility of positioning errors while using these early tips, it may be necessary to test to determine if .CH2 group 282 has in fact attached to proto-Silicon Radical tip 284 upon its withdrawal.

This completes the fabrication of the proto-tools. The fabrication of the tools of the minimal toolset using the above-described set of proto-tools can now begin.

While many of the mechanosynthesis reactions herein are generally directed towards the production of diverse, atomically-precise structures, while using the proto-tools during the bootstrap process some simplifications can be made because the objective during the bootstrap process is to manufacture a more limited set of structures; in particular, an initial set of atomically-precise tools.

Tools and Handles

Tools generally have a tip and a handle, the handle being a mounting point for the tip. In one embodiment, a suitable handle can be fabricated by starting with a small bulk-produced diamond surface. While various diamond surfaces can be used, the ring closure reactions are particularly simple when the diamond C(110) surface is used.

Figure 19A:
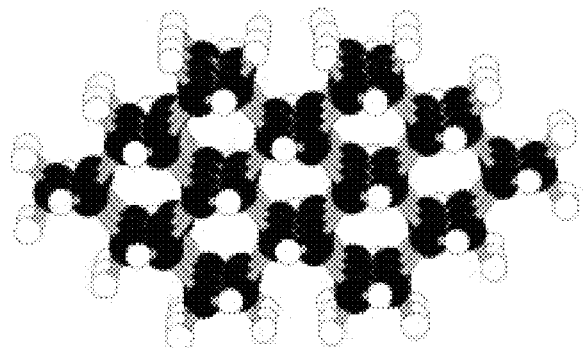
FIG. 19A shows a small section of diamond C(110) surface representing an atomically-precise workpiece upon which the C(110) surface is exposed.

FIG. 19A illustrates this surface consisting of staggered rows of atomic-scale troughs. Fabrication of additional C(110) surface takes place when a zig-zag chain of carbon atoms is emplaced straddling the length of an existing trough. Two zig-zag chains added in adjacent troughs form a new trough between them, atop which an additional chain of carbon atoms can be added. Construction of a single zig-zag chain can proceed by adding single carbon atoms to the end of the chain.

Figure 19B:
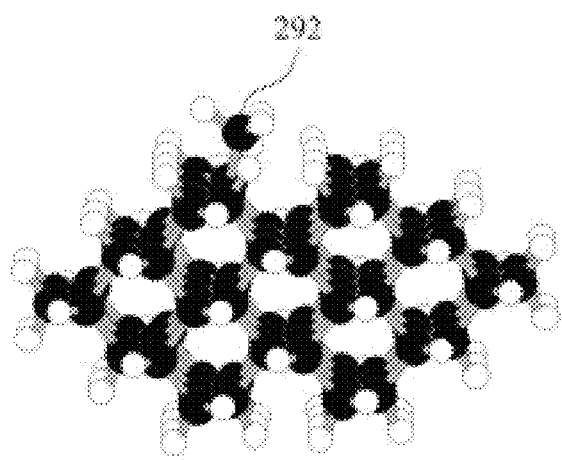
FIG. 19B shows a diamond C(110) atomically-precise workpiece surface with a CH3 group bonded to a specific atom on the left side of a trough.

Fabrication of a suitable handle using the proto-tools starting with a hydrogenated diamond C(110) surface begins as follows: (1) abstract a single hydrogen from the surface using a proto-Hydrogen Abstraction tip, creating a radical site; (2) add a .CH2 group at the radical site using a proto-Silicon Methylene tip; and (3) add a hydrogen atom to the added .CH2 group using a proto-Silicon Hydrogen Donation tip. FIG. 19B illustrates how this three-step build sequence adds a CH3 group containing carbon atom 292 to the left hand side of a trough on the C(110) surface.

Figure 19C:
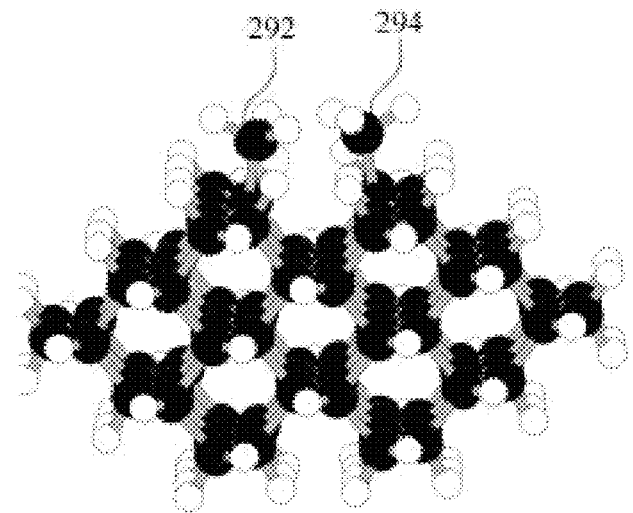
FIG. 19C shows a diamond C(110) atomically-precise workpiece surface with a CH3 group bonded to a specific atom on the left side of a trough and a second methyl group bonded to a specific neighboring atom on the right side of the same trough.
Figure 19D:
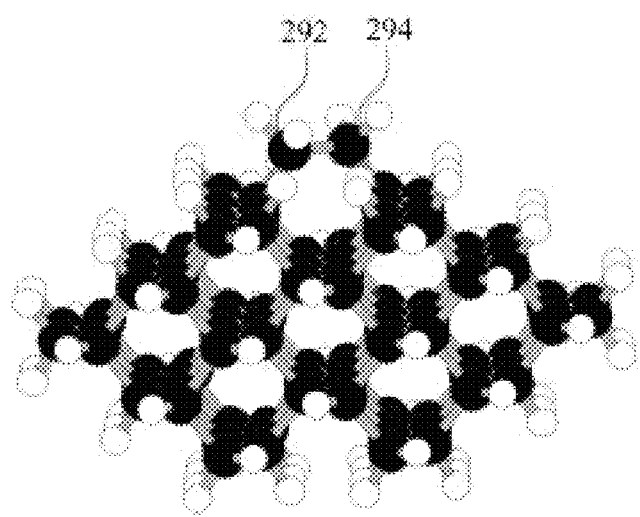
FIG. 19D shows two CH2 groups bonded across a trough on a diamond C(110) atomically-precise workpiece surface.

FIG. 19C illustrates how an additional CH3 group containing carbon atom 294 is added by the same method on the right side of the trough. After two methyl groups have been added on opposite sides of the same trough, two proto-Hydrogen Abstraction tips are applied, one to each methyl group, yielding two .CH2 groups in which both carbon 292 and carbon 294 are radicals, which then bond via radical coupling to form a single CH2CH2 group, constituting one "zig" of a zig-zag chain on the C(110) surface, as illustrated in FIG. 19D. A "zag" is then added by bonding in similar manner a third methyl group on the left hand side of the trough next to the attachment site of the first methyl group, across the trough from the attachment site of the second methyl group. A sequential application of two more proto-Hydrogen Abstraction tips to the second CH2 group and the third methyl group yields two new radical sites which then bond via radical coupling, now forming a three-carbon CH2CHCH2 "zig-zag" sequence straddling the trough of the C(110) surface. This process is continued to produce the first zig-zag chain of desired length in the lowest (most foundational) layer of the tool handle. Following the addition of this zig-zag chain, a second, third, and following chains are added in adjacent troughs on the initial C(110) surface.

This method is used to fabricate a new layer of the C(110) surface, on top of the original surface, of some specific desired size. The process is then repeated, building up a second new layer that is slightly smaller in both lateral dimensions than the first. A third layer, similarly slightly smaller than the second layer, continues this process. Additional new layers decreasing in lateral extent are fabricated until the apex of the resulting pyramid is small enough (e.g., the width of a single adamantane cage) to provide a suitable base for the intended tool whose handle is being manufactured.

The Adamantane Radical Tool. The proto-tools including the proto-Hydrogen Abstraction tip, the proto-Silicon Hydrogen Donation tip, the proto-Silicon Radical tip, and the proto-Silicon Methylene tip can be used in subsequent reactions to make the first Adamantane Radical Tool. In these reactions the proto-Hydrogen Abstraction tip would be used in place of the Hydrogen Abstraction Tool, the proto-Silicon Radical tip would be used in place of the Germanium Radical Tool, the proto-Silicon Methylene tip would be used in place of the GermylMethylene Tool, and the proto-Silicon Hydrogen Donation tip would be used in place of the Hydrogen Donation Tool.

In the case of the Adamantane Radical Tool, the tip culminates in a single bridgehead carbon atom at the apex of a pyramid structure constructed as described above. The bridgehead carbon atom apex is either manufactured in an unhydrogenated state or is dehydrogenated after manufacture using a proto-Hydrogen Abstraction tip or Hydrogen Abstraction Tool. This sequence of reactions for building the Adamantane Radical Tool is very simple because it requires only the application of a single tool or tip at a time to build the necessary handle structure. Since the handle is built layer by layer, the aspect ratio of the initial bootstrapped tips that are used during the fabrication process can be quite poor because the workpiece is geometrically accessible and all multi-tip operations are eliminated. The aspect ratio of the manufactured tools is improved during successive tool-building iterations.

Other tools are constructed by a similar sequence, but with the final apex structures and modifications thereto fabricated using a slightly different sequence of reactions. For example, the Hydrogen Abstraction Tool can be directly fabricated from the Adamantane Radical Tool, as can the Germylene Tool. It is also possible to use alternative tools, tips and processes that are less reliable at higher temperatures but which, when operated at a sufficiently low temperature, become reliable enough for use during the bootstrap process—as for example a proto-Silicon Carbene tip (which is not employed in the bootstrap process described above but could be used in an alternative process to insert a third carbon atom between two previously bonded carbon atoms in a growing diamond surface).

The Hydrogen Abstraction Tool. The Hydrogen Abstraction Tool is fabricated by touching the radical at the tip of the Adamantane Radical Tool to a C2 dimer on a suitable presentation surface.

The Methylene Tool. The Adamantane Radical Tool is also used to make the Methylene Tool by touching the radical tip of the Adamantane Radical Tool to a .CH2 group on a suitable presentation surface, in a method analogous to that used during the bootstrap procedure to fabricate the proto-Silicon Methylene tip.

The Germylene Tool and the Proto-Silicon Germanium tip. Next, the Adamantane Radical Tool is used to make a Germylene Tool or the proto-Silicon Radical tip is used to make a proto-Silicon Germanium tip. The Germylene Tool and the proto-Silicon Germanium tip have similar functionality, so the choice about which one to use during the bootstrap sequence depends on specific issues of implementation convenience that will be evident to practitioners skilled in the art.

The Germylene Tool (or the proto-Silicon Germanium tip if fabricated) can be fabricated by touching an Adamantane Radical Tool or a proto-Silicon Radical tip (respectively) to a GeH2 group on a germanium presentation surface, in a fashion similar to the proto-Silicon Methylene tip fabrication sequence illustrated in FIG. 18 but with the .CH2 group 282 replaced by a .GeH2 group.

The Germanium Radical Tool. Either the Germylene Tool or the proto-Silicon Germanium tip can then be used during fabrication of the first Germanium Radical Tool. As the Si—Ge bond is weaker than the C—Ge bond, the build sequence used with the proto-Silicon Germanium tip is simpler than the build sequence used with the Methylene Tool.

Alternatively, the Germanium Radical Tool can be fabricated by a sequence of reactions similar to those described for the Adamantane Radical Tool and illustrated in FIG. 19, with but one exception. The single use of the proto-Silicon Methylene tip that adds the carbon atom destined to be the radical carbon at the tip of the Adamantane Radical Tool is replaced by a single use of either (1) the Germylene Tool or (2) the proto-Silicon Germanium tip, as is convenient. The remaining reactions in the sequence continue as before. As the single use of the Germylene Tool or the proto-Silicon Germanium tip is the only use of either one of these items in the entire build sequence required for the fabrication of the Germanium Radical Tool, the reaction reliability for this single tool application need not be high.

The GermylMethylene and Hydrogen Donation Tools. Once fabricated, the Germanium Radical Tool can be charged by touching it to a .CH2 on a suitable presentation surface, analogous to the previously described methods, producing the first GermylMethylene Tool.

The Germanium Radical Tool can also be used to make the Hydrogen Donation Tool by using the Hydrogen Abstraction recharge reaction illustrated in FIG. 12. The Hydrogen Abstraction Tool must first be used to abstract a hydrogen atom, creating a spent Hydrogen Abstraction Tool 110 requiring recharge. Then the Germanium Radical Tool 130 will bond to the spent Hydrogen Abstraction Tool 110 at the distal carbon atom 102. A second Germanium Radical Tool 224 then abstracts hydrogen 112 from the tip of the spent Hydrogen Abstraction Tool 110 to produce a new Hydrogen Donation Tool 120. The bonded Hydrogen Abstraction Tool 100 and the first Germanium Radical Tool 130 are then separated, regenerating both.

The Hydrogen Transfer and Dimer Placement Tools. As illustrated in FIG. 15, the Hydrogen Transfer Tool is fabricated by bonding a Germanium Radical Tool 130 to a spent Hydrogen Abstraction Tool 110. The Dimer Placement Tool can be made using the previous tools. The entire nine-tool minimal toolset has now been fabricated.

Summary of Bootstrap Process

The particular sequence of bootstrap operations described here is: (1) Proto-Hydrogen Abstraction tip, (2) Proto-Silicon Hydrogen Donation tip, (3) Proto-Silicon Radical tip, (4) Proto-Silicon Methylene tip, (5) Adamantane Radical Tool, (6) Hydrogen Abstraction Tool, (7) Methylene Tool, (8) Germylene Tool, (9) Proto-Silicon Germanium tip (optional), (10) Germanium Radical Tool, (11) GermylMethylene Tool, (12) Hydrogen Donation Tool, (13) Hydrogen Transfer Tool, and (14) Dimer Placement Tool. Other sequences will be apparent to practitioners skilled in the art and having the benefit of the teachings presented herein.

Bootstrapping a set of mechanosynthetic tools requires careful consideration of the reactions involved. It can be simplified by the use of additional reactions, elements, conditions, or mechanisms that are used primarily or only during the bootstrap sequence. For example, if reactions are carried out at low temperature, then reliability problems which are exacerbated by thermal noise and thermally induced errors can be reduced. Low temperature operation also allows the use of alternative reactions that might have unacceptably low reliability at higher temperatures. Auxiliary tips and processes can be introduced to simplify the steps in the bootstrap sequence. The mechanisms for providing feedstock and for disposing of excess atoms can also be chosen to simplify the bootstrap process.

Although critical in the early stages of the development of mechanosynthesis, the bootstrap process is likely to become almost immediately obsolete. Once the bootstrap proto-tools have fabricated any reasonably complete set of atomically-precise mechanosynthetic tools, this complete set of more sophisticated tools can be employed thereafter.

Energy Barriers, Tips and Reaction Design

The foregoing material has described a bootstrap process by which atomically-precise tips can be created from non-atomically-precise tips. In designing other such bootstrap processes, reactions, or tips, some useful guidelines include: use of a rigid tip geometry so that the bonds between the apical atom and the other tip atoms do not deform excessively or break as a feedstock atom is transferred; use of a tip shape and aspect ratio which allows the tip to approach a workpiece and perform the desired reaction without steric hindrance; and use of tip to feedstock bond strengths that facilitate pickup of feedstock from a feedstock depot while not making donation of feedstock to a workpiece problematic, and use of a tip geometry which facilitates holding feedstock at the desired angle relative to the workpiece.

With regards to a rigid tip geometry, a tetrahedral structure with respect to the apical atom can be useful as, with a feedstock atom bound to one leg of the tetrahedron, the other three bonds serve to stabilize the apical atom when force is applied during a reaction. However, other geometries are possible. For example, in addition to VSEPR AX4 (tetrahedral, or other variations of AX4), AX5 and higher hybridizations can also provide the necessary free electrons to bond a feedstock atom while having the ability to form at least three other bonds to create a rigid tip structure. However, the primary concern is simply whether or not a given tip will reliably perform the intended reaction, and certainly working tips can deviate from these suggestions.

To facilitate the design of new tips and reactions by example, and to provide a library of existing reactions, hundreds of different tips and reactions have been designed and vetted at a high degree of simulation precision. The table below describes a large set of tips, capable of transferring many different atoms. The calculations were carried out at the B3LYP/6-311G(d,p) level of theory using the Gausian09 software package with default DFT grid size and convergence criteria. The data include net energy changes and reaction barriers to transferring many different atoms between various adamantane sidewall and bridgehead structures. These adamantine structures are used as representative tip and workpiece structures to demonstrate specific exemplary reactions that have been vetted at a high level of detail. These are certainly not the only structures and reactions that would be obvious given the teachings presented herein, but the reactions listed demonstrate transferring feedstock atoms including: Al, B, Be, Br, C, Cl, F, Ge, H, Ir, Li, Mg, N, Na, O, P, S, and Si.

With respect to the reactions in Table 1, the tip always approached the workpiece coaxially. The coaxial trajectory has been found to be widely-applicable and robust. This fact, along with the extensive data provided, should enable the facile design of a vast number of related reactions. Also, (Tarasov, Akberova et al., "Optimal Tooltip Trajectories in a Hydrogen Abstraction Tool Recharge Reaction Sequence for Positionally Controlled Diamond Mechanosynthesis," J. Comput. Theor. Nanosci., 2, 2010) teaches a process that may be used to determine other trajectories, and we incorporate by reference this material.

In the table below, "Tip" is the donating structure, "FS" (feedstock) is the atom being transferred, "Workpiece" is the structure to which the feedstock is transferred, "Delta (eV)" indicates the change in energy for the reaction, and "Barrier (eV)" indicates the reaction barrier.

"300K" is the probability of reaction failure at 300 Kelvin (room temperature), while "77K" is the probability at 77 Kelvin (liquid nitrogen temperature). Scientific notation is used due to the very small numbers. These calculations were performed using the formulas disclosed in Code Listing 1. 300K and 77K are representative temperatures only. Any temperature at which the reactions are reliable enough for a given purpose could be used, but it is noteworthy that most of the reactions listed would have over 99.99% reliability even at room temperature.

With respect to the structures, C9H14[Al,B,N,P] have the apical atom, to which the feedstock atom is attached, at the sidewall position of an adamantane frame. C9H15[C,Si,Ge] have the apical atom, to which the feedstock atom is attached, at the bridgehead position of an adamantane frame. The notation for the workpieces are the same, except that the apical atoms are listed first. For example, the reaction where a C914Al tip using a Be feedstock atom donates the feedstock atom to CC9H15 could be expressed as:

AdamantaneSidewall-Al—Be.+.C-AdamantaneBridgeHead->AdamantaneSidewall-Al.+.Be—C-AdamantaneBridgeHead

TABLE 1

Element Transfers with Energy Calculations and Reliabilities at Various Temperatures

| Tip | FS | Workpiece | Delta (eV) | Barrier (eV) | 77 K | 300 K |
|---|---|---|---|---|---|---|
| C9H14Al | Al | CC9H15 | −0.64 | 0.02 | 1.15E−42 | 1.72E−11 |
| C9H14Al | B | NC9H14 | −3.40 | 0.00 | 1.18E−222 | 1.09E−57 |
| C9H14Al | Be | CC9H15 | −1.46 | 0.00 | 2.39E−96 | 2.87E−25 |
| C9H14Al | Be | NC9H14 | −2.71 | 0.00 | 1.14E−177 | 3.84E−46 |
| C9H14Al | H | BC9H14 | −1.05 | 0.15 | 4.94E−69 | 2.94E−18 |
| C9H14Al | H | CC9H15 | −0.90 | 0.22 | 1.77E−59 | 8.32E−16 |
| C9H14Al | H | SiC9H15 | −0.49 | 0.23 | 1.06E−32 | 6.21E−09 |
| C9H14Al | Li | NC9H14 | −0.76 | 0.00 | 1.30E−50 | 1.57E−13 |
| C9H14Al | Mg | BC9H14 | −0.22 | 0.00 | 2.48E−15 | 1.78E−04 |
| C9H14Al | Mg | NC9H14 | −0.61 | 0.00 | 1.53E−40 | 6.04E−11 |
| C9H14Al | N | BC9H14 | −1.73 | 0.04 | 6.14E−114 | 8.75E−30 |
| C9H14Al | P | BC9H14 | −0.75 | 0.14 | 1.47E−49 | 2.93E−13 |
| C9H14Al | P | NC9H14 | −0.42 | 0.00 | 4.85E−28 | 9.76E−08 |
| C9H14Al | P | SiC9H15 | −0.21 | 0.00 | 3.30E−14 | 3.47E−04 |
| C9H14Al | S | BC9H14 | −0.90 | 0.00 | 2.69E−59 | 9.27E−16 |
| C9H14B | Al | CC9H15 | −0.13 | 0.00 | 3.72E−09 | 6.86E−03 |
| C9H14B | Be | NC9H14 | −1.26 | 0.00 | 4.21E−83 | 7.19E−22 |
| C9H14B | Li | NC9H14 | −0.78 | 0.00 | 5.61E−52 | 7.01E−14 |
| C9H14B | Na | NC9H14 | −0.13 | 0.00 | 3.15E−09 | 6.58E−03 |
| C9H14N | Br | AlC9H14 | −2.48 | 0.00 | 7.75E−163 | 2.46E−42 |
| C9H14N | S | AlC9H14 | −0.65 | 0.02 | 1.95E−43 | 1.09E−11 |
| C9H14N | S | BC9H14 | −1.55 | 0.00 | 5.25E−102 | 1.01E−26 |
| C9H14N | S | SiC9H15 | −0.41 | 0.11 | 2.18E−27 | 1.44E−07 |
| C9H14P | Al | NC9H14 | −1.67 | 0.07 | 6.91E−110 | 9.60E−29 |
| C9H14P | Mg | AlC9H14 | −0.05 | 0.00 | 6.87E−04 | 1.54E−01 |
| C9H14P | Mg | BC9H14 | −0.27 | 0.02 | 1.71E−18 | 2.75E−05 |
| C9H14P | P | BC9H14 | −0.87 | 0.07 | 1.31E−57 | 2.51E−15 |
| C9H15C | Br | AlC9H14 | −1.23 | 0.01 | 3.73E−81 | 2.27E−21 |
| C9H15C | Br | BC9H14 | −1.50 | 0.00 | 1.44E−98 | 7.71E−26 |
| C9H15C | Br | GeC9H15 | −0.60 | 0.06 | 5.25E−40 | 8.28E−11 |
| C9H15C | Br | SiC9H15 | −1.01 | 0.04 | 1.27E−66 | 1.22E−17 |
| C9H15C | Cl | AlC9H14 | −1.22 | 0.17 | 9.07E−81 | 2.86E−21 |
| C9H15C | Cl | BC9H14 | −1.62 | 0.18 | 8.02E−107 | 5.87E−28 |
| C9H15C | Cl | GeC9H15 | −0.52 | 0.32 | 1.27E−34 | 2.00E−09 |
| C9H15C | Cl | SiC9H15 | −1.02 | 0.21 | 1.29E−67 | 6.79E−18 |
| C9H15C | Li | NC9H14 | −1.06 | 0.00 | 6.19E−70 | 1.72E−18 |
| C9H15C | Mg | NC9H14 | −0.61 | 0.00 | 8.90E−41 | 5.25E−11 |
| C9H15C | O | BC9H14 | −2.68 | 0.00 | 1.58E−175 | 1.36E−45 |
| C9H15C | S | AlC9H14 | −0.88 | 0.00 | 2.90E−58 | 1.71E−15 |
| C9H15C | S | BC9H14 | −1.78 | 0.00 | 7.93E−117 | 1.59E−30 |
| C9H15C | S | GeC9H15 | −0.24 | 0.00 | 2.11E−16 | 9.47E−05 |
| C9H15C | S | NC9H14 | −0.23 | 0.00 | 1.49E−15 | 1.56E−04 |
| C9H15C | S | SiC9H15 | −0.63 | 0.00 | 3.25E−42 | 2.25E−11 |
| C9H15Ge | Br | AlC9H14 | −0.63 | 0.11 | 7.10E−42 | 2.75E−11 |
| C9H15Ge | Br | BC9H14 | −0.90 | 0.14 | 2.73E−59 | 9.31E−16 |
| C9H15Ge | Br | SiC9H15 | −0.41 | 0.21 | 2.39E−27 | 1.47E−07 |
| C9H15Ge | C | CC9H15 | −1.15 | 0.00 | 9.46E−76 | 5.54E−20 |
| C9H15Ge | C | SiC9H15 | −0.46 | 0.00 | 7.39E−31 | 1.85E−08 |
| C9H15Ge | Cl | AlC9H14 | −0.71 | 0.31 | 7.12E−47 | 1.43E−12 |
| C9H15Ge | Cl | SiC9H15 | −0.51 | 0.47 | 1.00E−33 | 3.39E−09 |
| C9H15Ge | F | AlC9H14 | −1.08 | 0.01 | 2.00E−71 | 7.15E−19 |
| C9H15Ge | F | BC9H14 | −1.79 | 0.18 | 1.19E−117 | 9.76E−31 |
| C9H15Ge | Ge | CC9H15 | 0.02 | 0.00 | 6.18E−02 | 4.89E−01 |
| C9H15Ge | H | SiC9H15 | −0.35 | 0.23 | 1.12E−23 | 1.29E−06 |

TABLE 1-continued

Element Transfers with Energy Calculations and Reliabilities at Various Temperatures

| Tip | FS | Workpiece | Delta (eV) | Barrier (eV) | 77 K | 300 K |
|---|---|---|---|---|---|---|
| C9H15Ge | Li | NC9H14 | −0.46 | 0.00 | 1.62E−30 | 2.26E−08 |
| C9H15Ge | O | BC9H14 | −2.96 | 0.00 | 3.94E−194 | 2.29E−50 |
| C9H15Ge | O | SiC9H15 | −0.96 | 0.00 | 9.41E−64 | 6.66E−17 |
| C9H15Ge | P | BC9H14 | −0.79 | 0.03 | 5.05E−52 | 6.82E−14 |
| C9H15Ge | S | BC9H14 | −1.54 | 0.15 | 3.71E−101 | 1.67E−26 |
| C9H15Ge | Si | CC9H15 | −0.21 | 0.00 | 3.21E−14 | 3.44E−04 |
| C9H15Si | Al | CC9H15 | −0.25 | 0.02 | 4.97E−17 | 6.54E−05 |
| C9H15Si | B | CC9H15 | −1.12 | 0.14 | 4.39E−74 | 1.48E−19 |
| C9H15Si | Br | BC9H14 | −0.49 | 0.43 | 1.13E−32 | 6.31E−09 |
| C9H15Si | H | BC9H14 | −0.56 | 0.27 | 4.65E−37 | 4.73E−10 |
| C9H15Si | Li | NC9H14 | −0.57 | 0.00 | 5.33E−38 | 2.71E−10 |
| C9H15Si | P | BC9H14 | −0.54 | 0.16 | 4.44E−36 | 8.44E−10 |
| C9H15Si | S | BC9H14 | −1.14 | 0.00 | 2.44E−75 | 7.07E−20 |
| C9H15Si | Si | CC9H15 | −0.11 | 0.00 | 6.11E−08 | 1.41E−02 |
| C9H15Si | Ge | CC9H15 | −0.08 | 0.00 | 5.83E−06 | 4.53E−02 |
| C9H15Ge | Ir | CC9H15 | −0.04 | 0.00 | 1.97E−03 | 2.02E−01 |
| C9H15Ge | Ir | SiC9H15 | −0.33 | 0.00 | 1.82E−22 | 2.63E−06 |
| C9H15C | Ir | SiC9H15 | −0.29 | 0.00 | 9.36E−20 | 1.31E−05 |
| C9H15C | Ir | BC9H14 | −1.07 | 0.00 | 6.78E−71 | 9.77E−19 |

Note that it is possible for the change in energy (eV) to be positive. This is due to the fact that energy and force are not equivalent. A mechanosynthetic tip may exert force over a distance that results in a net change in energy which is positive, even if the reaction product resides in a local energy minima.

Bond Strain in Tip, Reaction and Workpiece Design. A number of strain types exist, such as Van der Waals, stretch, torsion, and angle (or "bend," including ring) strain. In aggregate the various types of strain are often referred to as "steric energies," and these steric energies, or strain, are known to influence molecular stability and chemical reaction energetics.

For example, cyclobutane, with 7.5% kcal/mol/bond strain, is more reactive than the larger cycloalkanes or a straight chain hydrocarbon, in which the ring strain is relaxed. Fullerenes are similarly affected by bond strain. Since the lowest energy configuration for individual fullerene units is planar, higher curvatures generally lead to more reactive molecules due at least in part, to angle strain. To pick a round number, 5% strain is perhaps where marked differences in reactivity and other properties would start to be apparent.

Note that overall, a molecule could have very little strain, but one or more strained bonds can still cause it to be highly reactive, so the distribution of strain is also important. Conversely, a molecule could have many bonds which are only slightly strained (perhaps less than the 5% figure), yet when accumulated across multiple bonds, the overall strain energy is substantial. In such cases, modest amounts of strain on per-bond basis can lead to substantial effects on molecule conformation and various other properties. Using strain to alter bond strength is discussed in more detail herein.

One scenario is that of feedstock held to a tip by a single bond. Strain within the tip may be used to change the bond angles, and thereby energies, of the apical tip atom to the feedstock. For example, consider an adamantane structure where a bridgehead carbon is bonded to the feedstock. This bridgehead carbon would normally be bonded to three other carbons, and the uniform length of the carbon-carbon bonds throughout the adamantane structure allows the bridgehead carbon to achieve a perfect tetrahedral configuration where each bond to the bridgehead carbon is about 109.5 degrees. However, if a Ge atom is substituted for each of the three carbons to which the bridgehead carbon is attached, the Ge—C-feedstock angle becomes about 112.9 degrees, causing angle strain.

Other type of strain can also be employed. For example, Van der Waals strain can be created by replacing, e.g., H atoms with larger diameter atoms of the same valence, adjacent to the feedstock. However, Van der Waals strain is easier to create with larger structures, as additional, relatively inflexible, anchor points can be created and used to position one or more strain-causing atoms close enough to the feedstock that their Van der Waals radii overlap, even though the strain causing atom(s) are not bonded to the feedstock.

While a tip designed in this manner can cause Van der Waals strain by having two or more parts of the same tip interfere (where one part is the feedstock site and the other part is a portion of the tip designed to at least partially impinge upon the feedstock location), a second tip could also be used to apply mechanical force to feedstock. For example, consider a first tip with feedstock bound to it. Using a second tip to apply force to the feedstock perpendicularly to its point of attachment could weaken the bond between the first tip and the feedstock. This is conceptually similar to building such strain into a single tip, but more versatile as the timing, amount of force, and angle of force application can all be varied.

Another scenario where strain could be employed is when feedstock is held by more than one bond to a tip. To reduce tip bond strength to the feedstock, the bonding points can be pulled apart until the bonds are strained by the desired amount. This is more easily illustrated in a slightly larger structure than a single adamantane, so that rigidity of the tip backbone can be used to create strain without excessive deformation. For example, the native distance between two methyl groups connected by an oxygen (3HC—O—CH3) is about 2.36 A, and the angle is about 110.7 degrees. However, due to the lattice spacing, this configuration cannot be obtained on (111) diamond. If two adjacent carbons on the (111) face of diamond each have a hydrogen removed, and an oxygen atom is then bound to those carbons, with a very small structure composed of 3 interlocked adamantanes (larger structures would likely allow less deformation of the tip backbone), the oxygen becomes bound to the two carbons at an angle of about 87.8 degrees with the carbons being spaced about 2.02 A apart. Clearly, this is a substantial distortion of the minimal energy configuration and so if the oxygen is the feedstock, it will require less energy to remove from the tip structure than if it were bound in a configuration closer to its energy minima. Substitutions could be used to alter the diamond lattice spacing to increase or decrease the amount of strain created. An analogous technique could be used by a single feedstock moiety held by more than one tip. The tip spacing could be used to adjust tip-feedstock bond strength, and this could be changed on-the-fly if desired.

Note that with one single bond, as they are free to rotate, torsion is generally irrelevant. But, if a feedstock moiety was multiply-bonded, or one or more, e.g., double bonds (or any bond type not free to rotate), were used to bind the feedstock to one or more tips, or one or more points on a single tip, torsion could also be used to create strain, and could any other well-known strain-inducing modifications.

Many of the same techniques could be employed on the workpiece. In some cases, modulating bond strength on the workpiece instead of, or in addition to, the tip may be convenient. And, build sequence order can be chosen to create intermediate structures with strain if this alters the reactivity favorably.

It should be noted that creating strain and releasing strain are two sides of the same effect. If one considers a strained structure the default structure, releasing strain could be used to, for example, strengthen, instead of weaken, bonds. Further, strain levels need not be static. Levels of strain could be changed curing the course of a reaction. For example, to increase tip affinity when picking up feedstock, and then decreasing tip affinity when releasing feedstock.

Workpiece Specification and Build Sequences

The ability to create atomically-precise tips from non-atomically-precise tips via a bootstrap process has been described in detail herein. And, reaction energetics and reliabilities from detailed simulations have been reported which, when coupled with the teachings presented herein, would enable one skilled in the art to make many tips sufficient for carrying out many reactions. With those tips and reactions available, to facilitate building a workpiece, once must define the workpiece in an atomically-precise manner, and then create a build sequence for assembling the workpiece.

One defines a workpiece for mechanosynthesis by specifying each atom in the workpiece and its atomic coordinates, directly or indirectly (for example, via an algorithm which generates the desired structure). Many computational chemistry programs allow the creation of models based on atomic coordinates, or algorithms to generate such coordinates.

Once the atomic coordinates have been specified, a build sequence can be created that specifies the order in which each atom is to be added to, or removed from, the workpiece. Reactions that do not add or remove atoms are also possible, such as those that change the bonding structure of the workpiece. For each reaction, the reaction parameters, such as the tip structure to use, tip trajectory, feedstock, reaction temperature, reaction energetics and possible reaction pathologies can be determined. These topics are addressed herein. Where additional reactions are desired beyond those described, it will be obvious to one skilled in the art how to determine new reactions using the teachings and data herein as a guide.

Exemplary Workpiece Specification and Build Sequence

The following illustrates the use of a build sequence for the manufacture of a pyramidal diamondoid structure in two forms (one capped with C, one capped with Ge). This structure has multiple uses. With the apical Ge atom, it can serve as a Germanium Radical tool. Terminated with a carbon ring-closure reaction, omitting the Ge, the structure can serve as an Adamantane Radical tool. And, given the size and stepped nature of the walls, such a structure (or multiple such structures built a known distance apart) could serve as calibration standards for SFM or AFM-based metrology.

This build sequence was computed using the representative density functional method with the B3LYP/6-311G** basis set, which typically provides a good tradeoff between accuracy and computational expense. Higher reaction accuracies could be obtained using more computationally-demanding techniques such as coupled clusters. (Lee, Scuseria et al., "Achieving Chemical Accuracy with Coupled-Cluster Theory," Quantum Mechanical Electronic Structure Calculations with Chemical Accuracy, Kluwer Academic Publisher, 1995) 4 degrees Kelvin was assumed for this sequence (readily accessible with liquid helium) although the reactions would likely prove reliable at higher temperatures.

Required Tools. The tools used in this build sequence are described in detail elsewhere herein. They are: the Hydrogen Abstraction tool (HAbst), the Hydrogen Donation tool (HDon), the Germanium Radical tool (GeRad), and the GermylMethylene tool (GM).

Required Reactions. The following reactions are used, along with the specified tools, in the building of this workpiece. In the reaction names, a reaction starting with "C" indicates a "Capping" reaction, an "M" indicates a methylating reaction, an "R" indicates a "Row Building" reaction, a "G" indicates reactions specific to capping the pyramid with Ge versus C, and a "P" is a possible pathology.

Note that there are various ways of dealing with pathologies, including avoiding them through build sequence design, fixing them in the sense of reversing the last reaction and trying again, or accepting the pathology and altering the build sequence to account for it. In this build sequence, the latter strategy is used. There are 6 possible pathologies, each of which are associated with a different modification to the build sequence which accounts for that specific pathology, so that no matter what pathology occurs, the end product is the same. In this sequence, the end result of one pathology reaction may be another pathology. Testing of some kind, such as via scanning the workpiece with tradition AFM or SPM-like techniques after reactions with possible pathologies is assumed. This results in knowledge of which pathology occurred, and the appropriate sequence can be followed. Not all pathologies can occur in all situations, and so do not always have to be tested for. In a build sequence, a designation such as [P1] indicates that a test for the P1 pathology should be done, and if the P1 pathology has occurred, the sequence for that pathology should be followed. If not, continue with the other stated reactions.

The related structures for each reaction may show only the atoms proximate to the reaction, rather than the entire workpiece. Recharge reactions are not included, but are presumed to be used as needed, as described in detail elsewhere herein. Tips are not shown as part of the reaction structures, but are listed with each reaction description.

TABLE 2

Pyramid Build Sequence Reactions

| Reaction | Description | Tip(s) Required | Sample Starting Structure File | Sample Ending Structure File |
| --- | --- | --- | --- | --- |
| M1 | First step in methylating an outer edge carbon site, via abstracting the hydrogen from the carbon with HAbst, for the subsequent addition of a radical methyl group. | HAbst | M1_a_C110.hin | M1_b_C110Rad.hin |
| M2 | Second step in methylating an outer edge carbon site, via donating the radical methyl group to the radical carbon site with GM, for subsequent hydrogenation. | GM | M2_a_C110Rad.hin | M2_b_C110CH2.hin |
| M3 | Final step in methylating an outer edge carbon site, via donating a hydrogen to the radical methyl group with HDon. | HDon | M3_a_C110CH2.hin | M3_b_C110CH3.hin |
| M4 | First step in methylating a non-outer edge carbon site adjacent to a methylated outer edge carbon site, via abstracting the hydrogen from the carbon with HAbst. | HAbst | M4_a_C110CH3.hin | M4_b_C110RadCH3.hin |
| M5 | Second step in methylating a non-outer edge carbon site adjacent to a methylated outer edge carbon site, via donating a radical methyl group to the radical carbon site with GM, for subsequent hydrogenation. | GM | M5_a_C110RadCH3.hin | M5_b_C110CH3CH2.hin |
| M6 | Final step in methylating a non-outer edge carbon site adjacent to a methylated outer edge carbon site, via donating a hydrogen to the radical methyl group with HDon. | HDon | M6_a_C110CH3CH2.hin | M6_b_C110CH3CH3.hin |
| M7 | First step in methylating a non-outer edge carbon site adjacent to a methylated non-outer edge carbon site, via abstracting the hydrogen from the carbon with HAbst, for the subsequent addition of a radical methyl group. | HAbst | M7_a_C110CH3CH3.hin | M7_b_C110RadCH3CH3.hin |
| M8 | Second step in methylating a non-outer edge carbon site adjacent to a methylated non-outer edge carbon site, via donating a radical methyl group to the radical carbon site with GM, for subsequent hydrogenation. | GM | M8_a_C110RadCH3CH3.hin | M8_b_C110CH3CH3CH2.hin |
| R1 | Ring closure step between a methyl group on an outer edge carbon site and a radical methyl group on a non-outer edge carbon site, via abstracting a hydrogen from the methyl group with HAbst, allowing radical-radical coupling to form a 6-member ring. | HAbst | R1_a_C110CH2CH3.hin | R1_b_C110Ring.hin |

TABLE 2-continued

Pyramid Build Sequence Reactions

| Reaction | Description | Tip(s) Required | Sample Starting Structure File | Sample Ending Structure File |
|---|---|---|---|---|
| R2 | First step in extending a C110 row, via abstracting a hydrogen from non-outer edge carbon with HAbst, for the subsequent addition of a radical methyl group. | HAbst | R2_a_C110Ring.hin | R2_b_C110RadRing.hin |
| R3 | Second step in extending a C110 row, via donating a radical methyl group to the radical carbon site with GM, for the subsequent ring closure step. | GM | R3_a_C110RadRing.hin | R3_b_C110CH2Ring.hin |
| R4 | Final step in extending a C110 row, via abstracting a hydrogen from the existing adjacent 6-member ring with HAbst, allowing for radical-radical coupling to close another 6-member ring. | HAbst | R4_a_C110CH2Ring.hin | R4_b_C110RowExt.hin |
| C1 | First step in methylating a non-outer edge carbon site, via abstracting the hydrogen from the carbon with HAbst, for the subsequent addition of a radical methyl group. | HAbst | C1_a_C110.hin | C1_b_C110Rad.hin |
| C2 | Second step in methylating a non-outer edge carbon site, via donating the radical methyl group to the radical carbon site with GM, for subsequent hydrogenation. | GM | C2_a_C110Rad.hin | C2_b_C110CH2.hin |
| C3 | Final step in methylating a non-outer edge carbon site, via donating a hydrogen to the radical methyl group with HDon. | HDon | C3_a_C110CH2.hin | C3_b_C110CH3.hin |
| C4 | First step in methylating a non-outer edge carbon site adjacent to a methylated non-outer edge carbon site, via abstracting the hydrogen from the carbon with HAbst, for the subsequent addition of a radical methyl group. | HAbst | C4_a_C110CH3.hin | C4_b_C110RadCH3.hin |
| C5 | Second step in methylating a non-outer edge carbon site adjacent to a methylated non-outer edge carbon site, via donating a radical methyl group to the radical carbon site with GM, for subsequent hydrogenation. | GM | C5_a_C110RadCH3.hin | C5_b_C110CH3CH2.hin |
| C6 | Ring closure step between radical methyl group on a non-outer edge carbon site and a methyl group on a non-outer edge carbon site, via abstracting a hydrogen from the methyl group with HAbst, allowing radical-radical coupling to form a 6-member ring. | HAbst | C6_a_C110CH3CH2.hin | C6_b_C110Ring.hin |
| G1 | First step in Ge capping via donating a radical GeH2 group to a radical methyl group on a non-outer edge carbon site with GeRad, for subsequent ring closure. | GeRad | G1_a_C110CH3CH3CH2.hin | G1_b_C110CH3CH3CH2GeH2.hin |
| G2 | Second step in Ge capping via abstracting a hydrogen from a methyl group on a non-outer edge carbon site with HAbst, allowing for radical-radical coupling to close a 7-member ring on the C110 ridge. | HAbst | G2_a_C110CH3CH3CH2GeH2.hin | G2_b_C110CH3CGeH2CRing.hin |
| G3 | Third step in Ge capping via abstracting a hydrogen from the third methyl group on a non-outer edge carbon site adjacent to the 7-member ring spanning the C110 ridge with HAbst, for subsequent cage closure. | HAbst | G3_a_C110CH3CGeH2CRing.hin | G3_b_C110CH2CGeH2CRing.hin |
| G4 | Final step in Ge capping via abstracting a hydrogen from the Ge of the 7-member ring spanning the C110 ridge via HAbst, allowing for radical-radical coupling to for the final bond to Ge. | HAbst | G4_a_C110CH2CGeH2CRing.hin | G4_b_C110GeRadH.hin |
| G5 | Donation of GeH group from GeRad to a surface CH2 radical group. | GeRad | G5_a_C110CH3CH3CH2.hin | G5_b_C110CH3CH3CH2GeH.hin |
| G6 | Donation of Ge group from GeRad to a surface CH2 radical group. | GeRad | G6_a_C110CH3CH3CH2.hin | G6_b_C110CH3CH3CH2Ge.hin |

TABLE 2-continued

Pyramid Build Sequence Reactions

| Reaction | Description | Tip(s) Required | Sample Starting Structure File | Sample Ending Structure File |
|---|---|---|---|---|
| G7 | Ring closure via abstracting a hydrogen from a CH3 group with HAbst, resulting in radical-radical coupling of the CH2 and GeH radical groups. | HAbst | G7_a_C110CH3CH3CH2GeH.hin | G7_b_C110_CH3CGeHCRing.hin |
| G8 | Ring closure via abstracting a hydrogen from a CH3 group, resulting in radical-radical coupling of the CH2 and Ge radical groups. | HAbst | G8_a_C110CH3CH3CH2Ge.hin | G8_b_C110CH3CGeCRing.hin |
| G9 | Cage closure via abstracting a hydrogen from a CH3 group, resulting in radical-radical coupling of the CH2 and GeH radical groups. | HAbst | G9_a_C110CH3CGeHCRing.hin | G9_b_C110GeRadH.hin |
| G10 | Cage closure via abstracting a hydrogen from a CH3 group, resulting in radical-radical coupling of the CH2 and Ge radical groups. | HAbst | G10_a_C110CH3CGeCRing.hin | G10_b_C110GeRad.hin |
| P1 | Potential pathology where a hydrogen from GeRad-GeH2 is donated to a surface CH2 radical group instead of the preferred donation of the entire GeH2 group. This creates a GeRad-GeH tip. | GeRad | P1_a_C110CH3CH3CH2.hin | P1_b_C110CH3CH3CH3.hin |
| P2 | Potential pathology where a hydrogen from the GeRad-GeH is donated to a surface CH2 radical group instead of the preferred donation of the entire GeH group. This creates a GeRad-Ge tip. | GeRad | P2_a_C110CH3CH3CH2.hin | P2_b_C110CH3CH3CH3.hin |
| P3 | Potential pathology where a hydrogen migrates from a GeH2 group to a newly created CH2 radical group (created via abstracting a hydrogen from the CH3 group with HAbst) instead of creating a C—Ge bond via radical-radical coupling. | HAbst | P3_a_C110CH3CH3CH2GeH2.hin | P3_b_C110CH3CH3CH2GeH.hin |
| P4 | Potential pathology where a hydrogen migrates from a GeH group to a newly created CH2 radical group (created via abstracting a hydrogen from the CH3 group with HAbst) instead of creating a C—Ge bond via radical-radical coupling. | HAbst | P4_a_C110CH3CH3CH2GeH.hin | P4_b_C110CH3CH3CH2Ge.hin |
| P5 | Potential pathology where a hydrogen migrates from a GeH2 group within a ring to a newly created CH2 radical group (created by abstracting a hydrogen from the neighboring CH3 group with HAbst). | HAbst | P5_a_C110CH3CGeH2CRing.hin | P5_b_C110CH3CGeHCRing.hin |
| P6 | Potential pathology where a hydrogen migrates from the GeH group within a ring to a newly created CH2 radical group (created by abstracting a hydrogen from the neighboring CH3 group with HAbst). | HAbst | P6_a_C110CH3CGeHCRing.hin | P6_b_C110CH3CGeCRing.hin |

Order of Reactions. A pyramid structure can be built using the following build sequences, where one or more reactions surrounded by parenthesis, such as (R2->R3->R4) means to repeat the enclosed reactions as many times as necessary (e.g., this could vary depending on the length of the rows and the height of the pyramid). Parenthesis may be nested, as in (C1->C2->C3->C4->C5->C6->(R2->R3->R4)).

For diversity, two different final products are shown: A pyramid with the apical atom being a carbon, and a version where the apical atom is a germanium. The build sequences differ substantially although the different sequences only change one atom.

TABLE 3

Order of Pyramid Reactions

| Phase | Sequence | Sample Starting Structure File | Sample Ending Structure File |
|---|---|---|---|
| Generating C110 Rows | C1 -> C2 -> C3 -> C4 -> C5 -> C6 -> (R2 -> R3 -> R4) | 1_C110Pyr_RowGen_Begin.hin  2_C110Pyr_RowGen_1stCages.hin | 2_C110Pyr_RowGen_1stCages.hin  3_C110Pyr_RowGen_1stRow.hin |
| Generating layers | (C1 -> C2 -> C3 -> C4 -> C5 -> C6 -> (R2 -> R3 -> R4)) | 4_C110Pyr_RowGen_MidRow.hin | 5_C110Pyr_RowGen_Layered.hin |

TABLE 3-continued

Order of Pyramid Reactions

| Phase | Sequence | Sample Starting Structure File | Sample Ending Structure File |
|---|---|---|---|
| Capping with C | C1 -> C2 -> C3 -> C4 -> C5 -> C6 | 6_C110Pyr_Pyramid_Begin.hin | 7_C110Pyr_Pyramid_End.hin |
| Capping with Ge | M1 -> M2 -> M3 -> M4 -> M5 -> M6 -> M7 -> M8 -> G1[P1] -> G2[P3] -> G3[P5] -> G4[P6] | 8_C110Pyr_GeRad_Begin.hin | 9_C110Pyr_GeRad_End.hin |
| If P1: | G5[P2] -> G7[P4] -> G9[P6] | See respective reactions | See respective reactions |
| If P2: | G6 -> G8 -> G10 | See respective reactions | See respective reactions |
| If P3: | G7[P4] -> G9[P6] | See respective reactions | See respective reactions |
| If P4: | G8 -> G10 | See respective reactions | See respective reactions |
| If P5: | G9[P6] | See respective reactions | See respective reactions |
| If P6: | G10 | See respective reactions | See respective reactions |

Workpiece Specification and Build Sequence Summary. The foregoing material describes how a workpiece can be specified, and provides a pyramidal structure as an exemplary workpiece. The tools which would be required to build this workpiece are listed, as are all the individual reactions, and the order in which these reactions are used to build the pyramid, in two different variants, including one where pathologies are known to be possible. One way in which these pathologies can be surmounted is presented.

Subsequently, these and other processes are described at a higher level of abstraction to aid the reader in understanding the general strategy of specifying and building any workpiece.

Process Overview

To aid in the understanding of the general process of creating a workpiece, FIGS. 20 through 23 provide flow charts of various processes relating to the invention. Note that these flow charts provide only an exemplary embodiment and are in no way intended to limit the invention. Many variations on these processes are possible, and even without changing the steps involved, one might change the decision logic or loop through some processes more than once. For example, to optimally design a workpiece for manufacturability (20-2) may require an iterative process where the workpiece design is revised based on the outcome of subsequent steps or processes, such as the reaction design process described in FIG. 21.

Figure 20:
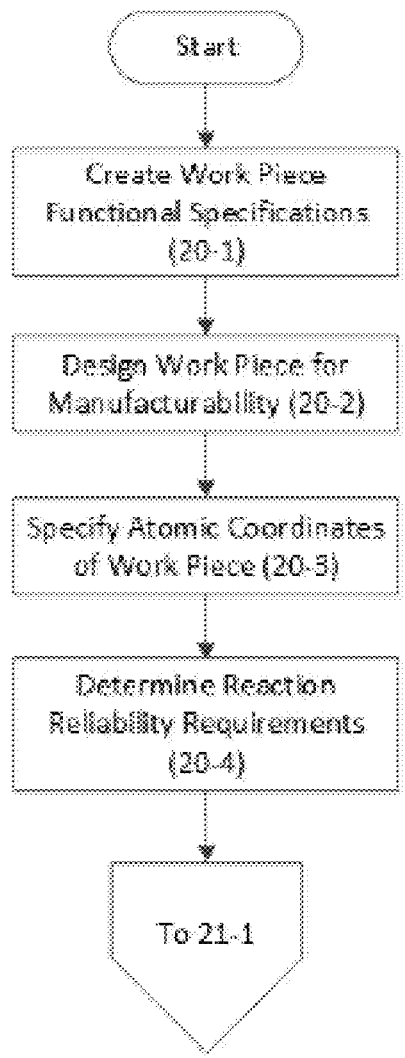
FIG. 20 shows a flow chart for workpiece specification.

The process can be started in FIG. 20 at step (20-1), "Create Workpiece Functional Specifications." This step is similar to that for any traditionally-manufactured product in that product requirements must be defined before the product can be designed from an engineering perspective.

Step (20-2), "Design Workpiece for Manufacturability" also has an analog in traditional manufacturing. The product must be designed with the limitations of the manufacturing process in mind. In the case of mechanosynthesis, this means that a device is preferably designed with elements and bonding patterns whose properties are understood, for which tips and build sequences have been, or can be, designed and are compatible with equipment capabilities, using geometries accessible to the relevant tips, among other limitations which will be obvious to those skilled in the art given the teachings herein.

Once the device has been designed, step (20-3) is to "Specify Atomic Coordinates of Workpiece." That is, define each atom type and its position within the structure. This step may also include determining bonding structure, as this step can be informative although technically redundant since the bonding structure may be fully specified via the atomic coordinates. This may be done in any molecular modeling or computational chemistry software with the appropriate capabilities, such as HyperChem, GROMACS or NAMD.

Step (20-4) "Determine Reaction Reliability Requirements" involves performing an impact analysis of potential defects and the resultant establishment of reaction reliability requirements. Although the goal of mechanosynthesis is the production of atomically-precise products, unintended reactions can occur at frequencies which depend on factors including the chemical reactions being used, the tip design, the reaction trajectory, equipment capabilities and temperature. For each reaction one could analyze the most likely pathological side reactions that might occur and their impact upon the finished workpiece. For example, one could determine the impact of a feedstock atom failing to transfer, a feedstock atom bonding to a workpiece atom adjacent to the intended position, or the workpiece undergoing an unintended rearrangement. The workpiece could be simulated with each potential defect, or more general heuristics or functional testing could be used to determine the likely impact of possible errors in the workpiece.

As an example of how a defect could be insignificant in one context but not in another, consider a simple structural part such as a diamondoid beam: A small number of mistakes may not substantially affect the properties of the finished part, and may not affect the overall product, particularly is the part has been over-engineered to allow for some defects. In such reactions, one might decide that some number of defects were tolerable and therefore require relatively low reaction reliability. On the other hand, if the workpiece being constructed were, for example, a single-molecule transistor that would not function correctly if crucial atoms were misplaced, one might require that such crucial reactions have high reliability.

One alternative to defect impact analysis is to require that each reaction be reliable enough that it is statistically unlikely that the final workpiece contains any errors. This is quite feasible, as will be seen from the reaction reliability calculations presented herein. Also, the ability to correct errors may have an impact on reaction reliability requirements. If errors can be fixed, one might decide to reduce reliability requirements and simply fix errors as they occur.

Figure 21:
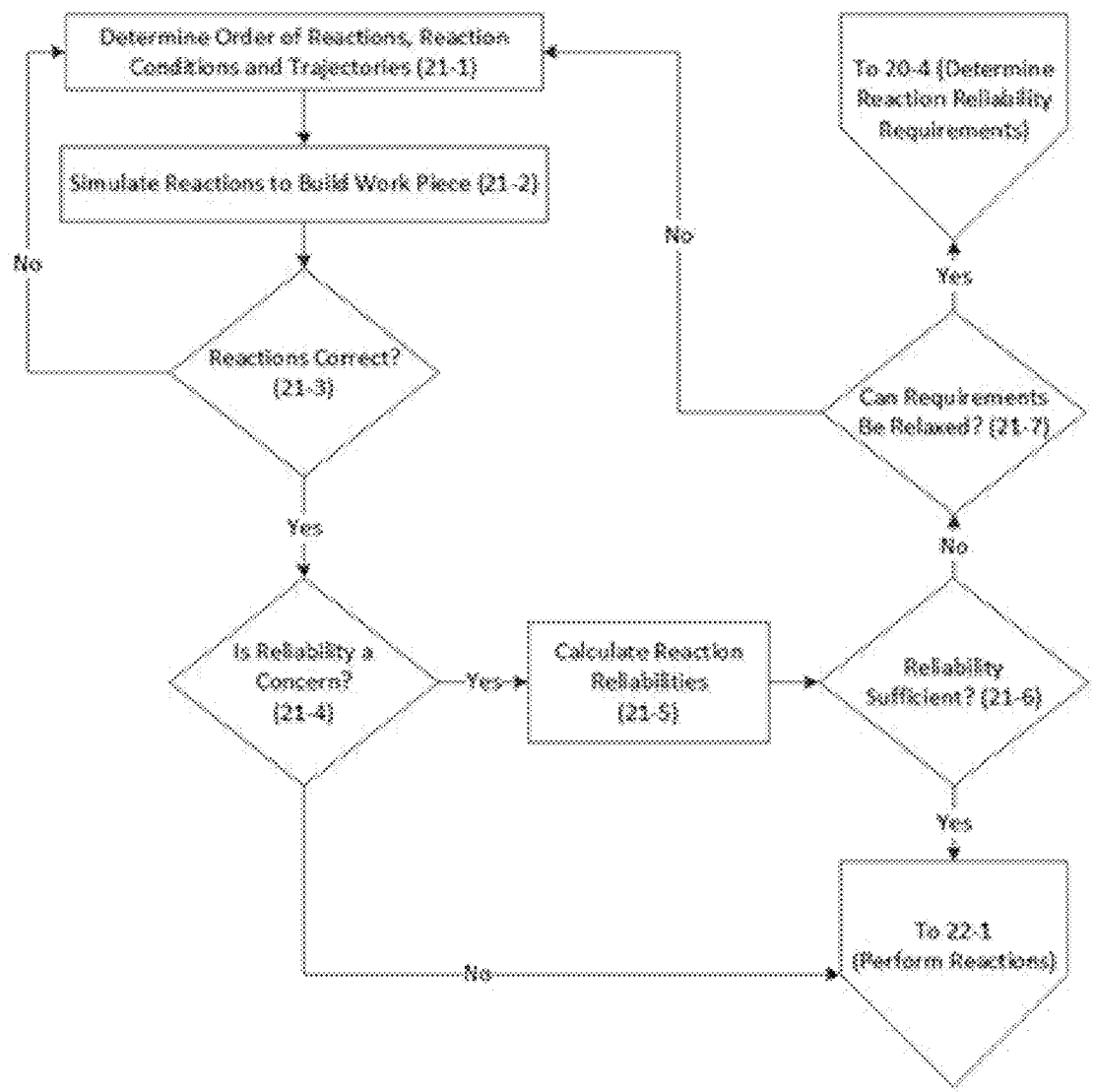
FIG. 21 shows a flow chart for mechanosynthesis reaction design.

FIG. 21 begins with step (21-1) "Determine Order of Reactions, Reaction Conditions and Trajectories." Each atom, as specified in the atomic coordinates of the workpiece, generally (but not necessarily since, for example, one could use dimers or larger molecules as feedstock) requires that a particular reaction be performed on the workpiece to deposit that atom. Abstraction reactions may also be required, as may be reactions which alter the bonding structure of the workpiece without adding or subtracting any atoms.

There may be many different build sequences that would permit the construction of a particular workpiece. Steric constraints will be a major determinant of the order in which atoms are added, as a three-dimensional workpiece requires adding atoms in an order which permits access by the necessary tools for later reactions. The stability of the intermediate structures should also be considered. For example, certain atoms, when left as radicals, might rearrange, forming undesired bonds with adjacent atoms. In addition to a logical order to the addition of atoms, other techniques can be employed to prevent undesired rearrangement. For example, hydrogen atoms can be added to radical sites to temporarily satisfy empty valances, or temperature can be reduced.

When a presumptive build order has been established, the build sequence may be simulated to determine if it works correctly (21-2). The same simulations can test reaction parameters including which tip to use, what temperature is required, and what trajectory a tip will follow. As has been previously noted, lower temperatures will favor accuracy, and unless steric issues make it obvious that a different approach is required, frequently the coaxial trajectory will enable successful reaction completion.

Note that, given that rearrangement and abstraction reactions may be required in a build sequence, workpieces may require more reactions than the number of atoms in the finished workpiece. And, even if this were not the case, workpieces with many atoms will generally require many reactions. If the reactions are being implemented manually, this leads to a substantial requirement for labor. Automating the reaction steps may therefore be desirable. CAD programs can be used to specify AFM trajectories (Chen, "CAD-guided automated nanoassembly using atomic force microscopy-based nonrobotics," IEEE Transactions on Automation Science and Engineering, 3, 2006; Johannes, "Automated CAD/CAM-based nanolithography using a custom atomic force microscope," IEEE Transactions on Automation Science and Engineering, 3, 2006) and atomic force microscopes that are programmable are commercially available, for example using LabVIEW software for control.

Based on the outcome of the simulations, a decision is reached as to whether the reactions as specified are correct (21-3). If not, the sequence is revised. If so, the process proceeds to (21-4) where a decision is made as to whether any of the calculated reactions may pose reliability concerns, for example, based on rearrangements or incorrect reactions that were seen during simulation in (21-2).

In (21-5) the reaction reliabilities can be calculated (for example, by energy barrier calculations or Monte Carlo simulations). (21-6) is a determination as to whether the proposed reaction reliabilities meet production quality needs, and, if the answer to (21-6) is no, (21-7) where requirements are reviewed to see if the build sequence restrictions can be relaxed since they were not met. From (21-7) if the answer is yes, a new iteration is started at (20-4) to determine revised reaction reliability requirements. If the answer to (21-7) is no, alternate reactions, reaction order, reaction trajectories, or reaction conditions can be simulated (21-1) to find a revised build sequence that meets the reaction reliability requirements. If the answer to (21-6) is yes, the process continues in FIG. 22, step (22-1).

Figure 22:
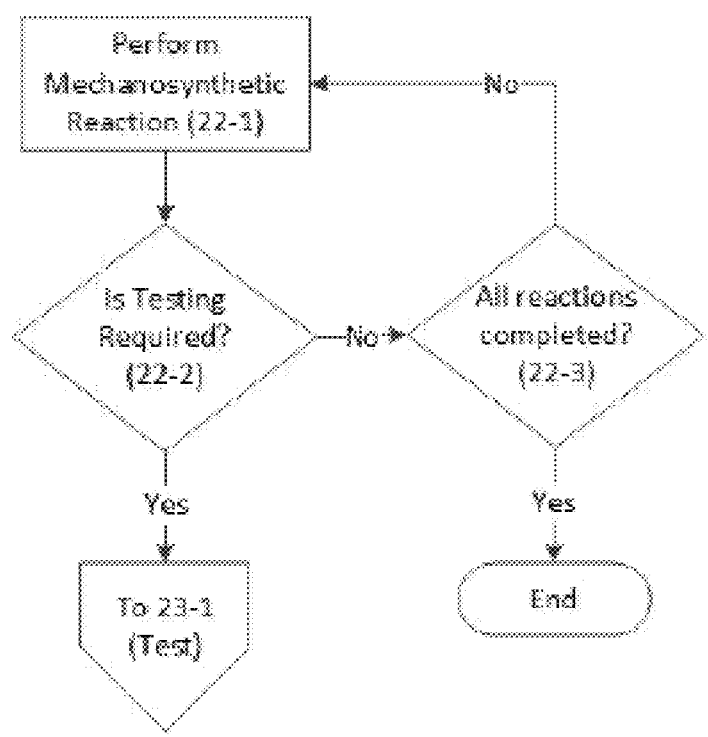
FIG. 22 shows a flow chart for carrying out mechanosynthetic reactions.

FIG. 22 is the Mechanosynthetic Reaction Process. Starting at (22-1) "Perform Mechanosynthetic Reactions," the reactions determined in the build sequence are carried out using SPM/AFM-like equipment, or other suitable equipment. This step involves, whether manually or in a computer-controlled manner, using a positionally-controlled tip to perform each mechanosynthetic reaction in the build sequence. This means picking up a feedstock atom from a presentation surface (or potentially a gaseous or liquid source of feedstock) and bonding it to the workpiece, or removing an atom from the workpiece, or changing the bonding structure of the workpiece without adding or removing an atom. This step would also encompass other reactions, including reactions not involving the workpiece, such as tip refresh or pre-reaction feedstock manipulation as may be necessary.

Step (22-2) is a decision point. If testing is not required, a decision point is reached (22-3) which depends on whether all reactions in the build sequence have been completed. If not, reactions are repeated until the answer is yes, at which point the workpiece is complete. If testing is required, the process continues in FIG. 23, starting with step (23-1).

Figure 23:
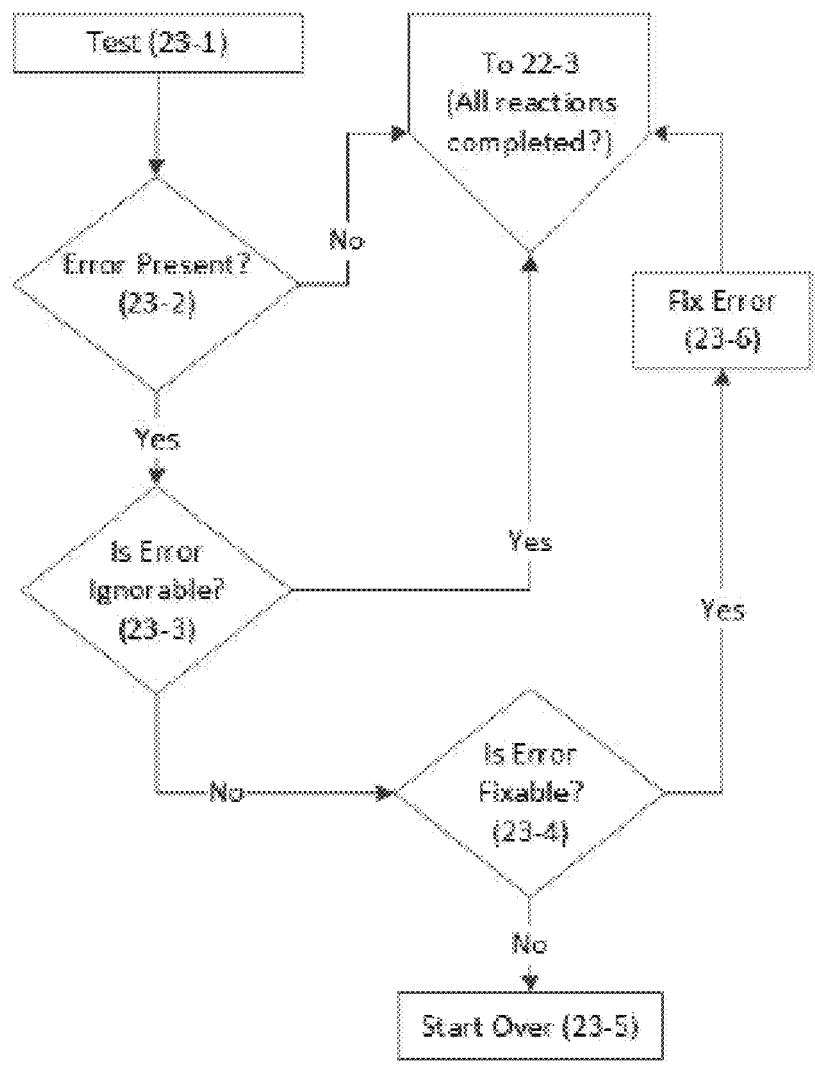
FIG. 23 shows a flow chart for a reaction testing procedure.

In FIG. 23, testing may done by, for example, scanning the surface of a workpiece using AFM or SPM-like techniques and checking to see that the expected structure is present. If no errors are found in (23-2), the process continues at (22-3). If an error is present at (23-2), a decision must be made in (23-3) as to whether the error is ignorable (e.g., not an error that would prevent the workpiece from functioning). If it is ignorable, the process again continues with (22-3), although the build sequence may require adjustment if key atoms were moved as a result of the error (not depicted). If the error is not ignorable, it must be determined if the error can be fixed (23-4). This is largely a question of whether the tools exist to reverse the reaction which caused the error so that the proper reaction can be tried again, although there could be other ways of fixing errors rather than reversing the reaction. If the error can be fixed, this is done in (23-6) and the process continues with (22-3). If the error cannot be fixed, given that it was previously determined to be a crucial error, the build sequence must be started over (23-5).

The embodiment of the process shown in FIG. 23 assumes the ability to fix errors (23-6). This is not necessarily the case, and this flow chart represents only one possible process of implementing mechanosynthesis. For example, it is possible to desire testing without the ability to fix errors, or at least not all errors, if only to know that the workpiece must be discarded and the process started anew, as in (23-5). Product requirements and process capabilities, among other considerations, will determine which steps are actually used, and in what order.

Differentiating Mechanosynthesis Products

Large numbers of natural and synthetic chemical structures, and synthesis pathways, are known outside of mechanosynthesis. And, given these known structures and synthesis pathways, the manufacture of many more hypothetical structures would be obvious. Some of these structures are large (as molecules go), some are stiff and highly-bonded, some are atomically-precise, some contain strained bonds, and some, by various measures, could be considered complex. However, no natural or synthetic structure prepared without the aid of mechanosynthesis, possesses all of these characteristics.

For example, DNA of essentially arbitrary length and sequence can be prepared using conventional techniques. And, given the DNA need not be simply a repetition of the same monomer, by some measures DNA sequences could have high complexity. DNA is not stiff or highly-bonded.

While DNA is a one-dimensional polymer, three-dimensional polymers can also be made large. For example, a dendritic polymer of $2\times10^8$ Daltons has been synthesized (Zhang, Wepf et al., "The Largest Synthetic Structure with Molecular Precision: Towards a Molecular Object," Angewandte Chemie International Edition, 3, WILEY-VCH Verlag, 2011). However, the ability to precisely control the composition of such polymers is lacking, and they tend to be relatively simple polymeric sequences which have been joined in a manner that allows them to assume a three-dimensional shape. The dendritic polymer synthesized by (Zhang, Wepf et al., "The Largest Synthetic Structure with Molecular Precision: Towards a Molecular Object," Angewandte Chemie International Edition, 3, WILEY-VCH Verlag, 2011) is not stiff, highly-bonded, or complex, and subsequent work on error rates at various points in the molecule indicate that it is not atomically-precise.

Structures consisting of multiple adamantane units in random configurations have been purified from petroleum. These structures are stiff and highly-bonded. Additionally, various chemical processes are known to make modified or functionalized adamantane (Szinai, "ADAMANTANE COMPOUNDS," U.S. Pat. No. 3,859,352, United States, Eli Lilly and Company (Indianapolis, Ind.), 1975; Baxter, "Adamantane derivatives," U.S. Pat. No. 6,242,470, United States, AstraZeneca AB (Sodertalje, SE), 2001). However, the adamantane aggregates obtained from natural sources are connected randomly, and so the chances of finding any particular arrangement of adamantanes as the size of the molecule grows becomes vanishingly small. In practicality, these molecules are neither large nor atomically-precise. The functionalized adamantanes used in the pharmaceutical industry are atomically-precise, but they are not large or highly-bonded (since such molecules tend to be, for example, a single adamantane that anchors a long, flexible side chain).

Diamond, whether natural or synthetic (e.g., grown via carbon vapor deposition) is neither complex, being (with the exception of errors) a uniformly repeated three-dimensional polymer of adamantane, nor atomically-precise as even the most perfect such diamond has many flaws at the atomic level. Further, polycrystalline diamond is riddled with random grain boundaries, and the same would be true of the outer surface of monocrystalline diamond, meaning that even if conventional techniques such as CVD could create an internally-perfect crystal, the surface would not be atomically-precise.

With respect to strained bonds, the creation of individual strained bonds is routine in chemistry, and molecules like cyclopropane and cubane exemplify the structures that can be created with strained bonds. Larger structures containing many strained bonds also exist, e.g., Fullerenes of various configurations. While the specific mechanisms of formation are very different, there is a commonality between the synthesis of cyclopropane, cubane, Fullerenes, and other strained molecules in that there are energetically-feasible sequential reaction pathways leading from the initial reactants to the final product.

However, there are classes of strained structures for which this is not true; there is no practical pathway from the component atoms or molecules to the final product using only conventional chemistry. To conceptually illustrate this principle, consider a stiff, rod-shaped molecule. Now, bend the rod into a circle and connect the ends. A hoop-shaped molecule is formed. While hoop-shaped molecules abound, including all the cycloalkanes, and the many other cyclopolymers, the formation of such structures rely upon some fairly restrictive requirements. The main requirement for the formation of these strained structures is that the two ends can be brought close enough together so that they can be bonded together, changing the molecule from a linear structure into a circular structure. The two ends of the linear molecule can be closely approximated in a variety of ways. For example, the molecule can be very small to begin with, so that even if the molecule is straight, the two ends are both within reach of a single reaction. Or, the molecule can be flexible enough that it can bend into the necessary configuration. Or, the linear molecule could have an inherent curve to it, making it already a partial hoop and thereby leaving only a small gap to bridge.

But, consider a class of molecules that do not meet these requirements. A long rod, if stiff enough, even if somewhat curved, with a substantial gap between its ends, cannot be made into a hoop through known conventional chemistry techniques. Similarly, a stiff two-dimensional molecule (e.g., a plane of diamond just one or two adamantane layers thick) will be unable to curl into a tube structure, both because of its stiffness, and possibly because multiple bonds would have to simultaneously form to hold the new tubular structure in place—a statistically unlikely event.

A stiff, long, potentially wide, structure with two sides which are, atomically speaking, far apart, but which need to be brought together to then undergo a bonding reaction to form a stable hoop or cylinder may sound like a very contrived class of structures. It is not. For example, it is exemplary of many of the bearing designs which have been proposed for nano-devices, where an axle revolves inside a stiff cylindrical ring or tube. Mechanosynthesis can form such structures in a variety of ways, such as by using force to approximate the necessary ends, or by building a temporary jig around the structure that forces the intermediate workpiece into the necessary shape.

These are only examples. Comments similar to those about DNA and dendritic polymers apply to other polymers as well, comments similar to those about adamantane apply to the existence or synthesis of other structures, comments similar to those made about diamond apply to other crystals, and certainly rod or plane-shaped structures that need to be folded into hoops or cylinders are not the only example of how positional control allows the formation of structures which could not be made via conventional chemistry due to geometric issues.

Another problem with traditional chemical synthesis methods, geometry issues like those described above aside, is that there is no way to differentiate multiple sites which have similar or identical chemical properties, and yet the end product requires that they be treated differently. Linear polymer synthesis is an exception here, since it is possible to work only at one or a few specific locations (e.g., the ends) of a growing one-dimensional polymer, but these polymers are not stiff, or amenable to the formation of precise, highly-bonded three-dimensional structures.

Once molecules become two or three dimensional, the problem of chemically-equivalent sites at different locations appears. For example, consider a perfectly flat plane of diamond, onto which a structure is to be built. Reactions are known which can add additional carbon (or other) atoms to diamond; this is the basis for CVD-based growth of diamond. However, with the exception of the edges and corners of the plane, which have different bonding structures by virtue of not having the same number of neighboring carbon atoms as the atoms away from the edge, all the sites on the surface of the plane are chemically equivalent. There is no way that CVD, or any technique other than mechanosynthesis can, for example, start adding new atoms to the plane at arbitrary, atomically-precise coordinates.

This concept of multiple chemically similar sites is the reason that three-dimensional dendritic polymers have a simple, repetitious structure: Whatever reaction happens to one branch tends to happen to the equivalent sites on all branches. Beyond dendritic polymers, this general concept is one of the main reasons that synthetic chemistry cannot create arbitrarily large and complex structures.

Certainly mechanosynthesis can be used to make products including DNA and other polymers, small molecules, or repetitious structures of low complexity. In fact, such products would be superior in some ways. For example, products of 100% purity could be created, potentially improving the properties of the product, as well as eliminating waste, and the need for purification steps.

However, when speaking of the possible products of mechanosynthesis, these are not the most important cases since such products, even if inefficiently, can already be created. The more important cases are those structures which cannot reasonably be created or obtained by other means. This tends to mean structures which possess some combination of factors such as being atomically-precise, complex, stiff, highly-bonded, large, or requiring a distribution of strain unobtainable via conventional bulk chemistry.

Generalizing the Exemplary Embodiments

Herein is described how one uses a bootstrap process to go from ultra-sharp, but atomically imprecise, tips to atomically-precise tips for the purpose of facilitating robust mechanosynthesis reactions. This initial set of atomically-precise tips is capable of replicating itself, enabling the continued use of atomically-precise tips after the initial use of the bootstrap process. Also described is the use of computational chemistry techniques to design other reactions, tips that perform those reactions, and the desirable characteristics of those tips.

Additionally, described herein is how one specifies a workpiece using atomic coordinates, determines a build sequence of known reliability using simulated reactions and reaction conditions, and then builds that workpiece using reactions, tips and positional means such as an atomic force microscope, which may be computer-controlled to automate the build sequence process.

During the course of these descriptions, embodiments have been presented which include numerous tips (both atomically-precise and not atomically-precise) and reaction data for dozens of sets of tip/feedstock/workpiece combinations. The list of atoms for which exemplary transfer reactions have been computed spans much of the periodic table, including Al, B, Be, Br, C, Cl, F, Ge, H, Ir, Li, Mg, N, O, Na, P, S, and Si. The tip structures which are used in these transfer reactions use apical atoms including Al, B, C, Ge, N, P and Si.

Also presented is a description of the reactions and build sequences used to create an exemplary complex, three-dimensional pyramidal workpiece which can serve as the basis for a Germanium Radical tool or an Adamantane Radical tool, among other uses. The coaxial trajectory has been noted as frequently being a robust way of performing mechanosynthetic reactions, but other trajectories are possible and varied angles can be useful to avoid steric problems and to facilitate reactions.

It will be obvious that, due to the number of elements in the periodic table and the number of ways that such elements could be arranged, it is impossible to explicitly describe every way in which the invention could be applied or to describe every workpiece that could be created. However, most stable arrangements of atoms could be built using the invention described. Along with the description and theory presented herein, these embodiments, data, reactions and build sequences demonstrate the wide applicability of the invention and provide substantial guidance on how to apply the concepts of the invention to cases beyond the specific embodiments presented herein. In total, the teachings herein will provide the ability to manufacture products via mechanosynthesis, means to modify a workpiece by adding or removing atoms or changing bonding structure at a specific location, bootstrap processes to facilitate the creation of atomically-precise mechanosynthetic tips using non-atomically-precise tips, means for providing feedstock for reactions, methods to design mechanosynthetic reactions and build sequences, methods of computing reaction energetics data for designing mechanosynthetic reactions and build sequences, and procedures facilitating the design of workpieces, among other uses.

What is claimed is:

1. A method of creating a build sequence for a workpiece, comprising:
   a. storing the atomic coordinates of the workpiece in a data storage means;
   b. using computation chemistry algorithms in conjunction with computing means, coupled to the data storage means, to determine a set of mechanosynthetic reactions sufficient to build the workpiece; and
   c. determining an order in which said mechanosynthetic reactions may be performed to result in the workpiece.

2. The method of claim 1 further comprising:
   a. assessing the reliability of one or more of the mechanosynthetic reactions; and
   b. revising the build sequence if the reliability is insufficient.

3. The method of claim 1 wherein the order in which said mechanosynthetic reactions are performed is determined at least in part by steric considerations.

4. The method of claim 1 wherein the order in which mechanosynthetic reactions are performed is determined at least in part to avoid undesired rearrangements in intermediate workpiece structures.

5. The method of claim 1 wherein determining a set of mechanosynthetic reactions is done by choosing from a set of known mechanosynthetic reactions.

6. The method of claim 1 wherein one or more of the mechanosynthetic reactions use a plurality of tips simultaneously.

7. The method of claim 1 wherein the computational chemistry algorithms simulate the use of atomically-precise tips.

8. The method of claim 7 wherein the atomically-precise tips are comprised of adamantane-like structures.

9. A method of creating a build sequence for a workpiece, comprising:
   a. defining the atomic coordinates of the workpiece in a data storage means;
   b. defining the positional error in a positional means used in the workpiece manufacturing process;
   c. using computational chemistry algorithms in conjunction with a computing means coupled to the data storage means to determine an order and set of mechanosynthetic reactions, that, given the positional error in the positional means used in the workpiece manufacturing process, can be used to build the workpiece to a known degree of reliability.

10. A method of creating a build sequence for a workpiece comprising:

a. using computational chemistry algorithms to simulate mechanosynthetic reactions at a given temperature and with realistic equipment limitations; and
b. determining a set of, and order of, the mechanosynthetic reactions that will build the workpiece with a desired degree of reliability.

* * * * *